US011312997B2

(12) United States Patent
Cantor et al.

(10) Patent No.: US 11,312,997 B2
(45) Date of Patent: *Apr. 26, 2022

(54) METHODS AND PROCESSES FOR NON-INVASIVE ASSESSMENT OF GENETIC VARIATIONS

(71) Applicant: Sequenom, Inc., San Diego, CA (US)

(72) Inventors: Charles R. Cantor, Del Mar, CA (US); Grace DeSantis, San Diego, CA (US); Reinhold Mueller, San Diego, CA (US); Mathias Ehrich, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,528

(22) Filed: May 27, 2020

(65) Prior Publication Data

US 2020/0362412 A1    Nov. 19, 2020

Related U.S. Application Data

(63) Continuation of application No. 15/443,051, filed on Feb. 27, 2017, now Pat. No. 10,738,359, which is a continuation of application No. 13/782,901, filed on Mar. 1, 2013, now Pat. No. 9,605,313.

(60) Provisional application No. 61/606,226, filed on Mar. 2, 2012.

(51) Int. Cl.
   C12Q 1/6883    (2018.01)
   C07K 16/18     (2006.01)
   C12Q 1/6804    (2018.01)

(52) U.S. Cl.
   CPC .......... *C12Q 1/6883* (2013.01); *C07K 16/18* (2013.01); *C12Q 1/6804* (2013.01)

(58) Field of Classification Search
   CPC ..... C12Q 1/6883; C12Q 1/6804; C07K 16/18
   See application file for complete search history.

(56) References Cited

U.S. PATENT DOCUMENTS

| | | |
|---|---|---|
| 4,109,496 A | 8/1978 | Allemann et al. |
| 4,179,337 A | 12/1979 | Davis et al. |
| 4,458,066 A | 7/1984 | Caruthers et al. |
| 4,469,863 A | 9/1984 | Ts'o et al. |
| 4,522,811 A | 6/1985 | Eppstein et al. |
| 4,656,127 A | 4/1987 | Mundy |
| 4,676,980 A | 6/1987 | Segal et al. |
| 4,683,195 A | 7/1987 | Mullis et al. |
| 4,683,202 A | 7/1987 | Mullis |
| 4,851,331 A | 7/1989 | Vary et al. |
| 4,868,103 A | 9/1989 | Stavrianopoulos et al. |
| 4,873,316 A | 10/1989 | Meade et al. |
| 4,965,188 A | 10/1990 | Mullis et al. |
| 5,048,530 A | 9/1991 | Hurwitz |
| 5,075,212 A | 12/1991 | Rotbart |
| 5,118,937 A | 6/1992 | Hillenkamp et al. |
| 5,210,015 A | 5/1993 | Gelfand et al. |
| 5,272,071 A | 12/1993 | Chappel et al. |
| 5,283,317 A | 2/1994 | Saifer et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,536,821 A | 7/1996 | Agrawal et al. |
| 5,541,306 A | 7/1996 | Agrawal et al. |
| 5,547,835 A | 8/1996 | Koster |
| 5,589,330 A | 12/1996 | Shuber |
| 5,605,798 A | 2/1997 | Koster |
| 5,614,622 A | 2/1997 | Iyer et al. |
| 5,631,169 A | 5/1997 | Lakowicz et al. |
| 5,637,683 A | 6/1997 | Usher et al. |
| 5,637,684 A | 6/1997 | Cook |
| 5,656,493 A | 8/1997 | Mullis et al. |
| 5,679,524 A | 10/1997 | Nikiforov et al. |
| 5,691,141 A | 11/1997 | Koster |
| 5,695,940 A | 12/1997 | Drmanac et al. |
| 5,700,922 A | 12/1997 | Cook |
| 5,717,083 A | 2/1998 | Cook et al. |
| 5,719,262 A | 2/1998 | Buchardt et al. |
| 5,720,928 A | 2/1998 | Schwartz |
| 5,739,308 A | 4/1998 | Kandimalla et al. |
| 5,739,314 A | 4/1998 | Roy et al. |
| 5,766,849 A | 6/1998 | McDonough et al. |
| 5,773,601 A | 6/1998 | Agrawal |
| 5,786,146 A | 7/1998 | Herman et al. |
| 5,834,189 A | 11/1998 | Stevens et al. |
| 5,849,483 A | 12/1998 | Shuber |
| 5,849,497 A | 12/1998 | Steinman |
| 5,849,542 A | 12/1998 | Reeve et al. |
| 5,849,546 A | 12/1998 | Sousa et al. |

(Continued)

FOREIGN PATENT DOCUMENTS

| | | |
|---|---|---|
| EP | 264166 | 4/1988 |
| EP | 0401384 | 12/1990 |

(Continued)

OTHER PUBLICATIONS

Van den Ackerveken et al., Scientific Reports, 11(1):7256, Mar. 31, 2021.*

Abyzov et al.; "CNVnator: An approach to discover, genotype, and characterize typical and atypical CNVs from family and population genome sequencing"; Genome Research; Feb. 7, 2011; pp. 974-984; vol. 21. No. 6.

Adinolfi et al.; Rapid detection of aneuploidies by microsatellite and the quantitative fluorescent polymerase chain reaction; Prenatal Diagnosis; Dec. 1997; pp. 1299-1311; vol. 17, No. 13.

(Continued)

*Primary Examiner* — Cynthia B Wilder

(74) *Attorney, Agent, or Firm* — Kilpatrick Townsend & Stockton LLP

(57) ABSTRACT

Technology provided herein relates in part to methods, processes and apparatuses for non-invasive assessment of genetic variations.

14 Claims, 6 Drawing Sheets

(56) References Cited

U.S. PATENT DOCUMENTS

| | | |
|---|---|---|
| 5,851,770 A | 12/1998 | Babon et al. |
| 5,869,242 A | 2/1999 | Kamb |
| 5,876,934 A | 3/1999 | Duthie et al. |
| 5,886,165 A | 3/1999 | Kandimalla et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,929,226 A | 7/1999 | Padmapriya et al. |
| 5,952,174 A | 9/1999 | Nikiforov et al. |
| 5,955,599 A | 9/1999 | Lyer et al. |
| 5,958,692 A | 9/1999 | Cotton et al. |
| 5,962,674 A | 10/1999 | Lyer et al. |
| 5,976,802 A | 11/1999 | Ansorge et al. |
| 5,977,296 A | 11/1999 | Nielsen et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,029,041 A | 1/2000 | Drmanac et al. |
| 6,024,925 A | 2/2000 | Little et al. |
| 6,043,031 A | 3/2000 | Kister et al. |
| 6,045,996 A | 4/2000 | Cronin et al. |
| 6,046,005 A | 4/2000 | Ju et al. |
| 6,057,134 A | 5/2000 | Lader et al. |
| 6,057,143 A | 5/2000 | Lader et al. |
| 6,087,095 A | 7/2000 | Rosenthal et al. |
| 6,107,037 A | 8/2000 | Sousa et al. |
| 6,110,684 A | 8/2000 | Kemper et al. |
| 6,117,992 A | 9/2000 | Lyer |
| 6,136,541 A | 10/2000 | Gulati |
| 6,140,053 A | 10/2000 | Koster |
| 6,140,054 A | 10/2000 | Whittwer et al. |
| 6,140,482 A | 10/2000 | Lyer et al. |
| 6,142,681 A | 11/2000 | Gulati |
| 6,143,496 A | 11/2000 | Brown et al. |
| 6,156,501 A | 12/2000 | McGall et al. |
| 6,183,958 B1 | 2/2001 | Stanton, Jr. |
| 6,194,144 B1 | 2/2001 | Koster |
| 6,194,180 B1 | 2/2001 | Joyce |
| 6,197,506 B1 | 3/2001 | Fodor et al. |
| 6,210,574 B1 | 4/2001 | Sammons et al. |
| 6,210,891 B1 | 4/2001 | Nyren et al. |
| 6,214,556 B1 | 4/2001 | Olek et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,638 B1 | 6/2001 | Umansky et al. |
| 6,258,538 B1 | 7/2001 | Koster et al. |
| 6,258,540 B1 | 7/2001 | Lo et al. |
| 6,297,028 B1 | 10/2001 | Taniguchi et al. |
| 6,326,174 B1 | 12/2001 | Joyce et al. |
| 6,368,834 B1 | 4/2002 | Senapathy et al. |
| 6,440,706 B1 | 8/2002 | Vogelstein et al. |
| 6,468,748 B1 | 10/2002 | Monforte et al. |
| 6,610,492 B1 | 8/2003 | Stanton, Jr. et al. |
| 6,664,056 B2 | 12/2003 | Lo et al. |
| 6,723,513 B2 | 4/2004 | Lexow |
| 6,759,217 B2 | 7/2004 | Kopreski |
| 6,794,142 B2 | 9/2004 | Laird et al. |
| 6,818,394 B1 | 11/2004 | O'Donnell-Maloney et al. |
| 6,884,586 B2 | 4/2005 | Van Ness et al. |
| 6,916,634 B2 | 7/2005 | Kopreski |
| 6,927,028 B2 | 8/2005 | Dennis et al. |
| 6,929,911 B2 | 8/2005 | Oefner et al. |
| 7,081,339 B2 | 7/2006 | Slepnev |
| 7,169,314 B2 | 1/2007 | Unger et al. |
| 7,244,567 B2 | 7/2007 | Chen et al. |
| 7,253,259 B2 | 8/2007 | Otagiri et al. |
| 7,285,422 B1 | 10/2007 | Little et al. |
| 7,468,249 B2 | 12/2008 | Xie et al. |
| 7,655,399 B2 | 2/2010 | Cantor et al. |
| 7,709,194 B2 | 5/2010 | Lo et al. |
| 7,709,262 B2 | 5/2010 | Cantor et al. |
| 7,754,428 B2 | 7/2010 | Lo et al. |
| 7,785,798 B2 | 8/2010 | Cantor et al. |
| 7,901,884 B2 | 3/2011 | Lo et al. |
| 8,195,415 B2 | 6/2012 | Fan et al. |
| 8,518,228 B2 | 8/2013 | Marziali |
| 8,706,422 B2 | 4/2014 | Lo et al. |
| 9,074,013 B2 | 7/2015 | Rehli |
| 9,187,780 B2 | 11/2015 | Micallef et al. |
| 9,189,086 B2 | 11/2015 | McGibney et al. |
| 9,222,937 B2 | 12/2015 | Micallef |
| 9,249,464 B2 | 2/2016 | Rehli |
| 9,400,276 B2 | 7/2016 | Micallef |
| 9,605,313 B2 | 3/2017 | Cantor et al. |
| 9,709,569 B2 | 7/2017 | Micallef et al. |
| 10,738,359 B2 | 8/2020 | Cantor et al. |
| 2001/0008615 A1 | 7/2001 | Little et al. |
| 2001/0051341 A1 | 12/2001 | Lo et al. |
| 2002/0006621 A1 | 1/2002 | Bianchi |
| 2003/0022207 A1 | 1/2003 | Balasubramanian et al. |
| 2003/0082600 A1 | 5/2003 | Olek et al. |
| 2003/0087276 A1 | 5/2003 | Kopreski |
| 2003/0096426 A1 | 5/2003 | Little et al. |
| 2003/0180748 A1 | 9/2003 | Braun et al. |
| 2003/0180779 A1 | 9/2003 | Lofton-Day et al. |
| 2003/0211483 A1 | 11/2003 | Schroeder et al. |
| 2003/0211522 A1 | 11/2003 | Lands et al. |
| 2004/0014105 A1 | 1/2004 | Schroeder et al. |
| 2004/0081993 A1 | 4/2004 | Cantor et al. |
| 2004/0115684 A1 | 6/2004 | Costa |
| 2004/0137470 A1 | 7/2004 | Dhallan |
| 2004/0203037 A1 | 10/2004 | Lo et al. |
| 2005/0037388 A1 | 2/2005 | Antonarakis et al. |
| 2005/0059003 A1 | 3/2005 | Enoki et al. |
| 2005/0064406 A1 | 3/2005 | Zabarobsky et al. |
| 2005/0064428 A1 | 3/2005 | Berlin |
| 2005/0069879 A1 | 3/2005 | Berlin |
| 2005/0069931 A1* | 3/2005 | Allis ............... C12Q 2563/119 435/6.12 |
| 2005/0079521 A1 | 4/2005 | Beaulieu et al. |
| 2005/0112590 A1 | 5/2005 | Boom et al. |
| 2005/0009059 A1 | 7/2005 | Shapero et al. |
| 2005/0019762 A1 | 7/2005 | Olek |
| 2005/0153316 A1 | 7/2005 | Jeddeloh et al. |
| 2005/0153347 A1 | 7/2005 | Shapero et al. |
| 2005/0164241 A1 | 7/2005 | Hahn et al. |
| 2005/0266473 A1 | 12/2005 | Zhang et al. |
| 2005/0272070 A1 | 12/2005 | Ehrich et al. |
| 2005/0287592 A1 | 12/2005 | Kless |
| 2006/0019278 A1 | 1/2006 | Lo et al. |
| 2006/0094039 A1 | 5/2006 | Rosenfeld et al. |
| 2006/0136142 A1 | 7/2006 | Berlin et al. |
| 2006/0160105 A1 | 7/2006 | Dhallan |
| 2006/0166228 A1 | 7/2006 | Page et al. |
| 2006/0210992 A1 | 9/2006 | van den Boom |
| 2006/0252068 A1 | 11/2006 | Lo et al. |
| 2006/0252071 A1 | 11/2006 | Lo et al. |
| 2007/0048755 A1 | 3/2007 | Di Fiore |
| 2007/0065823 A1 | 3/2007 | Dressman et al. |
| 2007/0597074 | 3/2007 | Cantor et al. |
| 2007/0111233 A1 | 5/2007 | Bianchi et al. |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0275402 A1 | 11/2007 | Lo et al. |
| 2008/0020390 A1 | 1/2008 | Mitchell et al. |
| 2008/0070792 A1 | 3/2008 | Stoughton et al. |
| 2008/0096766 A1 | 4/2008 | Lee |
| 2008/0299562 A1 | 12/2008 | Oeth et al. |
| 2008/0305479 A1 | 12/2008 | Van Den Boom et al. |
| 2009/0026082 A1 | 1/2009 | Rothberg et al. |
| 2009/0029377 A1 | 1/2009 | Lo et al. |
| 2009/0053719 A1 | 2/2009 | Lo et al. |
| 2009/0061425 A1 | 3/2009 | Lo et al. |
| 2009/0111712 A1 | 4/2009 | Van Den Boom et al. |

(56) References Cited

U.S. PATENT DOCUMENTS

| | | |
|---|---|---|
| 2009/0142755 A1 | 6/2009 | Albitar |
| 2009/0202984 A1 | 8/2009 | Cantor |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0184046 A1 | 7/2010 | Klass et al. |
| 2010/0203529 A1 | 8/2010 | Kuslich et al. |
| 2010/0216153 A1 | 8/2010 | Lapidus et al. |
| 2010/0227320 A1 | 9/2010 | Fu |
| 2010/0240054 A1 | 9/2010 | Bischoff |
| 2010/0273165 A1 | 10/2010 | Ehrich et al. |
| 2010/0279295 A1 | 11/2010 | Roy et al. |
| 2011/0033851 A1 | 2/2011 | Rand |
| 2011/0039724 A1 | 2/2011 | Lo et al. |
| 2011/0105353 A1* | 5/2011 | Lo .................. G16B 30/00 506/9 |
| 2011/0151460 A1 | 6/2011 | Klass et al. |
| 2011/0177517 A1 | 7/2011 | Rava et al. |
| 2011/0178719 A1 | 7/2011 | Rabinowitz et al. |
| 2011/0201507 A1 | 8/2011 | Rava et al. |
| 2011/0212846 A1 | 9/2011 | Spier |
| 2011/0224087 A1 | 9/2011 | Quake et al. |
| 2011/0244451 A1 | 10/2011 | Cantor et al. |
| 2011/0266780 A1 | 11/2011 | Rabinowirz et al. |
| 2011/0276277 A1 | 11/2011 | Lo et al. |
| 2011/0288780 A1 | 11/2011 | Rabinowitz et al. |
| 2012/0065076 A1 | 3/2012 | Peters et al. |
| 2012/0184449 A1 | 7/2012 | Hixson et al. |
| 2012/0196754 A1 | 8/2012 | Quake et al. |
| 2012/0264618 A1 | 10/2012 | Nygren |
| 2012/0028613 A1 | 11/2012 | Patsalis et al. |
| 2012/0276542 A1 | 11/2012 | Nygren |
| 2012/0277119 A1 | 11/2012 | Ehrich et al. |
| 2012/0282613 A1 | 11/2012 | Patsalis et al. |
| 2012/0322072 A1 | 12/2012 | Nygren |
| 2013/0012399 A1 | 1/2013 | Myers et al. |
| 2013/0022974 A1 | 1/2013 | Chinnaiyan et al. |
| 2013/0065254 A1 | 3/2013 | Lunyak |
| 2013/0085681 A1 | 4/2013 | Deciu et al. |
| 2013/0130923 A1 | 5/2013 | Ehrich et al. |
| 2013/0143211 A1 | 6/2013 | Ehrich et al. |
| 2013/0150249 A1 | 6/2013 | Ehrich et al. |
| 2013/0230858 A1 | 9/2013 | Cantor et al. |
| 2013/0237431 A1 | 9/2013 | Lo et al. |
| 2013/0295564 A1 | 11/2013 | Ehrich et al. |
| 2013/0296180 A1 | 11/2013 | Ehrich et al. |
| 2013/0310260 A1 | 11/2013 | Kim et al. |
| 2014/0093873 A1 | 4/2014 | Tynan et al. |
| 2014/0180594 A1 | 6/2014 | Kim et al. |
| 2015/0267263 A1 | 9/2015 | Rehli |
| 2015/0275304 A1 | 10/2015 | Ehrich et al. |
| 2016/0145685 A1 | 5/2016 | Jensen et al. |
| 2016/0201113 A1 | 7/2016 | Rehli |
| 2017/0073756 A1 | 3/2017 | Jensen et al. |
| 2017/0316150 A1 | 11/2017 | Deciu et al. |
| 2017/0321276 A1 | 11/2017 | Cantor et al. |

FOREIGN PATENT DOCUMENTS

| | | |
|---|---|---|
| EP | 1373561 | 2/2009 |
| EP | 1524321 | 4/2009 |
| EP | 2820129 | 1/2015 |
| EP | 3117011 | 1/2017 |
| EP | 3175000 | 6/2017 |
| EP | 3204512 | 8/2017 |
| HK | 1206055 | 12/2015 |
| HK | 1227442 | 10/2017 |
| HK | 1234787 | 2/2018 |
| JP | 2005-514956 | 5/2005 |
| JP | 2007505641 | 3/2007 |
| JP | 2008-521389 | 6/2008 |
| JP | 2009529330 | 8/2009 |
| JP | 5727375 | 4/2015 |
| JP | 2015126748 | 7/2015 |
| JP | 5873434 | 1/2016 |
| JP | 5923571 | 4/2016 |
| WO | 1991/006667 | 5/1991 |
| WO | 1994/010300 | 5/1994 |
| WO | 1997/012058 | 4/1997 |
| WO | 1997/035589 | 10/1997 |
| WO | 1997/037041 | 10/1997 |
| WO | 1998/020020 | 5/1998 |
| WO | 1998/022489 | 5/1998 |
| WO | 98/39474 | 9/1998 |
| WO | 1998/039352 | 9/1998 |
| WO | 1998/039474 | 9/1998 |
| WO | 1998/054364 | 12/1998 |
| WO | 1999/057318 | 5/1999 |
| WO | 00/41147 | 7/2000 |
| WO | 2000/052625 | 9/2000 |
| WO | 2000/056746 | 9/2000 |
| WO | 2000/066771 | 11/2000 |
| WO | 2000/075372 | 12/2000 |
| WO | 2001/014398 | 3/2001 |
| WO | 2001/020039 | 3/2001 |
| WO | 2001/025485 | 4/2001 |
| WO | 2001/027326 | 4/2001 |
| WO | 2001/027327 | 4/2001 |
| WO | 2001/027329 | 4/2001 |
| WO | 2001/029259 | 4/2001 |
| WO | 2002/018616 | 3/2002 |
| WO | 2002/086163 | 10/2002 |
| WO | 2003/000919 | 1/2003 |
| WO | 03/020974 | 3/2003 |
| WO | 2003/057909 | 7/2003 |
| WO | 2003/062441 | 7/2003 |
| WO | 2003/070894 | 8/2003 |
| WO | 2003/080863 | 10/2003 |
| WO | 2004/013284 | 2/2004 |
| WO | 2004/076653 | 9/2004 |
| WO | 2004/078999 | 9/2004 |
| WO | 2004/079011 | 9/2004 |
| WO | 2005/012578 | 2/2005 |
| WO | 2005/021793 | 3/2005 |
| WO | 2005/023091 | 3/2005 |
| WO | 2005/035725 | 4/2005 |
| WO | 2005/040399 | 5/2005 |
| WO | 2005/098050 | 10/2005 |
| WO | 2005/118852 | 12/2005 |
| WO | 2006/056480 | 6/2006 |
| WO | 2006/097049 | 9/2006 |
| WO | 2006/097051 | 9/2006 |
| WO | 2007/016668 | 2/2007 |
| WO | 2007/028155 | 3/2007 |
| WO | 2007/092473 | 8/2007 |
| WO | 2007/100911 | 9/2007 |
| WO | 2007/121276 | 10/2007 |
| WO | 2007/132166 | 11/2007 |
| WO | 2007/132167 | 11/2007 |
| WO | 2007/140417 | 12/2007 |
| WO | 2007/147063 | 12/2007 |
| WO | 2008/098142 | 8/2008 |
| WO | 2008/103761 | 8/2008 |
| WO | 2008/103763 | 8/2008 |
| WO | 2008/118988 | 10/2008 |
| WO | 2008/157264 | 12/2008 |
| WO | 2009/030100 | 3/2009 |
| WO | 2009/032779 | 3/2009 |
| WO | 2009/032781 | 3/2009 |
| WO | 2009/039507 | 3/2009 |
| WO | 2009/046445 | 4/2009 |
| WO | 2009/091934 | 7/2009 |
| WO | 2009/114543 | 9/2009 |
| WO | 2010/004265 | 1/2010 |
| WO | 2010/033639 | 3/2010 |
| WO | 2010/065470 | 6/2010 |
| WO | 2010/115016 | 10/2010 |
| WO | 2010/033639 | 2/2011 |
| WO | 2011/018600 | 2/2011 |
| WO | 2011/034631 | 3/2011 |
| WO | 2011/051283 | 5/2011 |
| WO | 2011/087760 | 7/2011 |
| WO | 2011/091063 | 7/2011 |

(56) References Cited

FOREIGN PATENT DOCUMENTS

| WO | 2011/092592 | 8/2011 |
|---|---|---|
| WO | 2011/142836 | 11/2011 |
| WO | 2011/143659 | 11/2011 |
| WO | 2011/150974 | 12/2011 |
| WO | 2011/142836 | 1/2012 |
| WO | 2012/071621 | 6/2012 |
| WO | 2012/118745 | 9/2012 |
| WO | 2012/149339 | 11/2012 |
| WO | 2013/052913 | 4/2013 |
| WO | 2013/055817 | 4/2013 |
| WO | 2013/109981 | 7/2013 |
| WO | 2013/131021 | 9/2013 |
| WO | 2013/177086 | 11/2013 |
| WO | 2014/011928 | 1/2014 |
| WO | 2014/168711 | 10/2014 |
| WO | 2014/190286 | 11/2014 |
| WO | 2015/040591 | 3/2015 |
| WO | 2015/061359 | 4/2015 |
| WO | 2015/138774 | 9/2015 |
| WO | 2016/019042 | 2/2016 |
| WO | 2016/057901 | 4/2016 |
| WO | 2016/067029 | 5/2016 |
| WO | 2017/068371 | 4/2017 |

OTHER PUBLICATIONS

Agresti; Categorical Data Analysis; $2^{nd}$ Edition; 2002; Wiley.
Altschul et al.; "Basic local alignment search tool;" J Mol Biology; Oct. 1990; pp. 403-410; vol. 215, No. 3.
Altschul et al.; "Gapped BLAST and PSI-BLAST: a new generation of protein database search programs;" Nucleic Acids Res.; Sep. 1, 1997; pp. 3389-3402; vol. 25, No. 17.
Amicucci et al.; Clinical Chemistry; 2000; pp. 301-302; vol. 46.
Amir, et al.; Nature Genetics; 1999; pp. 185-188; vol. 23.
Anantha et al.; "Porphyrin binding to quadrupled T4G4;" Biochemistry; Mar. 3, 1998; pp. 2409-2714; vol. 37, No. 9.
Anders et al.; Clinical Chemistry; Oct. 2010; E-pub Aug. 20, 2010; pp. 1627-1635; vol. 56, No. 10.
Anderson; "Shotgun DNA sequencing using closed Dnase I-generated fragments;" Nuclear Acids Research; 1981; pp. 3015-3027; vol. 9.
Antonarakis et al.; American Journal of Human Genetics; Mar. 1992; pp. 544-550; vol. 50, No. 3.
Antonarakis et al.; Natural Genetics; Feb. 1993; pp. 146-150; vol. 3, No. 2.
Aoki et al.; "Methylation status of the p15INK4B gene in hematopoietic progenitors and peripheral blood cells in myelodysplastic syndromes"; Leukemia; 2000; pp. 586-593; vol. 14, No. 4.
Armour et al.; "Measurement of locus copy number by hybridization with amplifiable probes;" Nucleic Acids Research; Jan. 2000; pp. 605-609; vol. 28, No. 2.
Armour et al.; "The detection of large deletions or duplications in genomic DNA;" Human Mutation; Nov. 2002; pp. 325-337; vol. 20, No. 5.
Asimakopoulos, et al.; "ABL 1 methylation is a distinct molecular event associated with clonal evolution of chronic myeloid leukemia;" Blood; 1999; pp. 2452-2460; vol. 94, No. 7.
Assis et al.; Journal of Experimental and Clinical Cancer Research; 2015; pp. 1-11; vol. 34, No. 65.
Aston et al.; Methods in Enzymology.; 1999; pp. 55-73; vol. 303.
Aston et al.; Trends Biotechnology; 1999; pp. 297-302; vol. 17, No. 7.
Ausubel et al.; Current Protocols in Molecular Biology; 1994.
Banerji et al.; "A lymphocyte-specific cellular enhancer is located downstream of the joining region in immunoglobulin heavy chain genes;" Cell; Jul. 1983; pp. 729-740; vol. 33, No. 3.
Bartel et al.; Biotechniques; 1993; pp. 920-924; vol. 14.
Batey et al.; Nucleic Acids Research; 1992; pp. 4515-4523; vol. 20.
Batey et al.; Nucleic Acids Research; 1996; pp. 4836-4837; vol. 24.
Batzer et al.; Nucleic Acids Research; 1991; p. 5081; vol. 19.

Beaucage & Caruthers, Tetrahedron Letters; 1981; pp. 1859-1862; vol. 22.
Beaudet; "Progress toward noninvasive prenatal diagnosis;" Clinical Chemistry; 2011; pp. 802-804; vol. 57, No. 6.
Beckman Coulter; Introduction to Capillary Electrophoresis; Beckman Coulter 1991.
Benson G.; "Tandem repeats finder: a program to analyze DNA sequences;" Nucleic Acids Research; Jan. 15, 1999; pp. 573-580; vol. 27, No. 2.
Bianchi; "Fetal cells in the mother: from genetic diagnosis to diseases associated with fetal cell microchimerism"; European Journal of Obstetrics & Gynecology and Reproductive Biology; Sep. 2000; pp. 103-108; vol. 92, No. 1.
Bock et al.; "CpG island methylation in human lymphocytes is highly correlated with DNA sequence, repeats, and predicted DNA structure"; PLOS Genetics; 2006; p. e26; vol. 2, No. 3.
Boguski et al.; Identification of a cytidine-specific ribonuclease from chicken liver; J. Biology Chemistry; Mar. 10, 1980; pp. 2160-2163; vol. 255, No. 5.
Boome et al.; J. Clinical Microbiology; 1990; pp. 495-503; vol. 28.
Boome et al.; J. Clinical Microbiology; 1991; pp. 1804-1811 vol. 29.
Boyer, et al.; "Polycomb complexes repress development regulators in murine embryonic stem cells;" Nature; 2006; pp. 349-353; vol. 441.
Braslavsky et al.; Sequence information can be obtained from single DNA molecules; Pro National Academy Science U S A; Apr. 1, 2003; E-pub Mar. 21, 2003; pp. 3960-3964; vol. 100, No. 7.
Brizot et al.; "Maternal serum hCG an fetal nuchal translucency thickness for the prediction of fetal trisomies in the first trimester of pregnancy;" British Journal of Obstetrics Gynaecology; Feb. 1995; pp. 127-132; vol. 102, No. 2.
Bullinger et al.; "Use of gene-expression profiling to identifying prognostic subclasses in adult acute myeloid leukemia;" New England Journal of Medicine; Apr. 15, 2004; pp. 1605-1616; vol. 350, No. 16.
Burlingame et al.; Analytical Chemistry; 1998; pp. 647R-716R; vol. 70.
Burnier et al.; "Cell-derived microparticles in haemostasis and vascular medicine;" Thromb Haemost; 2009; pp. 439-451; vol. 101.
Bryne et al.; "Multiplex gene regulation: a two-tiered approach to transgene regulation in transgenic mice." Proc National Academy Science U S A; Jul. 1989; pp. 5473-5477; vol. 86, No. 14.
Calame et al.; "Transcriptional controlling elements in the immunoglobulin and T cell receptor loci." Advance Immunology; 1988 pp. 235-275; vol. 43.
Caliper LifeSciences, Products and Contract Services, LabChip GX 2010 printed from the internet on Mar. 15, 2011; http://www.caliperl.com/products/labchip-gx.htm.
Camper et al.; "Postnatal repression of the alpha-fetoprotein gene is enhancer independent." Genes Development; Apr. 1989; pp. 537-546; vol. 3, No. 4.
Cell Death Detection Elisa Plus Cat. No. 11 774 425 001 "Detection of Posttranslational Modifications of Native Intact Nucleosomes by ELISA;" Version 11.0, Roche, Content Version: Sep. 2010, pp. 1-19.
Chan et al.; Clinical Chemistry; 2004; pp. 88-92; vol. 50.
Chan et al.; "Hypermethylated RASSFIA in Maternal Plasma: A Universal Fetal DNA Marker that improves the reliability of Noninvasive Prenatal Diagnosis"; Clinical Chemistry; 2006; pp. 2211-2218; vol. 52.
Chan et al.; Oncogene; 2003; pp. 924-934; vol. 22.
Chang et al.; "LIBSVM: a library for Support Vector Machines;" 2001.
Chen et al., "A method for noninvasive detection of fetal large deletions/duplications by low coverage massively parallel sequencing" Prenatal Diagnosis; 2013; pp. 584-590; vol. 33.
Chen et al.; Fluorescence energy transfer detection as a homogeneous DNA diagnostic method; Proceedings of National Academy Science U S A; Sep. 30, 1997; pp. 10756-10761; vol. 94, No. 20.
Chen et al.; "Noninvasive Prenatal Diagnosis of Fetal Trisomy 18 and Trisomy 13 by Maternal Plasma DNA Sequencing"; PLoS ONE; Jul. 6, 2011; pp. e21791; vol. 6, No. 7.

(56) References Cited

OTHER PUBLICATIONS

Chen et al.; "Template-directed dye-terminator incorporation (TDI) assay: a homogeneous DNA diagnostic method based on fluorescence resonance energy transfer;" Nucleic Acids Res; Jan. 15, 1997; pp. 347-353; vol. 25, No. 2.
Cheson et al.; "Report of the National Cancer Institute-sponsored workshop on definitions of diagnosis and response in acute myeloid leukemia;" J. Clinical Oncology; 1990; pp. 813-819; vol. 8.
Cheung et al.; J. Clinical Microbiology; 1994; pp. 2593-2597; vol. 32.
Chirgwin et al.; Biochemistry; 1979; pp. 5294-5299; vol. 18.
Chitty; British Medical Bulletin; 1998; pp. 839-856; vol. 54.
Chiu et al.; "Effects of blood-processing protocols on fetal and total DNA quantification in maternal plasma;" Clinical Chemistry; 2001; pp. 1607-1613; vol. 47, No. 9.
Chiu et al.; Lancet; 2002; pp. 998-1000; vol. 360.
Chomczynski and Mackey; Analytical Biochemistry.; 1995; pp. 163-164; vol. 225.
Chomczynski and Mackey; Biotechniques; 1995; pp. 942-945; vol. 19.
Chomczynski and Sacchi; Analytical Biochemistry; 1987; pp. 156-159; vol. 162.
Chomczynski; Biotechnology; 1993; pp. 532-537; vol. 15.
Chow, et al.; Mass Spectrometric detection of SNP panel as an internal positive control for fetal DNA analysis in maternal plasma; Clinical Chemistry; 2007; pp. 141-142; vol. 53.
Chu et al.; "A novel approach toward the challenge of accurately quantifying fetal DNA in maternal plasma; " Prenatal Diagnosis; 2010; pp. 1226-1229; vol. 30.
Colella et al.; Biotechniques; 2003; pp. 146-150; vol. 35, No. 1.
Costa et al.; New England Journal of Medicine; 2002; p. 1502; vol. 346.
Costello et al.; "Restriction Landmark Genomic Scanning (RLGS): Analysis of CpG Islands in genomes by 2D Gel Electrophoresis, Methods in Molecular Biology, DNA Methylation;" 2 Methods and Protocols; 2000; pp. 131-148; $2^{nd}$ eds.; vol. 507.
Cross et al.; "Purification of CpG islands using a methylated DNA biding column"; Nature Genetics; 1994; pp. 236-244; vol. 6, No. 3.
Cruikshank et al.; "A lapidated anti-Tat antibody enters living cells and blocks HIV-1 viral replication; " J. Acquired Immune Deficiency Syndromes and Human Retrovirology; Mar. 1, 1997; pp. 193-203; vol. 14, No. 3.
Currant Protocols in Molecular Biology; John Wiley & Sons, New York; 6.3.1-6.3.6; 1989.
Dai et al., "Detection of Post-translational Modifications on Native Intact Nucleosomes by ELISA, " Journal of Visualized Experiments; 2011; pp. 1-4.
D'Alton; "Prenatal diagnostic procedures;" Semin Perinatol.; 1994; pp. 140-162; vol. 18, No. 3.
Das et al.; Proc National Academy of Science USA; 2006; pp. 10713-10716; vol. 103.
Davison; "Sedimentation of deoxyribonucleic acid isolated under low hydrodynamic shear;" Nature; Mar. 26, 1960; pp. 918-920; vol. 26, No. 185.
Davison; "The Effect of Hydrodynamic Shear on the Deoxyribonucleic Acid from T(2) and T(4) Bacteriophages; " Proc National Academy of Science U S A; Nov. 1959; pp. 1560-1568; vol. 45, No. 11.
Dayie et al.; Journal of Magnetic Resonance; 1998; pp. 97-101; vol. 130.
DEAR: "One by one: Single molecule tools for genomics;" Briefings in Functional Genomics & Proteomics; Jan. 2003; pp. 397-416; vol. 1, No. 4.
Deligezer et al., "Sequence-Specific Histone Methylation is Detectable on Circulating Nucleosomes in Plasma," Clin. Chem. 54(7):1125-1131 (2008).
Deininger; "Random subcloning of sonicated DNA: application to shotgun DNA sequence analysis;" Analytical Biochemistry; 1983; pp. 216-223; vol. 129, No. 1.
Dembo et al.; Annals of Probability; 1994; pp. 2022-2039; vol. 22.

Ding et al.; A high-throughput gene expression analysis technique using competitive PCR and matrix-assisted laser desorption ionization time-of-flight MS; Pro National Academy of Science U S A; 2003; pp. 3059-3064; vol. 100.
Donis-Keller et al.; Nucleic Acids Research; 1977; pp. 2527-2537; vol. 4.
Donis-Keller et al.; "Phy M: An RNase activity specific for U and A residues useful in RNA sequence analysis;" Nucleic Acids Research; Jul. 25, 1980; pp. 3133-3142; vol. 8, No. 14.
Dupont et al.; Analytical Biochemistry; Oct. 2004; pp. 119-127; vol. 333, No. 1.
Eads et al.; Cancer Research; 1999; pp. 2302-2306; vol. 59.
Eckhardt et al.; Nature Genetics; 2006; pp. 1378-1385; vol. 38.
Edlund et al.; "Cell-specific expression of the rat insulin gene: evidence for role of two distinct 5' flanking elements;" Science; 1985; pp. 912-916; vol. 230, No. 4728.
Egger et al.; "Reverse transcription multiplex PCR for differentiation between polio-and enteroviruses from clinical and environmental samples." Journal of Clinical Microbiology; Jun. 1995; pp. 1442-1447; vol. 33, No. 6.
Ehrich et al.; "Noninvasive detection of fetal trisomy 21 by sequencing of DNA in maternal blood: a study in a clinical setting;" Reports of Major Impact, American Journal of Obstetrics and Gynecology; Mar. 2011; pp. 205e1-205e11.
Ehrich et al.; A new method of accurate assessment of DNA quality after bisulfite treatment; Nucleic Acids Research; 2007; pp. e29 1-8; vol. 35, No. 5.
Ehrich et al.; "Quantitative high-throughput analysis of DNA methylation patters by base specific cleavage and mass spectrometry;" Proc National Academy of Science U S A; 2005; pp. 15785-15790; vol. 102.
Ehrich et al.; "Cytosine methylation profiling of cancer cell lines;" Proc National Academy Science U S A; 2008; pp. 4844-4848; vol. 105.
Eben et al.; "First-trimester screening: an overview." J Histochem Cytochem; Mar. 2005; pp. 281-283; vol. 53, No. 3.
Ernani et al.; "Agilent's SureSelect Target Enrichment System: Bringing Cost and Process Efficiency to Next-Generation Sequencing Product Note;" Agilent Technologies; Mar. 16, 2009.
EVA and Aaronson; Nature; 1985; pp. 273-275; vol. 316.
European Patent Office Application No. 09815148; Extended Search Report dated Apr. 19, 2012.
Fajkusova et al.: "Detailed Mapping of Methylcytosine Positions at the CpG Island Surrounding the Pa Promoter at the bcr-abl Locus in CML Patients and in Two Cell Lines, K562 and BV173;" Blood Cells Monocyte Disorders; 2000; pp. 193-204; vol. 26, No. 3.
Fan et al.; "Analysis of the size distributions of fetal and maternal cell-free DNA by paired-ending sequencing": Clinical Chemistry; 2010; pp. 1279-1286; vol. 56, No. 8.
Fan et al.; "Noninvasive diagnosis of fetal aneuploidy by shotgun sequencing DNA from maternal blood; " Pro National Academy Science U S A; Oct. 21, 2008; E-pub Oct. 6, 2008; pp. 16266-16271; vol. 105, No. 42.
Fan et al.; "Working Set Selection Using the Second Order Information for Training SVM;" Journal of Machine Learning Research; 2005; pp. 1889-1918, vol. 6.
Feinberg; "Methylation meets genomics;" Nature Genetics; Jan. 2001; pp. 9-10; vol. 27, No. 1.
Ferguson-Smith; "Placental mRNA in maternal plasma: Prospects for fetal screening"; PNAS; Apr. 15, 2003; pp. 4360-4362; vol. 100, No. 8.
Fournie et al.; Analytical Biochemistry; 1986; pp. 250-256; vol. 158.
Frommer et al.; Pro National Academy Science USA; 1992; pp. 1827-1831; vol. 89.
Futreal et al.; Nature Reviews Cancer; 2004; pp. 177-183; vol. 4.
Gardiner-Garden et al.; "CpG islands invertebrate genomes;" Journal Molecular Biology; Jul. 20, 1987; pp. 261-282; vol. 196, No. 2.
Gebhard et al.; "Rapid and sensitive detection of CpG-methylation using methyl-binding(MB)-PCR;" Nucleic Acids Research 2006; p. e82; vol. 34.

(56) References Cited

OTHER PUBLICATIONS

Gebhard et al.; Genomewide profiling of CpG methylation identifies novel targets of aberrant hypermthylation in myeloid leukemia; Cancer Research; 2006; pp. 6118-6128; vol. 66.
Giles et al.; "Acute myeloid leukemia;" Hematology American Society Hematology Education Program; 2002; pp. 73-110.
Go et al.; Clinical Chemistry; Dec. 2007; pp. 2223-2224; vol. 53, No. 12.
Go et al.; "Non-invasive aneuploidy detection using free fetal DNA and RNA in maternal plasma: recent progress and future possibilities"; Human Reproduction Updated; 2011; pp. 372-382; vol. 17, No. 3.
Goeddel; "Gene Expression Technology: Methods in Enzymology;" Academic Press; San Diego, CA., 1990, vol. 185.
Gonzalgo & Jones; Nucleic Acids Research: 1997; pp. 2529-2531; vol. 25.
Gottesman; 'Gene Expression Technology: Methods in Enzymology;' Academic Press; 1990; pp. 119-129; vol. 185; San Diego, California.
Gottesman, "Commentary GABA Mechanisms and Sleep," Neuroscience, 111(2):231-239 (2002).
Grompe et al.; Proc. National Academy Science USA; 1989; pp. 5855-5892; vol. 86.
Grompe; "The rapid detection of unknown mutations in nucleic acids." Nature Genetics; Oct. 1993; pp. 111-117, vol. 5, No. 2.
Grunau et al.; "Bisulfite genomic sequencing: systematic investigation of critical experimental parameters." Nucleic Acids Research; Jul. 2001; pp. E65-5, vol. 29, No. 13.
Gupta et al.; "Use of specific endonuclease cleavage in RNA sequencing." Nucleic Acids Research; Jun. 1977; pp. 1957-1978, vol. 4, No. 6.
H1FOO antibody (K-14) date sheet: sc-9910, www.scbt.com/datasheet-9918-hfloo-k-14-antibody, html, Santa Cruz Biotechnology, 2007-2015.
Haase et al.; Methods in Virology, 1984, pp. 189-226.
Haddow, et al.; "Screening of maternal serum for fetal Down's syndrome in the first trimester"; The New England Journal of Medicine; Apr. 2, 1998; pp. 955-961; vol. 338, No. 14.
Hage & Tweed, Journal of Chromatography B: Biomedical Sciences and Applications; Oct. 10, 1997; pp. 499-525; vol. 699, Nos. 1-2.
Hahn et al.; Placenta, 2011, pp. S17-S20, vol. 32 Supplement.
Hahner et al.; "Matrix-assisted laser desorption/ionization mass spectrometry (MALDI) of endonuclease digests of RNA;" Nucleic Acids Research; May 15, 1997; pp. 1957-1964; vol. 25, No. 10.
Hames and Higgins, eds., Nucleic Acid Hybridization: A Practical Approach; IRL Press; 1985.
Hannish, et al.; "Activity of DNA modification and restriction enzymes in KGB, a potassium glutamate buffer;" Gene Analysis Techniques; 1988; vol. 5, No. 105.
Harris et al.; "Single-molecule DNA sequencing of a viral genome." Science; Apr. 4, 2008; pp. 106-109, vol. 320, No. 5872.
Hart et al.; The Journal Biological Chemistry; 1994; pp. 62-65; vol. 269.
Hasan et al.; Nucleic Acids Research; 1996, pp. 2150-2157, vol. 24.
Heegaard; Journal of Molecular Recognition Winter; 1998; pp. 141-148; vol. 11, Nos. 1-6.
Hennig et al.; Journal of the American Chemical Society; 2007; pp. 14911-14921; vol. 129.
Herman et al.; Proceedings of the National Academy of Sciences of the U S A; 1996; pp. 9821-9826; vol. 93.
Hershey et al.; Journal of Molecular Biology; 1960, pp. 143-152, vol. 2.
Hill; "Gen-Probe Transcription-Mediated Amplification: System Principles;" Jan. 1996; httl://www.gen-probe.com/pdfs/tma_whiteppr.pdf.
HiSeq 2000 Sequencing System Specification Sheet, Illumina INC.; 2010.
Holdenrieder, "Circulating Nucleosomes: A New Addition to the Personalized Medicine Toolkit," Per. Med., 11(6):565-568 (2014).
Holdenrieder et al., "Circulating Nucleosomes Predict the Response to Chemotherapy in Patients with Advanced Non-Small Cell Lung Cancer," Clin. Cancer Res., 10(18):5981-5987 (2004).
Homer, J. et al.; Prenatal Diagnosis; 2003, pp. 566-571, vol. 23.
Hook; Lancet; 1981; pp. 169-172; vol. 2.
Hromandnikova, et al.; "Quantification of Fetal and Total Circulatory DNA in Maternal Plasma Samples Before and After Size Fractionation by Agarose Gel Electrophoresis;" DNA and Cell Biology; 2006, pp. 635-640; vol. 25, No. 11.
Hu et al.; "Aneuploidy detection in single cells using DNA array-based comparative genomic hybridization"; Molecular Human Reproduction; 2004; pp. 283-289; vol. 10.
Hua et al.; "Quantitative methylation analysis of multiples genes using methylationsensitive restriction enzyme-based quantitative PCR for the detection of hepatocellular carcinoma"; Experimental and Molecular Pathology; 2011; pp. 455-460; vol. 91.
Huang et al.; "Mechanism of ribose 2'-group discrimination by an RNA polymerase;" Biochemistry; Jul. 8, 1997; pp. 8231-8242; vol. 36, No. 27.
Hulten et al.; "Rapid and simple prenatal diagnosis of common chromosome disorders: advantages and disadvantages of the molecular methods FISH and QF-PCR;" Reproduction; Sep. 2003; pp. 279-297; vol. 126, No. 3.
Hunkapiller et al.; "A microchemical facility for the analysis and synthesis of genes and proteins;" Nature; Jul. 12-18, 1984; pp. 105-111; vol. 310, No. 5973.
Hyrup et al.; "Peptide nucleic acids (PNA): synthesis, properties and potential applications;" Bioorganic & Medicinal Chemistry; Jan. 1996; pp. 5-23, vol. 4, No. 1.
Imai et al.; Journal of Virological Methods; 1992; pp. 181-184; vol. 36.
Imamura et al.; "Prenatal diagnosis of adrenoleukodystrophy by means of mutation analysis." Prenatal Diagnosis; Mar. 1996; pp. 259-261, vol. 16, No. 3.
Innis et al.; PCR Protocols: A Guide to Methods and Applications, Innis et al., eds.; 1990.
ISSA.; "CpG island methylator phenotype in cancer;" Nature Reviews Cancer; Dec. 2004; pp. 988-993, vol. 4, No. 12.
Iverson et al.; Prenatal Diagnosis; 1981; pp. 31-48; vol. 9.
Iwabuchi et al.; Oncogene, 1993, pp. 1693-1696, vol. 8.
Jing et al.; Proceedings of the National Academy of Sciences of the U S A; 1998; pp. 8046-8051; vol. 95, No. 14.
Johansen et al.; "An investigation of methods for enriching trophoblast from maternal blood;" Prenatal Diagnosis; Oct. 1995; pp. 921-931; vol. 15, No. 10.
Jurinke, et al.; "MALDI-TOF mass spectrometry: a versatile tool for high-performance DNA analysis;" Molecular Biotechnology; 2004, pp. 147-164; vol. 26.
Kalinina et al.; "Nanoliter scale PCR with TaqMan detection;" Nucleic Acids Research; May 15, 1997; pp. 1999-2004; vol. 25, No. 10.
Kaneko et al.; Gut; 2003; pp. 641-646; vol. 52.
Karlin et al.; "Methods for assessing the statistical significance of molecular sequence features by using general scoring schemes;" Proceedings of the National Academy of Sciences of the U S A; Mar. 1990; pp. 2264-2268, vol. 87, No. 6.
Kent; "BLAT—the BLAST-like alignment tool;" Genome Research; Apr. 2002; pp. 656-664, vol. 12, No. 4.
Kessel et al.; "Murine developmental control genes;" Science; Jul. 27, 1990; pp. 374-379, vol. 249, No. 4967.
Kidd et al.; "Mapping and sequencing of structural variation from eight human genomes;" Nature; May 1, 2008; pp. 56-64; vol. 453, No. 7191.
Kitzman et al.; "Noninvasive Whole-Genome Sequencing of a Human Fetus"; Science Translation Medicine; 2012; pp. 115-122; vol. 4, No. 137.
Kriegler; Gene Transfer and Expression: A Laboratory Manual (1990).
Kristensen et al.; "PCR-Based Methods for Detecting Single-Locus DNA Methylation Biomarkers in Cancer Diagnostics, Prognostics, and Response to Treatment;" Clinical Chemistry; Washington DC; Aug. 1, 2009; pp. 1471-1483; vol. 55, No. 8.

(56) References Cited

OTHER PUBLICATIONS

Kuchino et al.; "Enzymatic RNA sequencing"; Methods in Enzymology; 1989; pp. 154-163; vol. 180.
Kuhn et al.; "DNA Helicases"; Cold Spring Harbor Symposia Quantitative Biology; 1979; pp. 63-67; vol. 43, Pt 1.
Kulkarmi et al.; "Global DNA methylation patterns in placenta and its association with maternal hypertension in pre-eclampsia"; DNA Cell Biology; 2011; pp. 79-84; vol. 30, No. 2.
Kumps et al.; "RMeseuarlcthi aprtilcelex Amplicon Quantification (MAQ), a fast and efficient method for the simultaneous detection of copy number alterations in neuroblastoma"; BMC Genomics; 2010; pp. 1-10; vol. 11, No. 298.
Lai et al.; Nature Genetics; 1999; pp. 309-313; vol. 23, No. 3.
Laird; Nature Reviews Cancer; 2003; pp. 253-266, vol. 3.
Larkin et al.; "Clustal W and Clustal X version 2.0;" Bioinformatics; Nov. 1, 2007; Epub Sep. 10, 2007; pp. 2947-2948; vol. 23, No. 21.
Lee et al.; "Fetal Nucleic Acids in Maternal Plasma"; Fetal and Maternal Medicine Review; 2006; pp. 125-137; vol. 17, No. 2.
Lee et al.; "Control of developmental regulators by Poly comb in human embryonic stem cells"; Cell; 2006; pp. 301-313; vol. 125.
Leung et al.; "An efficient algorithm for identifying matches with errors in multiple long molecular sequences"; Journal of Molecular Biology; Oct. 20, 1991; pp. 1367-1378; vol. 221, No. 4.
Li et al.; Nucleic Acids Research; 1995, pp. 4495-4501, vol. 23.
Li et al.; "Dynamic Distribution of Linker Histone H1.5 in Cellular Differentiation"; PLOS Genetics; Aug. 2012; pp. 1-13; vol. 8 No. 8; e1002879.
Li et al.; "Size separation of circulatory DNA in maternal plasma permits ready detection of fetal DNA polymorphisms"; Clinical Chemistry; Jun. 2004; Epub. Apr. 8, 2004; pp. 1002-1011; vol. 50, No. 6.
Li et al.; "Targeted mutation of the DNA methyltransferase gene results in embryonic lethality"; Cell; Jun. 12, 1992; pp. 915-926; vol. 69, No. 6.
Li et al.; "Genotyping fetal paternally inherited SNPs by MALDI-TOF MS using cell-free fetal DNA in maternal plasma: Influence of size fractionation"; Electrophoresis; 2006; pp. 3889-3896; vol. 27.
Lingbeek; Cell; 2004; pp. 409-418; vol. 118.
Little, et al.; Nature Medicine; 1997; pp. 1413-1416; vol. 3.
Litz et al.; "Methylation status of the major breakpoint cluster region in Philadelphia chromosome negative leukemias"; Leukemia 1992; pp. 35-41; vol. 6, No. 1.
Liu et al.; "Quantification of regional DNA methylation by liquid chromatography/tandem mass spectrometry"; Analytical Biochemistry, Academic Press Inc., New York; Aug. 15, 2009; pp. 106-113, vol. 391, No. 2.
Liu et al.; "The ribosomal small-subunit protein S28 gene from *Helianthus annuus* (asteraceae) is down-regulated in response to drought, high salinity, and abscisic acid"; American Journal of Botany; Apr. 1, 2003; pp. 526-531; vol. 90, No. 4.
Lo et al.; Nature Medicine; Feb. 2007; pp. 218-223; vol. 13, No. 2.
Lo et al.; "Maternal Plasma DNA Sequencing Reveals the Genome-Wide Genetic and Mutational Profile of the Fetus"; Prenatal Diagnosis, Science Translational Medicine; Dec. 8, 2010, pp. 1-13; vol. 2, No. 61.
Lo et al.; "Presence of fetal DNA in maternal plasma and serum"; Lancet; Aug. 16, 1997; pp. 485-487; vol. 350, No. 9076.
Lo et al.; "Quantitative analysis of fetal DNA in maternal plasma and serum: implications for noninvasive prenatal diagnosis"; American Journal of Human Genetics; Apr. 1998; pp. 768-775; vol. 62, No. 4.
Lo et al.; Clinical Chemistry; 1999; pp. 1747-1751, vol. 45.
Lo et al.; Clinical Chemistry; 1999; pp. 184-188; vol. 45.
Lo et al.; The New England Journal of Medicine 1998; pp. 1734-1738; vol. 339.
Lo et al.; Prenatal diagnosis: progress through plasma nucleic acids; Nature Reviews Genetics; 2007; pp. 71-77; vol. 8.

Lo; "Recent advances in fetal nucleic acids in maternal plasma"; Journal of Histochemistry & Cytochemistry; Mar. 2005; pp. 293-296; vol. 53, No. 3.
Lun et al.; "Microfluidics digital PCR reveals a higher than expected fraction of fetal DNA in maternal plasma"; Clinical Chemistry; Oct. 2008; Epub Aug. 14, 2008; pp. 1664-1672; vol. 54, No. 10.
Lun et al.; "Noninvasive prenatal diagnosis of monogenic diseases by digital size selection and relative mutation dosage on DNA in maternal plasma"; PNAS; Dec. 16, 2008; pp. 19920-19925; vol. 105, No. 50.
Madura et al.; Journal of Biological Chemistry; 1993; pp. 12046-12054; vol. 268.
Majlessi et al.; Nucleic Acids Research; 1998; pp. 2224-2229; vol. 26, No. 9.
Malik et al.; "Polyethylene glycol (PEG)-modified granulocyte-macrophage colony-stimulating factor (GM-CSF) with conserved biological activity"; Experimental Hematology; Sep. 1992; pp. 1028-1035; vol. 20, No. 8.
Mann et al.; "Development and implementation of a new rapid aneuploidy diagnostic service within the UK National Health Service and implications for the future of prenatal diagnosis"; Lancet; Sep. 29, 2001; pp. 1057-1061; vol. 358, No. 9287.
Mann; Methods in Molecular Medicine; 2004; pp. 141-156, vol. 92.
Mao and Williamson; Nucleic Acids Research; 1999; pp. 4059-4070; vol. 27.
Marais et al.; The EMBO Journal; 1995; pp. 3136-3145, vol. 14.
Marais et al.; Journal of Biological Chemistry; 1997, pp. 4378-4383; vol. 272.
Margulies et al.; "Genome sequencing in microfabricated high-density picolitre reactors"; Nature; Sep. 15, 2005; Jul. 31, Epub 2005; pp. 376-380; vol. 437, No. 7057.
Mason et al.; The EMBO Journal; 1999; pp. 2137-2148; vol. 18.
McClelland et al.; "A single buffer for all restriction endonucleases"; Nucleic Acids Research; 1988; p. 364; vol. 16.
McConnell et al.; Science; 1992; pp. 1906-1912; vol. 257.
Meller; Clinical Chemistry; 2007; pp. 1996-2001; vol. 53.
Metzker; Nature Reviews; 2010; pp. 31-46, vol. 11.
Meyers & Miller; Canadian Associates of BIOS;1989; pp. 11-17; vol. 4.
Millipore; QIA25 Nucleosome ELISA Kit, Information Brochure, Calbiochem; Feb. 26, 2013.
Mito et al.; Nature Genetics; 2005; pp. 1090-1097; vol. 37.
John Wiley & Sons, Inc., Molecular Cloning of PCR Products, Unit 15.4; Current Protocols in Molecular Biology; 2001; vol. 15.4.1-15.4.11, Supplement 56.
Moudrianakis et al.; Proceedings of the National Academy of Sciences of the U S A; Mar. 1965; pp. 564-571; vol. 53.
Mouliere et al.; "High Fragmentation Characterizes Tumour-Derived Circulating DNA"; PLoS ONE; Sep. 2011; pp. 1-10, vol. 6, No. 9; e23438.
Nakamaye et al.; Nucleic Acids Research; 1988; pp. 9947-9959; vol. 23.
Nakano et al.; "Single-molecule PCR using water-in-oil emulsion"; Journal of Biotechnology; 2003; pp. 117-124; vol. 102.
NCBI dbSNP cluster report record for rs16139, accessed Sep. 16, 2013.
Needham-Vandevanter et al.; "Characterization of an adduct between CC-1065 and a defined oligodeoxynucleotide duplex." Nucleic Acids Research; Aug. 10, 1984; pp. 6159-6168; vol. 12, No. 15.
Needleman et al.; "A general method applicable to the search for similarities in the amino acid sequence of two proteins"; Journal of Molecular Biology; Mar. 1970; pp. 444-453; vol. 48, No. 3.
Ng et al.; Proceedings of the National Academy of Sciences of the U S A; 2003; pp. 4748-4753; vol. 100.
Ng et al.; Clinical Chemistry; 2002; pp. 1212-1217; vol. 48.
Nicolaides et al.; "One-stop clinic for assessment of risk of chromosomal defects at 12 weeks of gestation"; The Journal of Maternal-Fetal & Neonatal Medicine; Jul. 2002; pp. 9-18; vol. 12, No. 1.
Nicolaides et al.; Prenatal Diagnosis; 2002; pp. 308-315; vol. 22.
Nicolaidis et al.; "Origin and mechanisms of non-disjunction in human autosomal trisomies"; Human Reproduction ; Feb. 1998, pp. 313-319; vol. 13, No. 2.

(56) References Cited

OTHER PUBLICATIONS

Nishizuka et al.; "Proteomic profiling of the NCI-60 cancer cell lines using new high-density reverse-phase lysate microarrays." Proceedings of the National Academy of Sciences of the U SA ; Nov. 25, 2003; Epub Nov. 17, 2003; pp. 14229-14234; vol. 100, No. 24.

Nolte; "Branched DNA signal amplification for direct quantitation of nucleic acid sequences in clinical specimens"; Advances in Clinical Chemistry; 1998; pp. 201-235; vol. 33.

Nosaka et al.; "Increasing methylation of the CDKN2A gene is associated with the progression of adult T-cell leukemia"; Cancer Research; 2000; pp. 1043-1048; vol. 60, No. 4.

Nygren et al.; "Quantification of Fetal DNA by Use of Methylation-Based DNA Discrimination"; Clinical Chemistry; pp. 1627-1635; vol. 56, No. 10 (2010).

Oefner et al.; "Efficient random subcloning of DNA sheared in a recirculating point-sink flow system"; Nucleic Acids Research; 1996; pp. 3879-3886; vol. 24, No. 20.

Oeth et al.; "Qualitative and quantitative genotyping using single base primer extension coupled with matrix-assisted laser desorption/ionization time-of-flight mass spectrometry (MassARRAY)"; Methods in Molecular Biology; 2009; pp. 307-343; vol. 578.

Oeth et al.; (iPLEX™ Assay: Increased Plexing Efficiency and Flexibility for MassARRAY® System through single base primer extension with mass-modified Terminators; SEQUENOM Application Note; 2005.

Ohm et al.; "A stem cell-like chromatin pattern may predispose tumor suppressor genes to DNA hypermethylation and heritable silencing"; Nature Genetics; 2007; pp. 237-242; vol. 39.

Ohtsuka et al.; Journal of Biological Chemistry; 1985; pp. 2605-2608; vol. 260.

Okano et al., "DNA methyltransferases Dnmt3a and Dnmt3b are essential for de novo methylation and mammalian development;" Cell; Oct. 1999; pp. 247-257; vol. 99, No. 3.

Old; "Candidate epigenetic biomarkers for non-invasive prenatal diagnosis of Down syndrome"; Reproductive BioMedicine Online; 2007; pp. 227-235; vol. 15, No. 2.

Olek et al.; "A modified and improved method for bisulphite based cytosine methylation analysis"; Nucleic Acids Research; Dec. 15, 1996; pp. 5064-5066; vol. 24, No. 24.

Oligonucleotides and Analogues, A Practical Approach; F. Eckstein, editor; IRL Press, Oxford; 1991.

Orita et al.; Proceedings of the National Academy of Sciences of the U S A; 1989; pp. 27776-2770, vol. 86.

Osborne et al.; Current Opinion in Chemical Biology; 1997; pp. 5-9; vol. 1, No. 1.

Oudejans et al.; Prenatal Diagnosis; 2003; pp. 111-116, vol. 23.

Padilla et al.; "Efficient synthesis of nucleic acids heavily modified with non-canonical ribose 2'-groups using a mutantT7 RNA polymerase (RNAP)"; Nucleic Acids Research; Mar. 15, 1999; pp. 1561-1563; vol. 27, No. 6.

Palomaki et al.; "Maternal serum screening for Down syndrome in the United States: a 1995 survey"; American Journal of Obstetrics & Gynecology; May 1997; pp. 1046-1051; vol. 176, No. 5.

Pandya et al.; "Screening for fetal trisomies by maternal age and fetal nuchal translucency thickness at 10 to 14 weeks of gestation" British Journal of Obstetrics and Gynaecology; Dec. 1995; pp. 957-962; vol. 102, No. 12.

Patel; Current Opinion in Chemical Biology; Jun. 1997; pp. 32-46; vol. 1, No. 1.

Paulin et al.; Nucleic Acids Research; 1998; pp. 5009-5010; vol. 26.

Pearson & Reanier; Journal of Chromatography; 1983; pp. 137-149, vol. 255.

Pearson; Proceedings of the National Academy of Sciences of the U S A; 1988; pp. 2444-2448; vol. 85, No. 5.

Perry-O'Keefe et al. "Peptide nucleic acid pre-gel hybridization: an alternative to southern hybridization"; Proceedings of the National Academy of Sciences of the U S A; Dec. 10, 1996; pp. 14670-01475; vol. 93, No. 25.

Pertl et al.; "Rapid molecular method for prenatal detection of Down's syndrome"; Lancet; May 14, 1994; pp. 1197-1198; vol. 343, No. 8907.

Peters et al.; "Noninvasive Prenatal Diagnosis of a Fetal Microdeletion Syndrome"; New England Journal of Medicine; Nov. 10, 2011; pp. 1847-1848.

Petersen and Mikkelsen; Cytogenetics and Cell Genetics; 2000; pp. 199-203; vol. 91, Nos. 1-4.

Pinkert et al.; Genes & Development; 1987; pp. 268-277, vol. 1.

Poon et al.; Clinical Chemistry; 2000; pp. 1832-1834; vol. 46.

Poon et al.; "Differential DNA methylation between fetus and mother as a strategy for detecting fetal DNA in maternal plasma"; Clinical Chemistry; Jan. 2002; pp. 35-41; vol. 48, No. 1.

Porter et al.; Biochemistry; 1995; pp. 11963-11969; vol. 34 .

QU et al.; "Analysis of drug-DNA binding data"; Methods in Enzymology; 2000; pp. 353-369; vol. 321.

Queen et al.; "Immunoglobulin gene transcription is activated by downstream sequence elements"; Cell; Jul. 1983; pp. 741-748; vol. 33, No. 3.

Radding; "Homologous pairing and strand exchange in genetic recombination"; Annual Review of Genetics; 1982; pp. 405-437; vol. 16.

Randen et al.; "Prenatal genotyping of RHD and SRY using maternal blood"; Vox Sanguinis; Nov. 2003, pp. 300-306; vol. 85, No. 4.

Rashtchian; PCR Methods and Applications; 1994; pp. S83-S91; vol. 4.

Rivas et al.; Trends in Biochemical Sciences; Aug. 1993; pp. 284-287; vol. 18, No. 8.

Robertson et al.; Nature Reviews Genetics; 2000; pp. 11-19; vol. 1.

Roach et al.; "Association between the abnormal expression of matrix-degrading enzymes by human osteoarthritic chondrocytes and demethylation of specific CpG sites in the promoter regions"; Arthritis & Rheumatism; 2005; pp. 3110-3124; vol. 52, No. 10.

Robinson et al.; "A comparison of Affymetrix gene expression arrays"; BMC Bioinformatics; 2007; p. 449; vol. 8.

Rojo et al. "Cusativin, a new cytidine-specific ribonuclease accumulated in seeds of *Cucumis sativus* L"; Planta.; 1994; pp. 328-338; vol. 194, No. 3.

Rollins et al.; "Large-scale structure of genomic methylation patterns"; Genome Research; Feb. 2006; Epub Dec. 19, 2005; pp. 157-163; vol. 16, No. 2.

Romero and Rotbard; Diagnostic Molecular Biology: Principles and Applications; Pershing et al. eds.; Mayo Foundation, Rochester, Minn.; 1993; pp. 401-406.

Roschke et al.; "Karyotypic complexity of the NCI-60 drug-screening panel"; Cancer Research; Dec. 15, 2003; pp. 8634-8647; vol. 63, No. 24.

Rosenberg et al.; Journal of the American Chemical Society; 1960; pp. 3198-3201; vol. 82.

Rossolini et al.; Mol. Cell. Probes; 1994; pp. 91-98; vol. 8.

Sadri & Hornsby; Nucleic Acids Research; 1996; pp. 5058-5059; vol. 24.

Saito et al.; Lancet; 2000; p. 1170; vol. 356.

Salgame et al.; "An ELISA for detection of apoptosis"; Nucleic Acids Research; 1997; pp. 680-681; vol. 25, No. 3.

Sambrook and Russell; Molecular Cloning, A Laboratory Manual; 3rd edition; 2001.

Sambrook et al.; Molecular Biology: A laboratory Approach; Cold Spring Harbor, N. Y.; 1989.

Sanchez et al.; "Effects of Sulpiride on Prolactin and mRNA Levels of Steroid 5a-reductase Isozymes in Adult Rat Brain"; Neurochemical Research; 2008; pp. 820-825; vol. 33.

Sancho, M. et al., "Depletion of Human Histone H1 Variants Uncovers Specific Roles in Gene Expression and Cell Growth," PLoS Genet. 4(10):e1000227 (2008) 17 pages.

Santoro et al.; "A general purpose RNA-cleaving DNA enzyme"; Proceedings of the National Academy of Sciences of the U S A; 1997; pp. 4262-4266; vol. 94.

Sargent et al.; Methods in Enzymology; 1988; p. 432; vol. 152.

Sayres et al.; "Cell-free fetal nucleic acid testing: A review of the technology and its applications"; Obstetrical and Gynecological Survey; 2011; pp. 431-442; vol. 66, No. 7.

(56) References Cited

OTHER PUBLICATIONS

Schlesinger et al.; "Polycomb-mediated methylation on Ly s27 of histone H3 pre-marks genes for de novo methylation in cancer"; Nature Genetics; Feb. 2007; Epub Dec. 31, 2006; pp. 232-236; vol. 39, No. 2.

Schouten et al.; "Relative quantification of 40 nucleic acid sequences by multiplex ligation-dependent probe amplification"; Nucleic Acids Research; Jun. 15, 2002; p. e57, vol. 30, No. 12.

Schriefer et al.; "Low pressure DNA shearing: a method for random DNA sequence analysis"; Nucleic Acids Research; 1990; pp. 7455-7456; vol. 18.

Schuler; Sequence mapping by electronic PCR; Genome Research; May 1997; pp. 541-550, vol. 7, No. 5.

Schwartzentruber, J. et al., "Driver mutations in histone H3.3 and chromatin remodelling genes in paediatric glioblastoma," Nature 482:226-232 (2012).

Scott et al.; Journal of the American Chemical Society; 2004; pp. 11776-11777; vol. 126.

Sekizawa et al., Clinical Chemistry; 2001; pp. 2164-2165; vol. 47.

Sharma et al.; "Mass spectrometric based analysis, characterization and applications of circulating cell free DNA isolated from human body fluids"; International Journal of Mass Spectrometry; 2011; pp. 172-183; vol. 304.

Sheffield et al.; "Identification of novel rhodopsin mutations associated with retinitis pigmentosa by GC-clamped denaturing gradient gel electrophoresis"; American Journal of Human Genetics; Oct. 1993; pp. 699-706; vol. 49, No. 4.

Silverman et al.; "Methylation inhibitor therapy in the treatment of myelodysplastic syndrome"; Nature Clinical Practice Oncology; Dec. 2005; pp. S12-S23; vol. 2, Supplement 1.

Simoncsits et al.; "New rapid gel sequencing method for RNA"; Nature; Oct. 27, 1977; pp. 833-836; vol. 269, No. 5631.

Singer et al.; Biotechniques; 1986; p. 230; vol. 4.

Sjolander & Urbaniczk; Analytical Chemistry; 1991; pp. 2338-2345; vol. 63.

Slater et al.; "Rapid, high throughput prenatal detection of aneuploidy using a novel quantitative method (MLPA)"; Journal Medical Genetics; Dec. 2003; pp. 907-912; vol. 40, No. 12.

Smith et al.; "Identification of common molecular subsequences"; Journal of Molecular Biology; Mar. 25, 1981; pp. 195-197; vol. 147, No. 1.

Smith et al.; "Single-step purification of polypeptides expressed in *Escherichia coli* as fusions with glutathione S-transferase"; Genetics; Jul. 15, 1988; pp. 31-40; vol. 67, No. 1.

Snijders et al.; "Assembly of microarrays for genome-wide measurement of DNA copy number"; Nature Genetics; Nov. 2001; pp. 263-264; vol. 29, No. 3.

Snijders et al.; "First-trimester ultrasound screening for chromosomal defects"; Ultrasound in Obstetrics & Gynecology; Mar. 1996; pp. 216-226; vol. 7, No. 3.

Snijders et al.; "UK multicentre project on assessment of risk of trisomy 21 by maternal age and fetal nuchal-translucency thickness at 10-14 weeks of gestation. Fetal Medicine Foundation First Trimester Screening Group"; Lancet; Aug. 1, 1998; pp. 343-346; vol. 352, No. 9125.

Soni et al.; "Progress toward ultrafast DNA sequencing using solid-state nanopores"; Clinical Chemistry; Nov. 2007; Epub Sep. 21, 2007; pp. 1996-2001; vol. 53, No. 11.

Sousa et al.; "A mutant T7 RNA polymerase as a DNA polymerase"; The EMBO Journal; Sep. 15, 1995; pp. 4609-4621; vol. 14, No. 18.

Spetzler et al.; Enriching for Rare Subpopulations of Circulating Microvesicles by the Depletion of Endothelial-and Leukocyte-Derived Microvesicles; CARIS Life Sciences, Carisome Posters, Papers, Abstracts and Presentations, American Academy of Cancer Research (AACR 2011).

Stanssens et al.; "High-throughput MALDI-TOF discovery of genomic sequence polymorphisms"; Genome Research; Jan. 2004; pp. 126-133; vol. 14, No. 1.

Staunton et al.; "Chemosensitivity prediction by transcriptional profiling"; Proceedings of the National Academy of Sciences of the U S A; Sep. 11, 2001; pp. 10787-10792; vol. 98, No. 19.

Strathdee, et al.; American Journal of Pathology; 2001; pp. 1121-1127; vol. 158.

Strohmeier; "A New High-Performance Capillary Electrophoresis Instrument"; Hewlett-Packard Journal; Jun. 1995; pp. 10-19.

Szabo et al.; Current Opinion in Structural Biology; 1995; pp. 699-705; vol. 5.

Tabor et al.; "Non-Invasive Fetal Genome Sequencing: Opportunities and Challenges"; American Journal of Medical Genetics Part A; 2012; pp. 2382-2384; vol. 158A, No. 10.

Takai et al.; Proceedings of the National Academy of Sciences of the U SA; 2002; pp. 3740-3745; vol. 99.

Tang et al.; Analytical Chemistry; 2002; pp. 226-331; vol. 74.

Terme et al.; "Histone H1 Variants Are Differentially Expressed and Incorporated into Chromatin during Differentiation and Reprogramming to Pluripotency"; The Journal of Clinical Chemistry; Oct. 14, 2011; pp. 35347-35357; vol. 286, No. 41.

The Cancer Test, Cell Free DNA; 2007; Health Screen Inc. printed from the Internet on Mar. 20, 2011 (http://www.thecancertest.com/science-of-cell-free-dna/).

T. Strachan; The Human Genome; BIOS Scientific Publishers; 1992.

The World Health Organization histological typing of lung tumours; American Journal Clinical Pathology; 1982; pp. 123-136; vol. 77.

Thorstenson et al.; "An Automated Hydrodynamic Process for Controlled, Unbiased DNA Shearing"; Genome Research; 1998; pp. 848-855; vol. 8.

Tolbert and Williamson; Journal of the American Chemical Society; 1996; pp. 7929-7940; vol. 118.

Tolbert and Williamson; Journal of the American Chemical Society; 1997; pp. 12100-12108; vol. 119.

Tong et al.; "Noninvasive Prenatal Detection of Fetal Trisomy 18 by Epigenetic Allelic Ratio Analysis in Maternal Plasma: Theoretical and Empirical Considerations"; Clinical Chemistry; pp. 2149-2202; vol. 52, No. 12.

Tooke, et al.; VDT; Nov. 2004; vol. 41.

Tost et al.; Nucleic Acids Research; 2003; p. e50; vol. 37.

Toyota et al.; "Methylation profiling in acute myeloid leukemia"; Blood; May 1, 2001; pp. 2823-2829; vol. 97, No. 9.

Toyota et al.; Cancer Research; 1999; pp. 2307-2312; vol. 59.

Tsui et al.; "Systemic Identification of Placental Epigenetic Signatures for the Noninvasive Prenatal Detection of Edwards Syndrome" PLOS One; 2010; . e15069; vol. 5, No. 11.

Tungwiwat et al.; "Non-invasive fetal sex determination using a conventional nested PCR analysis of fetal DNA in maternal plasma"; Clinica Chimica Acta; Aug. 2003; pp. 173-177; vol. 334, Nos. 1-2.

Tynan et al.; "Fractional DNA quantification by massively parallel shotgun sequencing-implications for fetal fraction measurement in maternal plasma"; (Sequenom MME) ASHG Poster, 2011.

Uhlmann et al.; Electrophoresis; 2002; pp. 4072-4079; vol. 23.

Valk et al.;"Prognostically useful gene-expression profiles in acute myeloid leukemia"; The New England Journal of Medicine; Apr. 15, 2004; pp. 1617-1628; vol. 350, No. 16.

Valk-Lingbeek et al.; "Stem cells and cancer; the polycomb connection"; Cell; Aug. 20, 2004; pp. 409-418; vol. 118, No. 4.

Van Der Schoot et al.; Real-time PCR of bi-allelic insertion/deletion polymorphisms can serve as a reliable positive control for cell-free fetal DNA in non-invasive prenatal genotyping [abstract]; Blood; 2003; vol. 102, No. 93a.

Veltman et al.; "High-throughput analysis of subtelomeric chromosome rearrangements by use of array-based comparative genomic hybridization"; American Journal of Human Genetics; May 2002, Epub Apr. 9, 2002; pp. 1269-1276; vol. 70, No. 5.

Venter et al.; "The sequence of the human genome"; Science; Feb. 16, 2001; pp. 1304-1351; vol. 291, No. 5507.

Verbeck et al.; Journal of Biomolecular Techniques; pp. 56-61, vol. 13, No. 2.

Verma et al.; "Rapid and simple prenatal DNA diagnosis of Down's syndrome"; Lancet; Jul. 4, 1998; pp. 9-12; vol. 352, No. 9121.

Vincenet et al.; "Helicase-Dependent isothermal DNA Amplification";EMBO reports; 2004; pp. 795-800; vol. 5, No. 8.

(56) References Cited

OTHER PUBLICATIONS

Vire et al.; "The Polycomb group protein EZH2 directly controls DNA methylation"; Nature; Feb. 16, 2006 ; Epub Dec. 14, 2005; pp. 871-874; vol. 439, No. 7078.
Vogelstein et al.; "Digital PCR"; Proceedings of the National Academy of Sciences of the U S A; Aug. 3, 1999 ; pp. 9236-9241; vol. 96, No. 16.
Volkerding et al.; Clinical Chemistry; 2009; pp. 641-658; vol. 55.
Vu et al.; "Symmetric and asymmetric DNA methylation in the human IGF2-H19 imprinted region"; Genomics; Mar. 1, 2000; pp. 132-143; vol. 64, No. 2.
Wada et al.; "Codon usage tabulated from the GenBank genetic sequence data"; Nucleic Acids Research; May 11, 1992; pp. 11-18; vol. 20, Supplement 21.
Wald and Hackshaw; Prenatal Diagnosis; 1997; pp. 821-829; vol. 17, No. 9.
Wang et al.; BMC Genomics; 2006; p. 166, vol. 7.
Wapner et al.; "First-trimester screening for trisomies 21 and 18"; The New England Journal of Medicine; Oct. 9, 2003; p. 1405-1413; vol. 349, No. 15.
Waterman et al.; Journal of Molecular Biology; 1980; pp. 195-197; vol. 147.
Weber et al.; Oncogene; 2000; pp. 169-176; vol. 19.
Weisenberger. et al.; Nature Genetics; 2006; pp. 787-793; vol. 38.
Weiss et al.; "H1 variant-specific lysine methylation by G9a/KMT1C and GIp1/KMT1 D"; Epigenetics & Chromatin; Mar. 24, 2010; pp. 1-13; vol. 3, No. 7.
White et al.; "Detecting single base substitutions as heteroduplex polymorphisms"; Genomics; Feb. 1992; pp. 301-306; vol. 12, No. 2.
Widschwendier et al.; "Epigenetic stem cell signature in cancer"; Nature Genetics; 2007; pp. 157-158; vol. 39.
Wilkinson; In situ Hybridization; Wilkinson ed.; IRL Press, Oxford University Press, Oxford; 1998.
Winoto et al.; "A novel, inducible and T cell-specific enhancer located at the 3' end of the T cell receptor alpha locus"; The EMBO Journal; Mar. 1989 ; pp. 729-733; vol. 8, No. 3.
Xiong & Laird; Nucleic Acids Research; 1997; pp. 2532-2534; vol. 25.
Yamada et al.; Genome Research; 2004; pp. 247-266; vol. 14.
Yamada et al.; "Suppressive effect of epigallocatechin gallate (EGCg) on DNA methylation in mice: Detection my methylation sensitive restriction endonuclease digestion and PCR"; Journal of Food, Agriculture & Environment; 2005; pp. 73-76; vol. 3, No. 2.
Yan et al.; "A novel diagnostic strategy for trisomy 21 using short tandem repeats"; Electrophoresis; 2006; pp. 416-422; vol. 27.
Zahra et al.; "Plasma microparticles are not elevated in fresh plasma from patients with gynaecologicalmalignancy—An observational study"; Gynecologic Oncology; Oct. 2011; pp. 152-156; vol. 123, No. 1.
Zervos et al.; Cell; 1993; pp. 223-232; vol. 72.
Zhang et al.; "Histone H1 Depletion Impairs Embryonic Stem Cell Differentiation"; PLOS Genetics; May 2012; pp. 1-14; vol. 8, No. 5; e1002691.
Zhao et al.; Pretat Diagnosis; 2010; pp. 778-782; vol. 30, No. 8.
Zheng et al.; "Nonhematopoietically Derived DNA Is Shorter than Hematopoietically Derived DNA in Plasma: A Transplantation Model"; Clinical Chemistry; Nov. 3, 2011; vol. 58, No. 2.
Zhong et al.; American Journal of Obstetrics & Gynecology; 2001; pp. 414-419; vol. 184.
Zhong et al.; Prenat. Diagnosis; 2000; pp. 795-798; vol. 20.
Zimmermann Lecturer, et al.; Serum parameters and nuchal trans-lucency in first trimester screening for fetal chromosomal abnormalities; In: BJOG: An International Journal of Obstetrics & Gynaecology; 1996; pp. 1009-1014; vol. 103, No. 10.
Zimmermann, B. et al.; Clinical Chemistry; 2002; pp. 362-363; vol. 48.
Zuker; "Mfoldweb server for nucleic acid folding and hybridization prediction"; Nucleic Acids Research; pp. 3406-3415; vol. 31, No. 13 (2003).

Supplementary European Search Report dated: Jul. 14, 2011 for European Application No. EP 09720284 filed: Mar. 10, 2009 based on international application No. PCT/US2009/036683.
Extended European Search Report dated Jan. 4, 2012 in European Application No. EP10817598.5 filed: Mar. 18, 2010.
Extended European Search Report dated Apr. 22, 2013 in European Application No. EP10843520 filed: Dec. 20, 2010 based on International Application No. PCT/US2010/061319.
International Preliminary Report on Patentability dated: Sep. 3, 2009 in International Application No. PCT/US2008/54468 filed on Feb. 20, 2008.
International Search Report and Written Opinion dated: Sep. 23, 2008 in International Application No. PCT/US2008/54468 filed on Feb. 20, 2008.
International Preliminary Report on Patentability dated: Feb. 18, 2010 in International Application No. PCT/US2008/54470 filed on Feb. 20, 2008.
International Search Report and Written Opinion dated: Aug. 18, 2008 in International Application No. PCT/US2008/54470 filed on Feb. 20, 2008.
International Preliminary Report on Patentability dated: Dec. 30, 2009 in International Application No. PCT/US2008/066791 filed on Jun. 12, 2008.
International Search Report and Written Opinion dated: Dec. 22, 2008 in International Application No. PCT/US2008/066791 filed on Jun. 12, 2008.
International Search Report and Written Opinion, dated Feb. 24, 2010 in International application No. PCT/US2009/036683 filed on: Mar. 10, 2009 and published as WO 09/114543 dated Sep. 17, 2009.
Invitation to Pay Additional Fees and Partial International Search Report dated Dec. 28, 2009 in International application No. PCT/US2009/036683 filed on: Mar. 10, 2009 and published as WO 09/114543 dated Sep. 17, 2009.
International Preliminary Report on Patentability, dated Sep. 23, 2010 in International application No. PCT/US2009/036683 filed on: Mar. 10, 2009 and published as WO 09/114543 dated Sep. 17, 2009.
International Preliminary Report on Patentability dated Mar. 31, 2011 in International Application No. PCT/US2009/057215 filed on Sep. 16, 2009 and published as: WO 10/033639 dated Mar. 25, 2010.
International Search Report and Written Opinion dated Dec. 29, 2010 in International Application No. PCT/US2009/057215 filed on Sep. 16, 2009 and published as: WO 10/033639 dated Mar. 25, 2010.
International Search Report and Written Opinion dated Dec. 30, 2010 in International Application No. PCT/US2010/027879 filed on Mar. 18, 2010.
International Preliminary Report on Patentability dated: Mar. 29, 2012 in International Application No. PCT/US2010/027879 filed on Mar. 18, 2010.
International Preliminary Report on Patentability dated: Jul. 5, 2012 in International Application No. PCT/US2010/061319 filed on Dec. 20, 2010.
International Search Report and Written Opinion dated: Sep. 21, 2011 in International Application No. PCT/US2010/061319 filed on Dec. 20, 2010.
International Search Report and Written Opinion dated: Jan. 10, 2012 in International Application No. PCT/US2012/035479 filed on Apr. 27, 2012.
Office Action dated Mar. 18, 2013 in U.S. Appl. No. 12/401,493, filed Mar. 10, 2009 and published as: 2009/0317817 dated Dec. 24, 2009.
Office Action dated Jul. 19, 2011 in U.S. Appl. No. 12/401,493, filed Mar. 10, 2009 and published as: 2009/0317817 dated Dec. 24, 2009.
Office Action dated Oct. 28, 2010 in U.S. Appl. No. 12/401,493, filed Mar. 10, 2009 and published as: 2009/0317817 dated Dec. 24, 2009.
Office Action dated Feb. 27, 2013 in U.S. Appl. No. 12/561,241, filed Sep. 16, 2009.
Office Action dated Jun. 15, 2012 in U.S. Appl. No. 12/561,241, filed Sep. 16, 2009.
Office Action dated Apr. 5, 2013 in U.S. Appl. No. 13/495,975, filed Jun. 13, 2012.

(56) References Cited

OTHER PUBLICATIONS

Office Action dated Apr. 5, 2013 in U.S. Appl. No. 13/517,532, filed Jun. 13, 2012.
Office Action dated Apr. 12, 2013 in U.S. Appl. No. 12/727,198, filed Mar. 18, 2010.
Office Action dated Jan. 28, 2013 in U.S. Appl. No. 13/457,978, filed Apr. 27, 2012 and published as: 2012/0276542 dated Oct. 1, 2012.
Office Action dated Sep. 17, 2012 in U.S. Appl. No. 13/457,978, filed Apr. 27, 2012 and published as: 2012/0276542 dated Oct. 1, 2012.
Office Action dated Feb. 6, 2013 in U.S. Appl. No. 13/458,036, filed Apr. 27, 2012 and published as: 2012/0264618 dated Oct. 18, 2012.
Office Action dated Sep. 24, 2012 in U.S. Appl. No. 13/458,036, filed Apr. 27, 2012 and published as: 2012/0264618 dated Oct. 18, 2012.
Office Action dated Feb. 5, 2013 in U.S. Appl. No. 13/458,341, filed Apr. 27, 2012.
Office Action dated Sep. 17, 2012 in U.S. Appl. No. 13/458,341, filed Apr. 27, 2012.
Office Action dated Nov. 7, 2014, in U.S. Appl. No. 13/791,466, filed Mar. 8, 2013 and published as US 2013-0295564 dated Nov. 7, 2013.
International Preliminary Report of Patentability dated Dec. 4, 2014 in International Application No. PCT/US2013/041906, filed May 20, 2013 and published as WO 2013/177086 dated Nov. 28, 2013.
Office Action dated Dec. 18, 2014 in U.S. Appl. No. 13/507,508, filed Jun. 13, 2012 and published as US 2013/0143211 dated Jun. 6, 2013.
Office Action dated Dec. 22, 2014 in U.S. Appl. No. 13/801,384, filed Mar. 13, 2013 and published as US 2013-0296180 dated Nov. 7, 2013.
International Search Report and Written Opinion dated Oct. 23, 2012 in International Application No. PCT/US2013/050145 filed on Jul. 11, 2013.
International Preliminary Report on Patentability dated Nov. 7, 2013 in International Application No. PCT/US2012/035479 filed on Apr. 27, 2012 and published as WO 2012/149339 dated Nov. 1, 2012.
Office Action dated Nov. 22, 2013, in U.S. Appl. No. 12/401,493, filed Mar. 10, 2009 and published as US 2009-0317817 dated Dec. 24, 2009.
Office Action dated Dec. 31, 2013, in U.S. Appl. No. 12/727,198, filed Mar. 18, 2010 and published as US 2010-0273165 dated Oct. 28, 2010.
Office Action dated Jan. 7, 2014, in U.S. Appl. No. 13/517,508, filed Jun. 13, 2012 and published as US 2013-0143211 dated Jun. 6, 2013.
Office Action dated Jun. 26, 2014, in U.S. Appl. No. 13/782,857, filed Mar. 1, 2013 and published as US 2013-0310260 dated Nov. 21, 2013.
U.S. Appl. No. 13/782,901, Final Office Action, dated May 28, 2015, 15 pages.
U.S. Appl. No. 13/782,901, Non-Final Office Action, dated Aug. 8, 2014, 13 pages.
U.S. Appl. No. 13/782,901, Non-Final Office Action, dated Nov. 17, 2015, 8 pages.
U.S. Appl. No. 13/782,901, Non-Final Office Action, dated May 12, 2016, 9 pages.
International Search Report and Written Opinion dated: Jul. 1, 2013 in International Application No. PCT/US2013/028699 filed on Mar. 1, 2013.
International Search Report and Written Opinion dated Jul. 16, 2013 in International Application No. PCT/US2013/041906 filed on May 20, 2013.
Office Action dated Aug. 13, 2013, in U.S. Appl. No. 13/517,508, filed Jun. 13, 2012 and published as US 2013-0143211 dated Jun. 6, 2013.

International Search Report and Written Opinion, dated Aug. 14, 2013 in International application No. PCT/US2013/041354 filed on: May 16, 2013.
Office Action dated Sep. 20, 2013, in U.S. Appl. No. 13/517,532, filed Jun. 13, 2012 and published as US 2013-0150249 dated Jun. 13, 2013.
Office Action dated Sep. 24, 2013, in U.S. Appl. No. 13/495,975, filed Jun. 13, 2012 and published as US 2012-0277119 dated Nov. 1, 2012.
Office Action dated Feb. 5, 2014 in U.S. Appl. No. 13/517,508, filed Jun. 13, 2012 and published as US 2013-0143211 dated Jun. 6, 2013.
Office Action dated Mar. 7, 2014, in U.S. Appl. No. 13/801,384, filed Mar. 13, 2013 and published as US 2013-0296180 dated Nov. 7, 2013.
Office Action dated Jan. 30, 2015, in U.S. Appl. No. 13/518,368, filed Feb. 6, 2013 and published as US 2013-0130923 dated May 23, 2013.
International Preliminary Report on Patentability dated Sep. 12, 2014 in International Application No. PCT/US2013/028699 filed on Mar. 1, 2013 and published as WO 2013/131021 dated Sep. 6, 2013.
Office Action dated Sep. 15, 2014 in U.S. Appl. No. 12/727,198, filed Mar. 18, 2010 and published as US 2010-0273165 dated Oct. 28, 2010.
International Search Report and Written Opinion, dated Jul. 30, 2014 in International application No. PCT/US2014/025132 filed on Mar. 13, 2014.
EP 13709696.2, Office Action, dated Sep. 25, 2015, 3 pages.
EP 13709696.2, Office Action, dated Feb. 16, 2016, 4 pages.
EP 13709696.2, Office Action, dated Apr. 5, 2017, 5 pages.
EP 18174047.3, Office Action, dated Jul. 5, 2019, 4 pages.
Aston, C. et al., "Optical Mapping: An Approach for Fine Mapping", Methods Enzymol, 303:55-73 (1999).
Ausubel, F. et al., "Current Protocols in Molecular Biology", John Wiley & Sons, Inc., vol. 1, 1994, 18 pages.
Beaucage, S. and Caruthers, M., "Deoxynucleoside Phosphoramidites—A New Class of Key Intermediates for Deoxypolynucleotide Synthesis", Tetrahedron Letters, 22(20):1859-1862 (1981).
Braslavsky, I. et al., "Sequence Information can be Obtained From Single DNA Molecules", PNAS, 100(7):3960-3964 (2003).
Chiu, R. et al., "Prenatal Exclusion of Beta Thalassaemia Major by Examination of Maternal Plasma", The Lancet, 360(9338):998-1000 (2002).
Chomczynski, P. and Mackey, K., "Short Technical Reports. Modification of the TRI Reagent™ Procedure for Isolation of RNA from Polysaccharide- and Proteoglycan-Rich Sources", Biotechniques, 19(6):942-945 (1995).
Costello, J. et al., "Restriction Landmark Genomic Scanning: Analysis of CpG Islands in Genomes by 2D Gel Electrophoresis", Methods in Molecular Biology, DNA Methylation: Methods and Protocols, $2^{nd}$ ed, 507:131-148 (2009).
Cruikshank, W. et al., "A Lipidated Anti-Tat Antibody Enters Living Cells and Blocks HIV-1 Viral Replication", J. Acquir. Immune Defic. Syndr. Hum. Retrovirol., vol. 14, No. 3, Mar. 1, 1997, 1 page.
Dai, B. et al., "Detection of Post-translational Modifications of Native Intact Nucleosomes by ELISA", Cell Death Detection ELISA PLUS Cat. No. 11774425 001, Version 11.0, Roche, Sep. 2010, pp. 1-19.
Dayie, K. et al., "3D C(CC)H TOCSY Experiment for Assigning Protons and Carbons in Uniformly $^{13}$C- and Selectively $^{2}$H-Labeled RNA", J. Mag. Reson, 130:97-101 (1998).
Dembo, A. et al., "Limit Distribution of Maximal Non-Aligned Two-Sequence Segmental Score", The Annals of Probability, 22(4):2022-2039 (1994).
Donis-Keller, H. et al., "Mapping Adenines, Guanines, and Pyrimidines in RNA", Nucleic Acids Research, 4(8):2527-2538 (1997).
Ellinger, J. et al., "CpG Island Hypermethylation of Cell-Free Circulating Serum DNA in Patients with Testicular Cancer", The Journal of Urology, 182(1):324-329 (2009).
FAN, H-M., "Molecular Counting: From Noninvasive Prenatal Diagnostics to Whole-Genome Haplotyping", Dissertation, Stanford University, Nov. 2010, 185 pages.

(56) References Cited

OTHER PUBLICATIONS

Ferguson-Smith, M., "Placental mRNA in Maternal Plasma: Prospects for Fetal Screening", PNAS, 100(8):4360-4362 (2003).
Flicek, P. and Birney, E., "Sense from Sequence Reads: Methods for Alignment and Assembly", Nature Methods Supplement, 6(11s):S6-S12 (2009).
Gardiner-Garden, M. and Frommer, M., "CpG Islands in Vertebrate Genomes", Journal Molecular Biology, 196(2):261-282 (1987).
Giles, F. et al., "Acute Myeloid Leukemia", American Society Hematology Education Program, 2002(1):73-110 (2002).
Goeddel, D., "Systems for Heterologous Gene Expression", Methods in Enzymology, 185:3-7 (1990).
"Homo sapiens Chromosome 13, GRCh37 Primary Reference Assembly", GenBank Accession No. CM000675.1, Available Online at, https://www.ncbi.nlm.nih.gov/nuccore/CM000675.1, Jun. 29, 2009, 2 pages.
"Homo sapiens Chromosome 5 Clone CTC-554D6, Complete Sequence", GenBank Accession No. AC008575.7, Available online at: www.ncbi.nlrn.nih.gov/nuccore/ac008575.7, Jul. 20, 2001, 37 pages.
"Homo sapiens Genomic DNA, Chromosome 21q22.2, DSCR Region, Clone D47-S479, Segment 12/16, Complete Sequence", GenBank Accession No. AP000160.1, Available Online at, https://www.ncbi.nlm.nih.gov/nuccore/AP000160.1/, Jan. 8, 2000, 22 pages.
"Homo sapiens Prostaglandin-Endoperoxide Synthase 2 (PTGS2), RefSeqGene on Chromosome 1", GenBank Accession No. NG_028206.2, Available online at: www.ncbi.nlm.nih.gov/nuccore/ng_028206.2, Sep. 13, 2017, 7 pages.
"Human DNA Sequence from Clone RP11-417C20 on Chromosome 13, Complete Sequence", GenBank Accession No. AL138704.12, Available Online at, https://www.ncbi.nlm.nih.gov/nuccore/AL138704.12/, Dec. 13, 2012, 35 pages.
Health Screen Inc , "The Cancer Test, Cell Free DNA", Available on internet at: http://www.thecancertest.com/science-of-cell-free-dna/, Mar. 20, 2011.
Hsu, L. et al., "Denoising Array-Based Comparative Genomic Hybridization Data Using Wavelets", Biostatistics, 6(2):211-226 (2005).
Jensen, T. et al., "Detection of Microdeletion 22q11.2 in a Fetus by Next-Generation Sequencing of Maternal Plasma", Clinical Chemistry, 58(7):1148-1151 (2012).
Jensen, T. et al., "High-Throughput Massively Parallel Sequencing for Fetal Aneuploidy Detection from Maternal Plasma", PLoS One 8(3):e57381 (2013) 8 pages.
Krueger, F. and Andrews, S., "Bismark: A Flexible Aligner and Methylation Caller for Bisulfite-Seq Applications", Bioinformatics, 27(11):1571-1572 (2011).
Langmead, B. et al., "Ultrafast and Memory-Efficient Alignment of Short DNA Sequences to the Human Genome", Genome Biology, 10(3):R25.1-R25.10 (2009).
Li, J-Y et al., "Dynamic Distribution of Linker Histone H1.5 in Cellular Differentiation", PLOS Genetics, 8(8):e1002879 (2012) 13 pages.
Li, H. et al., "Mapping Short DNA Sequencing Reads and Calling Variants Using Mapping Quality Scores", Genome Research, 18(11):1851-1858 (2008).
Lo, K. et al., "RAPIDR: An Analysis Package for Non-Invasive Prenatal Testing of Aneuploidy", Bioinformatics, 30(20):2965-2967 (2014).
Miller, C. et al., "ReadDepth: A Parallel R Package for Detecting Copy Number Alterations from Short Sequencing Reads", PLoS One, 6(1):e16327 (2011), 7 pages.
Mouliere, F. et al., "Multi-Marker Analysis of Circulating Cell-Free DNA Toward Personalized Medicine for Colorectal Cancer", Molecular Oncology, 8(5):927-941 (2014).
Palomaki, G. et al., "DNA Sequencing of Maternal Plasma to Detect Down Syndrome: An International Clinical Validation Study", Genet. Med. 13(11):913-920 (2011).

Papageorgiou, E. et al., "Fetal-Specific DNA Methylation Ratio Permits Non-Invasive Prenatal Diagnosis of Trisomy 21", Nat. Med. 17(4):510-513 (2011).
Papageorgiou, E. et al., "Sites of Differential DNA Methylation Between Placenta and Peripheral Blood: Molecular Markers for Noninvasive Prenatal Diagnosis of Aneuploidies", The American Journal of Pathology, 174(5):1609-1618 (2009).
Schroeder, D. "The Human Placenta Methylome", PNAS 110(15):6037-6042 (2013).
Srinivasan, A. et al., "Noninvasive Detection of Fetal Subchromosome Abnormalities Via Deep Sequencing of Maternal Plasma", The American Journal of Human Genetics, 92(2):167-176 (2013).
Strauss, W., "Using DNA Fragments as Probes," Current Protocols in Molecular Biology 24(1):6.3.1-6.3.6 (1993).
Tsaliki, E. et al., "MeDIP Real-Time qPCR of Maternal Peripheral Blood Reliably Identifies Trisomy 21", Prenatal Diagnosis, 32(10):996-1001 (2012).
Van Der Schoot, C. et al., "Real Time PCR of Bi-Allelic Insertion/Deletion Polymorphisms Can Serve as a Reliable Positive Control for Cell-Free Fetal DNA in Non-Invasive Prenatal Genotyping", Blood, 102:93a (2003).
Verbeck, G. et al., "A Fundamental Introduction to Ion Mobility Mass Spectrometry Applied to the Analysis of Biomolecules", Journal of Biomolecular Techniques, 13(2):56-61 (2002).
Vincent, M. et al., "Helicase-Dependent Isothermal DNA Amplification", EMBO reports, 5(8):795-800 (2004).
Wilkinson, D., "In Situ Hybridization; A Practical Approach", Ann. Hum. Genet., 63(4):377-381 (2009).
Willenbrock, H. and Fridlyand, J., "A Comparison Study: Applying Segmentation to Array CGH Data for Downstream Analyses", Bioinformatics, 21(22):4084-4091 (2005).
Yoon, S. et al., "Sensitive and Accurate Detection of Copy Number Variants Using Read Depth of Coverage", Genome Research, 19(9):1586-1592 (2009).
Yu, S, et al., "Size-Based Molecular Diagnostics Using Plasma DNA for Noninvasive Prenatal Testing", Proc. Nat. Acad. Sci., 111(23):8583-8588 (2014).
Zhao, C. et al., "Detection of Fetal Subchromosomal Abnormalities by Sequencing Circulating Cell-Free DNA From Maternal Plasma", Clinical Chemistry, 61(4):608-616 (2015).
U.S. Appl. No. 13/457,978, Notice of Allowance, dated Jan. 1, 2013, 7 pages.
U.S. Appl. No. 13/782,901, Corrected Notice of Allowance, dated Dec. 7, 2016, 6 pages.
U.S. Appl. No. 13/782,901, Notice of Allowance, dated Nov. 14, 2016, 8 pages.
U.S. Appl. No. 13/791,466, Final Office Action, dated Aug. 12, 2016, 10 pages.
U.S. Appl. No. 13/791,466, Final Office Action, dated Aug. 3, 2015, 10 pages.
U.S. Appl. No. 13/940,162, Final Office Action, dated Mar. 17, 2016, 17 pages.
U.S. Appl. No. 13/940,162, Non-Final Office Action, dated Aug. 20, 2015, 12 pages.
U.S. Appl. No. 14/772,544, Final Office Action, dated Dec. 11, 2019, 20 pages.
U.S. Appl. No. 14/772,544, Non-Final Office Action, dated Jul. 24, 2018, 16 pages.
U.S. Appl. No. 15/124,324, Final Office Action, dated Feb. 13, 2019, 7 pages.
U.S. Appl. No. 15/124,324, Final Office Action, dated Apr. 20, 2020, 9 pages.
U.S. Appl. No. 15/124,324, Non-Final Office Action, dated Apr. 14, 2021, 8 pages.
U.S. Appl. No. 15/124,324, Non-Final Office Action, dated Aug. 6, 2018, 8 pages.
U.S. Appl. No. 15/124,324, Non-Final Office Action, dated Sep. 26, 2019, 9 pages.
U.S. Appl. No. 15/443,051, Final Office Action, dated Mar. 28, 2019, 12 pages.
U.S. Appl. No. 15/443,051, Non-Final Office Action, dated Aug. 2, 2018, 13 pages.

(56) References Cited

OTHER PUBLICATIONS

U.S. Appl. No. 15/443,051, Non-Final Office Action, dated Oct. 2, 2019, 14 pages.
U.S. Appl. No. 15/443,051, Notice of Allowance, dated Apr. 20, 2020, 10 pages.
U.S. Appl. No. 15/517,107, Final Office Action, dated May 26, 2020, 8 pages.
U.S. Appl. No. 15/517,107, Non-Final Office Action, dated Jan. 21, 2020, 9 pages.
EP 15714069.0, Notice of Decision to Grant, dated Apr. 9, 2020, 2 pages.
EP 15714069.0, Office Action, dated Apr. 17, 2018, 4 pages.
EP 15714069.0, Summons to Attend Oral Proceedings, dated Feb. 26, 2019, 7 pages.
EP 15753247.4, Notice of Decision to Grant, dated Jul. 2, 2020, 2 pages.
EP 15753247.4, Office Action, dated Oct. 14, 2019, 4 pages.
EP 15753247.4, Office Action, dated Aug. 19, 2019, 5 pages.
EP 15753247.4, Office Action, dated Oct. 17, 2018, 6 pages.
EP 15785002.5, Notice of Decision to Grant, dated Apr. 9, 2020, 2 pages.
EP 15785002.5, Office Action, dated Oct. 10, 2018, 4 pages.
EP 16173137.7, Extended European Search Report, dated Nov. 14, 2016, 8 pages.
EP 18174047.3, Extended European Search Report, dated Aug. 13, 2018, 8 pages.
EP 18174047.3, Notice of Decision to Grant, dated Mar. 26, 2020, 2 pages.
EP 20170556.3, Extended European Search Report, dated Nov. 4, 2020, 9 pages.
EP 20172801.1, Extended European Search Report, dated Sep. 22, 2020, 9 pages.
EP 20187578.8, Extended European Search Report, dated Nov. 11, 2020, 13 pages.
PCT/US2012/035479, International Search Report and Written Opinion, dated Jan. 10, 2012, 20 pages.
PCT/US2013/050145, International Preliminary Report on Patentability, dated Jan. 22, 2015, 12 pages.
PCT/US2014/025132, International Preliminary Report on Patentability, dated Sep. 24, 2015, 16 pages.
PCT/US2015/020250, International Preliminary Report on Patentability, dated Sep. 22, 2016, 8 pages.
PCT/US2015/020250, International Search Report and Written Opinion, dated May 28, 2015, 12 pages.
PCT/US2015/054903, International Preliminary Report on Patentability, dated Apr. 20, 2017, 14 pages.
PCT/US2015/054903, International Search Report and Written Opinion, dated Mar. 30, 2016, 21 pages.

* cited by examiner

| Condition | Total S+P | Fetal S+P | Total+Fetal | Total % in S | Total % in P |
|---|---|---|---|---|---|
| Super Pool 12 | 698 c/rxn | 42 c/rxn | 739 c/rxn | | |
| 25K Spin | 845 c/rxn | 37 c/rxn | 882 c/rxn | 62 % | 38 % |
| 100K Spin | 596 c/rxn | 32 c/rxn | 628 c/rxn | 82 % | 18 % |

FIG. 5

| Condition | Total S to S | Fetal S to S |
|---|---|---|
| 25K/No Spin | 522/698 (75%) | 34/42 (83%) |
| 100K/25KSpin | 489/522 (94%) | 31/34 (90%) |
| 100K/No Spin | 489/698 (70%) | 31/42 (74%) |
| SP 12 QPCR/FQA4b | 698/2557 (27%) | 42/307 (14%) |

FIG. 6

METHODS AND PROCESSES FOR NON-INVASIVE ASSESSMENT OF GENETIC VARIATIONS

RELATED APPLICATIONS

This patent application is a continuation of U.S. patent application Ser. No. 15/443,051 filed Feb. 27, 2017, which is a continuation of U.S. patent application Ser. No. 13/782,901 filed on Mar. 1, 2013, entitled METHODS AND PROCESSES FOR NON-INVASIVE ASSESSMENT OF GENETIC VARIATIONS, naming Charles R. Cantor, Grace DeSantis, Reinhold Mueller, and Mathias Ehrich as inventors, which claims the benefit of U.S. Provisional Patent Application No. 61/606,226 filed on Mar. 2, 2012, entitled METHODS AND PROCESSES FOR NON-INVASIVE ASSESSMENT OF GENETIC VARIATIONS, naming Charles R. Cantor as inventor. The entire content of the foregoing applications are incorporated herein by reference, including all text, tables and drawings.

FIELD

Technology provided herein relates in part to methods, processes and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. Identification of one or more genetic variations or variances sometimes involves the analysis of cell-free DNA.

Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

The presence of fetal nucleic acid in maternal plasma allows for non-invasive prenatal diagnosis through the analysis of a maternal blood sample. For example, quantitative abnormalities of fetal DNA in maternal plasma can be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma can be a useful mechanism for the monitoring of fetomaternal well-being.

Early detection of pregnancy-related conditions, including complications during pregnancy and genetic defects of the fetus is important, as it allows early medical intervention necessary for the safety of both the mother and the fetus. Prenatal diagnosis has been conducted using cells isolated from the fetus through procedures such as chorionic villus sampling (CVS) or amniocentesis. However, these conventional methods are invasive and present an appreciable risk to both the mother and the fetus. The National Health Service currently cites a miscarriage rate of between 1 and 2 percent following the invasive amniocentesis and chorionic villus sampling (CVS) tests. The use of non-invasive screening techniques that utilize circulating CFF-DNA can be an alternative to these invasive approaches.

SUMMARY

Provided in some aspects are methods for enriching fetal nucleic acid in sample nucleic acid that includes fetal nucleic acid and maternal nucleic acid, comprising: (a) obtaining cell-free circulating sample nucleic acid from a biological sample from a pregnant female, which sample nucleic acid comprises vesicle-free nucleic acid and vesicular nucleic acid; and (b) separating some or substantially all of the vesicular nucleic acid from the sample nucleic acid, thereby generating a separation product enriched for the vesicle-free nucleic acid, where fetal nucleic acid in the separation product is enriched relative to fetal nucleic acid in the sample nucleic acid. In some embodiments, the method further comprises (c) analyzing nucleic acid in the separation product.

Also provided, in some aspects, are methods which comprise analyzing nucleic acid in a separation product prepared by a process comprising: (a) obtaining cell-free circulating sample nucleic acid from a biological sample from a pregnant female, which sample nucleic acid comprises vesicle-free nucleic acid, vesicular nucleic acid, maternal nucleic acid and fetal nucleic acid; and (b) separating some or substantially all of the vesicular nucleic acid from the sample nucleic acid, thereby generating a separation product enriched for the vesicle-free nucleic acid, where the fetal nucleic acid in the separation product is enriched relative to the fetal nucleic acid in the sample nucleic acid.

Also provided, in some aspects, are methods for enriching vesicle-free nucleic acid in sample nucleic acid, comprising:

(a) obtaining cell-free circulating sample nucleic acid from a biological sample, which sample nucleic acid comprises vesicle-free nucleic acid and vesicular nucleic acid; and (b) separating some or substantially all of the vesicular nucleic acid from the sample nucleic acid, thereby generating a separation product, where vesicle-free nucleic acid in the separation product is enriched relative to vesicle-free nucleic acid in the sample nucleic acid. In some embodiments, the method further comprises (c) analyzing nucleic acid in the separation product.

Also provided, in some aspects, are methods which comprise analyzing nucleic acid in a separation product prepared by a process comprising: (a) obtaining cell-free circulating sample nucleic acid from a biological sample, which sample nucleic acid comprises vesicle-free nucleic acid and vesicular nucleic acid; and (b) separating some or substantially all of the vesicular nucleic acid from the sample nucleic acid, thereby generating a separation product, where vesicle-free nucleic acid in the separation product is enriched relative to vesicle-free nucleic acid in the sample nucleic acid.

Also provided, in some aspects, are methods for enriching fetal nucleic acid in sample nucleic acid that includes fetal nucleic acid and maternal nucleic acid, comprising (a) obtaining cell-free circulating sample nucleic acid from a biological sample from a pregnant female, which sample nucleic acid comprises maternal-derived vesicular nucleic acid and fetal-derived vesicular nucleic acid; and (b) separating some or substantially all of the maternal-derived vesicular nucleic acid from the fetal-derived vesicular nucleic acid, thereby generating a separation product enriched for the fetal-derived vesicular nucleic acid, where fetal nucleic acid in the separation product is enriched relative to fetal nucleic acid in the sample nucleic acid.

Also provided, in some aspects, are methods for enriching fetal nucleic acid in sample nucleic acid that includes fetal nucleic acid and maternal nucleic acid, comprising (a) obtaining cell-free circulating sample nucleic acid from a biological sample from a pregnant female, which sample nucleic acid comprises vesicle-free nucleic acid and vesicular nucleic acid; and (b) separating some or substantially all of the vesicular nucleic acid from the sample nucleic acid, thereby generating a separation product enriched for the vesicular nucleic acid, where fetal nucleic acid in the separation product is enriched relative to fetal nucleic acid in the sample nucleic acid.

In some embodiments, separating some or substantially all of the maternal-derived vesicular nucleic acid from the fetal-derived vesicular nucleic acid comprises contacting the sample nucleic acid with an agent that specifically binds to maternal-derived vesicular nucleic acid. In some embodiments, separating some or substantially all of the maternal-derived vesicular nucleic acid from the fetal-derived vesicular nucleic acid comprises contacting the sample nucleic acid with an agent that specifically binds to fetal-derived vesicular nucleic acid.

In some embodiments, separating some or substantially all of the vesicular nucleic acid from the sample nucleic acid comprises filtering the sample nucleic acid and sometimes comprises centrifuging the sample nucleic acid and sometimes comprises use of ultracentrifugation. In some embodiments, separating some or substantially all of the vesicular nucleic acid from the sample nucleic acid comprises contacting the sample nucleic acid with an agent that specifically binds to vesicles comprising the vesicular nucleic acid. In some embodiments, the agent is an antibody. In some embodiments, the agent specifically binds to vesicles from hemopoietic tissue. In some embodiments, the agent specifically binds to vesicles from red blood cells. In some instances, the agent specifically binds to CD235a. In some embodiments, the agent specifically binds to vesicles from leukocytes. In some instances, the agent specifically binds to CD45. In some embodiments, the agent specifically binds to vesicles from lymphocytes. In some instances, the agent specifically binds to a vesicular component chosen from CD4, CD8 and CD20. In some embodiments, the agent specifically binds to vesicles from granulocytes. In some instances, the agent specifically binds to CD66b. In some embodiments, the agent specifically binds to vesicles from monocytes. In some instances, the agent specifically binds to CD14. In some embodiments, the agent specifically binds to vesicles from platelets. In some instances, the agent specifically binds to a vesicular component chosen from CD31, CD41, CD41a, CD42a, CD42b, CD61 and CD62P. In some embodiments, the agent specifically binds to vesicles from endothelial cells. In some instances, the agent specifically binds to a vesicular component chosen from CD31, CD34, CD54, CD62E, CD51, CD105, CD106, CD144 and CD146.

In some embodiments, generating the separation product comprises separating components bound by the agent away from the sample nucleic acid. In some embodiments, separating some or substantially all of the vesicular nucleic acid from the sample nucleic acid further comprises contacting the sample nucleic acid with an agent that specifically binds to a histone associated with vesicle-free nucleic acid. In some instances, the agent specifically binds to histone H3.3. In some instances, the agent specifically binds to histone H1. In some instances, histone H1 is unmethylated.

In some embodiments, the vesicular nucleic acid is within a vesicle having a diameter of less than about 1 micrometer. In some instances, the diameter is about 10 nanometers to about 600 nanometers. In some instances, the diameter is about 40 nanometers to about 100 nanometers.

Also provided, in some aspects, are methods for enriching fetal nucleic acid in sample nucleic acid that includes fetal nucleic acid and maternal nucleic acid, comprising: (a) obtaining cell-free circulating sample nucleic acid from a biological sample from a pregnant female, which sample nucleic acid comprises a first histone-associated nucleic acid species and a second histone-associated nucleic acid species; and (b) separating some or substantially all of the first histone-associated nucleic acid species from the sample nucleic acid, thereby generating a separation product enriched for the second histone-associated nucleic acid species, where fetal nucleic acid in the separation product is enriched relative to fetal nucleic acid in the sample nucleic acid. In some embodiments, the method further comprises (c) analyzing nucleic acid in the separation product.

Also provided, in some aspects, are methods which comprise analyzing nucleic acid in a separation product prepared by a process comprising: (a) obtaining cell-free circulating sample nucleic acid from a biological sample from a pregnant female, which sample nucleic acid comprises a first histone-associated nucleic acid species, a second histone-associated nucleic acid species, maternal nucleic acid and fetal nucleic acid; and (b) separating some or substantially all of the first histone-associated nucleic acid species from the sample nucleic acid, thereby generating a separation product enriched for the second histone-associated nucleic acid species, where the fetal nucleic acid in the separation product is enriched relative to the fetal nucleic acid in the sample nucleic acid.

Also provided, in some aspects, are methods for enriching a histone-associated nucleic acid species in sample nucleic acid, comprising: (a) obtaining cell-free circulating sample nucleic acid from a biological sample, which sample nucleic acid comprises a first histone-associated nucleic acid species and a second histone-associated nucleic acid species; and (b) separating some or substantially all of the first histone-associated nucleic acid species from the sample nucleic acid, thereby generating a separation product enriched for the second histone-associated nucleic acid species. In some embodiments, the method further comprises (c) analyzing nucleic acid in the separation product.

Also provided, in some aspects, are methods which comprise analyzing nucleic acid in a separation product prepared by a process comprising: (a) obtaining cell-free circulating sample nucleic acid from a biological sample, which sample nucleic acid comprises a first histone-associated nucleic acid species and a second histone-associated nucleic acid species; and (b) separating some or substantially all of the first histone-associated nucleic acid species from the sample nucleic acid, thereby generating a separation product enriched for the second histone-associated nucleic acid species.

Also provided, in some aspects, are methods for enriching fetal nucleic acid in sample nucleic acid that includes fetal nucleic acid and maternal nucleic acid, comprising (a) obtaining cell-free circulating sample nucleic acid from a biological sample from a pregnant female, which sample nucleic acid comprises a first histone-associated nucleic acid species and a second histone-associated nucleic acid species; and (b) separating some or substantially all of the first histone-associated nucleic acid species from the second histone-associated nucleic acid species, thereby generating a separation product enriched for the second histone-associated nucleic acid species, where fetal nucleic acid in the separation product is enriched relative to fetal nucleic acid in the sample nucleic acid.

In some embodiments, a method comprises (c) analyzing nucleic acid in the separation product. In some embodiments, separating some or substantially all of the first histone-associated nucleic acid species from the second histone-associated nucleic acid species comprises contacting the sample nucleic acid with an agent that specifically binds to a histone associated with the first histone-associated nucleic acid species. In some embodiments, separating some or substantially all of the first histone-associated nucleic acid species from the second histone-associated nucleic acid species comprises contacting the sample nucleic acid with an agent that specifically binds to a histone associated with the second histone-associated nucleic acid species.

In some embodiments, the agent specifically binds to histone H1. In some embodiments, the agent specifically binds to histone H1.0. In some embodiments, the agent specifically binds to histone H1.1. In some embodiments, the agent specifically binds to histone H1.3. In some embodiments, the agent specifically binds to histone H1.5. In some embodiments, the agent is an antibody.

In some embodiments, the method comprises lysing vesicles present in the sample nucleic acid. In some embodiments, separating some or substantially all of the first histone-associated nucleic acid species from the sample nucleic acid comprises contacting the sample nucleic acid with an agent that specifically binds to a histone associated with the first histone-associated nucleic acid species. In some embodiments, the agent is an antibody. In some embodiments, the agent specifically binds to histone H3.3. In some instances, the agent specifically binds to histone H1. In some instances, the histone H1 is unmethylated. In some embodiments, generating the separation product comprises separating components bound by the agent away from the sample nucleic acid.

In some embodiments, the sample nucleic acid is from blood plasma, and in some embodiments, the sample nucleic acid is from blood serum. In some embodiments, obtaining the sample nucleic acid comprises subjecting the biological sample to an in vitro process that isolates the sample nucleic acid from other sample components. In some instances, the separation product comprises about 50% or greater vesicle-free nucleic acid. In some instances, the separation product comprises about 50% or greater second histone-associated nucleic acid species. In some embodiments, analyzing the nucleic acid in the separation product comprises subjecting the nucleic acid to an in vitro sequencing process. In some embodiments, the sequencing process provides sequence reads. In some embodiments, the method comprises mapping the sequence reads to a reference sequence and sometimes comprises counting the sequence reads mapped to the reference sequence. In some embodiments, the method comprises utilizing the counted sequence reads to generate an outcome determinative of the presence or absence of a genetic variation. In some embodiments, the genetic variation is a copy number variation. In some embodiments, the genetic variation is a chromosome aneuploidy and sometimes is a chromosome 21 aneuploidy.

Certain aspects of the technology are described further in the following description, examples, drawings and claims.

BRIEF DESCRIPTION OF THE DRAWINGS

The drawings illustrate aspects of the technology and are not limiting. For clarity and ease of illustration, the drawings are not made to scale and, in some instances, various aspects may be shown exaggerated or enlarged to facilitate an understanding of particular embodiments.

FIG. 5 presents a table showing a distribution of circulating DNA.

FIG. 6 presents a table showing a distribution of circulating DNA.

DETAILED DESCRIPTION

Figure 1:
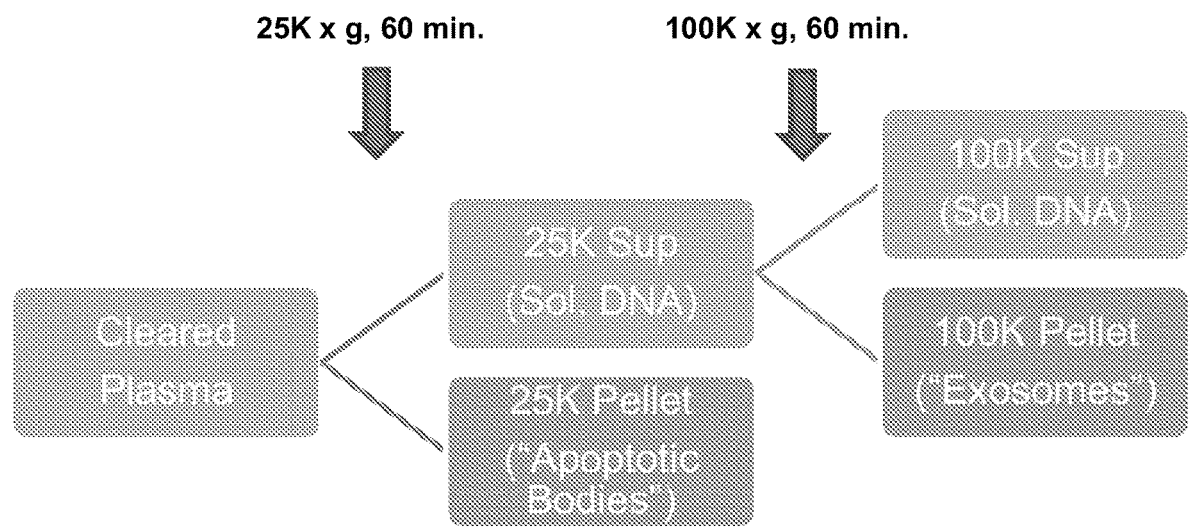
FIG. 1 shows a centrifugation diagram.

Provided herein are methods for enriching a sub-population of cell-free nucleic acid from a larger pool of cell-free nucleic acid in a sample nucleic acid. Cell-free nucleic acid often comprises a mixture of free nucleic acid fragments and nucleic acid fragments associated with various cellular components and/or cellular remnants, such as vesicles. In certain instances, it is advantageous to separate nucleic acid fragments associated with certain cellular components/remnants from the free (e.g., vesicle-free) nucleic acid fragments. In certain instances, it is advantageous to separate nucleic acid fragments associated with certain cellular components/remnants from nucleic acid fragments associated with different cellular components/remnants. Cell-free nucleic acid often is present in nucleosome form, and various subpopulations of nucleosomal cell-free nucleic acid can be associated with certain histones or histone variants. In certain instances, it is advantageous to separate a subpopulation of cell-free nucleic acid associated with a particular histone or histone variant from the sample nucleic acid. Such separation methods can be useful for the enrichment of a particular subpopulation of cell-free nucleic acid. Provided herein are methods for enriching vesicle-free nucleic acid, vesicular nucleic acid and/or a histone-associated nucleic acid species in a sample comprising circulating cell-free nucleic acid.

Provided also are improved methods, processes and apparatuses useful for identifying genetic variations. Identifying one or more genetic variations or variances can lead to diagnosis of, or determining predisposition to, a particular medical condition. Identifying a genetic variance can result in facilitating a medical decision and/or employing a helpful medical procedure.

Provided also are methods, processes and apparatuses useful for identifying a genetic variation. Identifying a genetic variation sometimes comprises detecting a copy number variation and/or sometimes comprises adjusting an elevation comprising a copy number variation. In some embodiments, identifying a genetic variation by a method described herein can lead to a diagnosis of, or determining a predisposition to, a particular medical condition. Identifying a genetic variance can result in facilitating a medical decision and/or employing a helpful medical procedure.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman).

Nucleic acid may be isolated from any type of suitable biological specimen or sample (e.g., a test sample). A sample or test sample can be any specimen that is isolated or obtained from a subject (e.g., a human subject, a pregnant female). Non-limiting examples of specimens include fluid or tissue from a subject, including, without limitation, umbilical cord blood, chorionic villi, amniotic fluid, cerebrospinal fluid, spinal fluid, ravage fluid (e.g., bronchoalveolar, gastric, peritoneal, ductal, ear, arthroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample is a cervical swab from a subject. In some embodiments, a biological sample may be blood and sometimes plasma or serum. As used herein, the term "blood" encompasses whole blood or any fractions of blood, such as serum and plasma as conventionally defined, for example. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain instances, buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In some embodiments, a fluid or tissue sample is collected from a pregnant female during or just after (e.g., 0 to 72 hours after) giving birth (e.g., vaginal or non-vaginal birth (e.g., surgical delivery)).

Nucleic Acid Isolation and Processing

Nucleic acid may be derived from one or more sources (e.g., cells, serum, plasma, buffy coat, lymphatic fluid, skin, soil, and the like) by methods known in the art. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). Nucleic acids sometimes comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid and/or "cell-free circulating" nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

The term "amplified" as used herein refers to subjecting a target nucleic acid in a sample to a process that linearly or exponentially generates amplicon nucleic acids having the same or substantially the same nucleotide sequence as the target nucleic acid, or segment thereof. The term "amplified" as used herein can refer to subjecting a target nucleic acid (e.g., in a sample comprising other nucleic acids) to a process that selectively and linearly or exponentially generates amplicon nucleic acids having the same or substantially the same nucleotide sequence as the target nucleic acid, or segment thereof. The term "amplified" as used herein can refer to subjecting a population of nucleic acids to a process that non-selectively and linearly or exponentially generates amplicon nucleic acids having the same or substantially the same nucleotide sequence as nucleic acids, or portions thereof, that were present in the sample prior to amplification. In some embodiments, the term "amplified" refers to a method that comprises a polymerase chain reaction (PCR).

Nucleic acid also may be processed by subjecting nucleic acid to a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of nucleotide sequence information.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

Nucleic acid can be fragmented by various methods known in the art, which include without limitation, physical, chemical and enzymatic processes. Non-limiting examples of such processes are described in U.S. Patent Application Publication No. 20050112590 (published on May 26, 2005, entitled "Fragmentation-based Methods and systems for sequence variation detection and discovery," naming Van Den Boom et al.). Certain processes can be selected to generate non-specifically cleaved fragments or specifically cleaved fragments. Non-limiting examples of processes that can generate non-specifically cleaved fragment nucleic acid include, without limitation, contacting nucleic acid with apparatus that expose nucleic acid to shearing force (e.g., passing nucleic acid through a syringe needle; use of a French press); exposing nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from portions of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

Nucleic acid may be specifically cleaved or non-specifically cleaved by contacting the nucleic acid with one or more enzymatic cleavage agents (e.g., nucleases, restriction enzymes). The term "specific cleavage agent" as used herein refers to an agent, sometimes a chemical or an enzyme that can cleave a nucleic acid at one or more specific sites. Specific cleavage agents often cleave specifically according to a particular nucleotide sequence at a particular site. Non-specific cleavage agents often cleave nucleic acids at non-specific sites or degrade nucleic acids. Non-specific cleavage agents often degrade nucleic acids by removal of nucleotides from the end (either the 5' end, 3' end or both) of a nucleic acid strand.

Any suitable non-specific or specific enzymatic cleavage agent can be used to cleave or fragment nucleic acids. A suitable restriction enzyme can be used to cleave nucleic acids, in some embodiments. Examples of enzymatic cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I, Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1, N6-ethenoadenine DNA glycosylase); exonucleases (e.g., exonuclease III); ribozymes, and DNAzymes. Nucleic acid may be treated with a chemical agent, and the modified nucleic acid may be cleaved. In non-limiting examples, nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts.

Nucleic acid may be single or double stranded. Single stranded DNA, for example, can be generated by denaturing double stranded DNA by heating or by treatment with alkali, for example. Nucleic acid sometimes is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Subpopulation Enrichment of Cell-Free Nucleic Acid

In some embodiments, the sample nucleic acid is processed such that a subpopulation of cell-free nucleic acid is enriched in the sample nucleic acid. In some embodiments, the enrichment is achieved by specifically removing or depleting another subpopulation of cell-free nucleic acid. This method is sometimes referred to herein as "negative enrichment". Such negative enrichment methods can exploit differences in certain characteristics of nucleic acid subpopulations in a sample comprising cell-free nucleic acid. For example, in some instances, cell-free nucleic acid is a mixture of vesicular and vesicle-free nucleic acid. By selectively depleting a sample nucleic acid of vesicular nucleic acid, for example: the sample becomes enriched for vesicle-free nucleic acid, and vice-versa. In some instances, cell-free nucleic acid is a mixture of different vesicular nucleic acid species (e.g., vesicular nucleic acid having originated from different types of tissue). By selectively depleting a sample nucleic acid of a certain vesicular nucleic acid species, for example, the sample becomes enriched for a different vesicular nucleic acid species.

In some embodiments, the enrichment is achieved by specifically targeting a desired subpopulation of cell-free nucleic acid. This method is sometimes referred to herein as "positive enrichment". Such positive enrichment methods can exploit differences in certain characteristics of nucleic acid subpopulations in a sample comprising cell-free nucleic acid. As mentioned above, in some instances, cell-free nucleic acid is a mixture of different vesicular nucleic acid species (e.g., vesicular nucleic acid having originated from different types of tissue). By selectively targeting a sample nucleic acid of a certain vesicular nucleic acid species, for example, the sample becomes enriched for such vesicular nucleic acid species.

In another example, cell-free nucleic acid often is present in nucleosome form. The particular histones and histone variants associated with such nucleosomal cell-free nucleic acid can vary depending on the cellular origin of the nucleic acid. Thus, certain subpopulations of cell-free nucleic acid can be distinguished froth one another based on the type of histone and/or histone variant with which it is associated. By selectively depleting or targeting a sample nucleic acid of nucleic acid associated with one type of histone or histone variant, sample nucleic acid can become enriched for nucleic acid associated with a different histone or histone variant. Non-limiting examples of positive and negative enrichment of cell-free nucleic acid are described in further detail below.

Depletion of Vesicular Nucleic Acid

Cell-free nucleic acid often comprises a mixture of vesicular nucleic acid and vesicle-free nucleic acid. Vesicular nucleic acid is nucleic acid located in and/or associated with a vesicle or vesicle fragment. As used herein, a vesicle is a small membrane-enclosed body that can store or transport material. Often, the membrane enclosing the vesicle is similar to that of the cellular plasma membrane and comprises at least one phospholipid bilayer. Vesicles often are formed by a process in which a portion of a cellular membrane separates from the cell. Vesicles may also be referred to as microvesicles, nanovesicles, intralumenal vesicles, endosomal-like vesicles, exocytosed vesicles, microparticles, apoptotic bodies, apobodies, bleb, blebby, exosomes, dexosomes, and prostasomes. Vesicles sometimes are a byproduct of cell death (e.g., apoptotic bodies, apobodies). Vesicles can include any shed membrane bound particle that is derived from the plasma membrane or an internal membrane. Vesicles also can include one or more cell-derived structures surrounded by a lipid bilayer membrane. Vesicles also can include membrane fragments.

Vesicles can be released into the extracellular environment from a variety of different cells such as but not limited to, endothelial cells, hemopoietic cells, and cells that have undergone genetic, environmental, and/or any other variations or alterations (e.g. tumor cells). Vesicles can have, for example, a diameter of less than 1 micrometer. In some instances, vesicles can have a diameter that is about 10 nanometers to about 600 nanometers. In some instances, vesicles can have a diameter of about 40 nanometers to about 100 nanometers. Vesicles can have, for example, a diameter of about 45, 50, 55, 60, 65, 70, 75, 80, 85, 90, or 95 nanometers. Certain vesicles can have a diameter of about 100 nanometers or greater. For example, certain vesicles can have a diameter of about 200 nanometers, 300 nanometers, 400 nanometers, 500 nanometers, 600 nanometers, 700 nanometers, 800 nanometers, 900 nanometers, 1000 nanometers, 1100 nanometers, 1200 nanometers, 1300 nanometers, 1400 nanometers, 1500 nanometers or greater.

The origins of vesicular nucleic acid and vesicle-free nucleic acid in a cell-free nucleic acid sample can differ. For example, a cell free nucleic acid sample from a pregnant female can comprise vesicular nucleic acid of maternal and fetal origin and vesicle-free nucleic acid of maternal and fetal origin. The relative proportions of vesicular and vesicle-free nucleic acid can be different for maternal-derived cell-free nucleic acid and fetal-derived cell-free nucleic acid. In some instances, for example, the majority of maternal-derived cell-free nucleic acid can be vesicular and the majority of fetal-derived cell-free nucleic acid can be vesicle-free. In another example, cell-free nucleic acid derived from tumors or solid organ transplants can be substantially vesicle-free and cell-free nucleic acid derived from normal or host tissue can be substantially vesicular. Without being limited by theory, such characteristics related to the presence or absence of vesicular nucleic acid may account for size (i.e. nucleotide sequence length) differences observed for certain populations of cell free nucleic acid. For example, cell-free DNA derived from fetal, transplant or tumor sources, can be enriched for a smaller subpopulation of DNA compared to cell-free DNA derived from, maternal, host or normal sources, respectively, as described, for example, in Chan et al. (2004) Clin Chem 50:88-92; Diehl et al. (2005) Proc Natl Acad Sci 102:16368-73; Lo et al. (2010) Sci Transl Med 2:61ra91; Zheng et al. (2011) Clin Chem 169318; and Mouliere et al. (2011) PLoS One 6:9 e23418. In some instances, for example, fetal cell-free DNA may include less of 166-bp sized DNA fragments and more of 143-bp sized DNA fragments compared to maternal cell-free DNA. In some instances, the larger fragments may be present as vesicular DNA and thus may be less sensitive to circulating nucleases, for example, and the smaller fragments may be present as vesicle-free DNA and thus more sensitive to circulating nucleases, for example.

Vesicular nucleic acid and sometimes certain vesicular nucleic acid species (e.g., maternal derived vesicular nucleic acid) can be depleted from a sample using any method known in the art for separating biological material. Non-limiting separation methods include physical separation (e.g., filtration, centrifugation, dialysis, and the like) and methods that employ a binding agent. Filtration methods generally include methods whereby the vesicular nucleic acid is absorbed by a membrane or barrier and the vesicle-free nucleic acid is retained in the sample. Various filtration methods are known in the art and include, without limitation, microfiltration, gel filtration, and magnetic filtration. Centrifugation methods generally include methods whereby a separation of sample components is achieved by applying centrifugal force. Various centrifugation methods are known in the art and include, without limitation, ultracentrifugation, differential centrifugation, equilibrium density-gradient centrifugation and zonal centrifugation.

Separation methods that employ a binding agent also can be used to deplete vesicular nucleic acid or a certain vesicular nucleic acid species in a sample. In such methods, components (i.e. vesicles) bound by the agent are separated away from the sample. A binding agent is an agent that specifically binds to a vesicle component, such as a biomarker. An agent "specifically binds" to a vesicle component if the binding agent binds preferentially to the component, and, e.g., has less than about 30%, 20%, 10%, 5% or 1% cross-reactivity with another molecule. Methods for binding an agent to a vesicle are described, for example, in US patent application publication nos. 2011/0151460, 2010/0203529, and 2010/0184046. Binding agents can be monoclonal antibodies, polyclonal antibodies, Fabs, Fab', single chain antibodies, synthetic antibodies, DNA, RNA, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), dendrimers, or combinations thereof. For example, the binding agent can be a capture antibody. Such binding agents can be directly or indirectly coupled to a substrate or solid support. Often, the substrate or solid support is used to separate the vesicle from the sample. Some methods involve binding partners where one partner is associated with the vesicle (e.g. conjugated to a vesicle binding agent) and the other partner is associated with a solid support. In some instances, a single binding agent can be employed for the depletion of vesicular nucleic acid. In some instances, a combination of different binding agents may be employed for the depletion of vesicular nucleic acid. For example, at least 2, 3, 4, 5, 6, 7, 8, 9, 10, 11, 12, 13, 14, 15, 16, 17, 18, 19, 20, 25, 50, 75 or 100 different binding agents may be used to remove vesicular nucleic from a sample.

In some embodiments, a binding agent is specific for a component associated with a vesicle. Such components may include, for example, cell surface markers, membrane proteins, secreted factors or any other molecule that can become associated with a vesicle. In some embodiments, the binding agent is specific for a component on the surface of a vesicle. In some embodiments, the binding agent is specific for a component on a vesicle originating from a maternal cell. In some embodiments, the binding agent is specific for a component on a vesicle originating from a non-cancerous cell. In some embodiments, the binding agent is specific for a component on a vesicle originating from a host cell.

In some embodiments, the agent specifically binds to vesicles from hemopoietic tissue. In some embodiments, the agent specifically binds to vesicles from red blood cells. In some embodiments, the agent specifically binds to a vesicular component chosen from CD235a (glycophorin A), acetylcholinesterase, AMP deaminase, Band 3 (cdb3), BGP1, CD36, CD47, CD71 (transferrin receptor), chromium 51, erythrocyte creatine, globin, glycophorin B, hemoglobin, MBHb (membrane-bound hemoglobin), Rh Polypeptides, N-acetyl-9-O-acetylneuraminic acid, sequestrin, Ter119, thrombospondin (TSP), and VLA4. In some embodiments, the agent specifically binds to vesicles from leukocytes. In some embodiments, the agent specifically binds to a vesicular component chosen from CD45, 8-OHdG (8-hydroxydeoxyguanosine), ATPase (adenosine triphosphatase), beta2 leukocyte integrins (CD11/CD18), cathepsin G, CD15 (leuM1), CD18 (MHM23), CD43 (leukosialin, leu-22), CD53 (Ox-44), CD68 (KPI, macrosialin), CD95 (fas), CD166, diiodotyrosine (DIT), EFCC, fecal lactoferrin, glucose-6-phosphatase (G-6-Pase), HLA (human leukocyte antigen), HLE (human leukocyte elastase), ICAM-1, IL-8 (interleukin-8), L1, lactoferrin, LAM-1 (leukocyte adhesion molecule-1), LAP (leukocyte alkaline phosphatase), lectins, L-selectin, LSP1 (leukocyte-specific protein-1), Ly-9, M6 (leukocyte activation antigen), Mac-1, MPO (myeloperoxidase), and VIP (vasoactive intestinal polypeptide). In some embodiments, the agent specifically binds to vesicles from lymphocytes. In some embodiments, the agent specifically binds to a vesicular component chosen from CD1a, CD1d, CD2, CD3, CD4, CD5, CD7, CD8, CD11 b (Mac-1), CD16 (Leu 11b), CD19, CD20 (L26), CD21, CD22, CD24, CD25 (interleukin 2 receptor alpha), CD27, CD33, CD38, CD45, CD45RO, CD56, CD57, CD57/HNK1, CD69, CD72, CD79a, CD79b, CD86, CD90 (Thy-1), CD107a, CD134 (OX40), CD150, CD161, CD244 (2B4), BAT, ART2, CRTAM, CS1, DPIV (dipeptidyl peptidase IV), GM-1, H25, H366, HNK-1 (Leu 7), HP (*Helix pomatia*) receptor, LAT (linker for activation of T cells), Ly24 (Pgp-1), NKH1 (N901), protocadherin 15 (PCDH15), sialyl SSEA-1, FOXP3, HLA-DR, HML-1, Leu-22, Ly-2, Ly-m22, MICG, MRC OX 8, MRC OX-22, PD-1, RT6, D8/17, FMC7, M17, MUM-1, Pax-5 (BSAP), PC47H, 8220, BLAST-2 (EBVCS), Bu-1, TSA-2 (thymic shared Ag-2), MHC class II, TCR alpha beta, and TCR gamma delta. In some embodiments, the agent specifically binds to vesicles from granulocytes. In some embodiments, the agent specifically binds to a vesicular component chosen from CD11b, CD15, CD16, CD18, CD24, CD32, CD34, CD45, CD66b, 3C4, 8C5, alkaline phosphatase, calprotectin, CEACAM8 (carcinoembryonic antigen-related cell adhesion molecule 8), DH59B, EMR3, eosinophil cationic protein (ECP), granulocyte factor (GF), GMP, Gr-1 (Ly-6G), granulocyte elastase, HIS48, interleukin-8 (IL-8), LAP (leukocyte alkaline phosphatase), LRG, Mac-1, myeloperoxidase (MPO), NKH1, Poly(ADP-ribose), VEP8, and VEP9. In some embodiments, the agent specifically binds to vesicles from monocytes. In some embodiments, the agent specifically binds to a vesicular component chosen from CD11a (LFA-1 alpha), CD11b, CD14, CD15, CD54, CD62L (L-selectin), CD163, cytidine deaminase (CDD), Fc-receptors, 125I-WVH-1, 63D3, adipophilin, angiotensin converting enzyme, CB12, FLT-1, HLA-DR, hMGL, Ki-M1p, leucocyte tartrate-resistant acid phosphatase (FATRE), Leu-7, lysozyme, mannosyl receptors, peanut agglutinin (PNA), thromboplastin, thymidine phosphorylase (TP), TNF (tumor necrosis factor), urokinase (UK), VEP8, and VEP9. In some embodiments, the agent specifically binds to vesicles from platelets. In some embodiments, the agent specifically binds to a vesicular component chosen from CD31, CD36, CD41, CD41a, CD42a, CD42b, CD49b, CD61, CD62, CD62P (P-selectin), CD63 (glycoprotein-53), AK (adenylate kinase), annexin V, BTG (beta-thromboglobulin), glycocalicin (GC), GMP-140 (platelet-alpha-granule membrane protein), GPV (glycoprotein V), imidazoline receptors (IR-1), LAMP2 (lysosome-associated membrane protein-2), PAC-1, PDMP (platelet-derived microparticles), platelet-associated factor XIIIa, platelet factor 4 (PF4), S12, serotonin (5-HT), thrombospondin (TSP), and thromboxane B2.

In some embodiments, the agent specifically binds to vesicles from endothelial cells. In some embodiments, the agent specifically binds to a vesicular component chosen from CD31 (PECAM-1), CD34, CD54 (ICAM-1), CD62E, CD62P (p-Selectin GMP140), CD51, CD105 (Endoglin), CD106 (VCAM-1, vascular cell adhesion molecule-1), CD144 (VE-cadherin), CD146 (P1H12), 7B4 antigen, ACE (angiotensin-converting enzyme), BNH9/BNF13, D2-40, E-selectin, EN4, Endocan (ESM-1), Endoglyx-1, Endomuci, Endosialin (TEM-1, FB5), Eotaxin-3, EPAS1, Factor VIII related antigen, FB21, Flk-1 (VEGFR-2), Flt-1 (VEGFR-1), GBP-1 (guanylate-binding protein-1), GRO-alpha, Hex, ICAM-2 (intercellular adhesion molecule 2), LYVE-1, MECA-32, MECA-79, MRB (magic roundabout), Nucleolin, PAL-E (pathologische anatomie Leiden-endothelium), RPTPmu (receptor protein tyrosine phosphatase mu), RTKs, TEM1 (Tumor endothelial marker 1), TEM5 (Tumor endothelial marker 5), TEM7 (Tumor endothelial marker 7), TEM8 (Tumor endothelial marker 8), Thrombomodulin (TM, CD141), VEGF (vascular endothelial growth factor), and vWF (von Willebrand factor).

In some embodiments, the binding agent is an antibody. For example, a vesicle (e.g., a vesicle comprising nucleic acid) may be removed from a sample using one or more antibodies specific for one or more antigens present on the vesicle. Antibodies can be immunoglobulin molecules or immunologically active portions of immunoglobulin molecules, i.e., molecules that contain an antigen binding site that specifically binds an antigen. A variety of antibodies and antibody fragments are available to and can be generated by the artisan for use as a specific binding agent. Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of such antibodies. Polyclonal and monoclonal antibodies that bind specific antigens are commercially available, and methods for generating such antibodies are known. The binding agent also can be a polypeptide or peptide. The term polypeptide is used herein in its broadest sense and may include a sequence of amino acids, amino acid analogs, or peptidomimetics, typically linked by peptide bonds. The polypeptides may be naturally occurring, processed forms of naturally occurring polypeptides (such as by enzymatic digestion), chemically synthesized, or recombinantly expressed. The polypeptides for use in the methods herein may be chemically synthesized using standard techniques. The polypeptides may comprise D-amino acids (which are resistant to L-amino acid-specific proteases), a combination of D- and L-amino acids, beta amino acids, or various other designer or non-naturally occurring amino acids (e.g., beta-methyl amino acids, C alpha-methyl amino acids, N alpha-methyl amino acids, and the like) to convey special properties. Synthetic amino acids may include ornithine for lysine, and norleucine for leucine or isoleucine. In some instances, polypeptides can have peptidomimetic bonds, such as ester bonds, to prepare polypeptides with novel properties. Polypeptides can also include peptoids (N-substituted glycines), in which the side chains are appended to nitrogen atoms along the molecule's backbone, rather than to the alpha-carbons, as in amino acids.

In some embodiments, a binding agent can be linked directly or indirectly to a solid support or substrate. In some embodiments, vesicles are associated with a solid support, such as the solid supports described below, by one or more binding agents, such as the binding agents described herein. A solid support or substrate can be any physically separable solid to which a binding agent can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some instances, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, the solid phase can be a collection of particles. In certain embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$).

Using the methods described herein, vesicles (and the nucleic acid therein) can be separated away from a sample nucleic acid, thereby generating a separation product. Separation products can be partially or substantially free of vesicular nucleic acid. As used herein, the term "partially or substantially free" refers to a separation product for which at least about 50% to about 100% of the vesicular nucleic acid has been depleted. For example, a separation product that is partially or substantially free of vesicular nucleic acid has had at least about 60%, 70%, 80%, 90%, 95%, 96%, 97%, 98%, 99% or 99.9% of vesicular nucleic acid depleted. In certain embodiments, separation products can be partially or substantially free of vesicular nucleic acid originating from maternal cells. In certain embodiments, separation products can be partially or substantially free of vesicular nucleic acid originating from host cells. In certain embodiments, separation products can be partially or substantially free of vesicular nucleic acid originating from non-cancerous cells. In certain embodiments, separation products can be partially or substantially free of vesicular nucleic acid originating from endothelial cells. In certain embodiments, separation products can be partially or substantially free of vesicular nucleic acid originating from hematopoietic cells. In certain embodiments, separation products can be partially or substantially free of vesicular nucleic acid originating from red blood cells. In certain embodiments, separation products can be partially or substantially free of vesicular nucleic acid originating from leukocytes. In certain embodiments, separation products can be partially or substantially free of vesicular nucleic acid originating from lymphocytes. In certain embodiments, separation products can be partially or substantially free of vesicular nucleic acid originating from granulocytes. In certain embodiments, separation products can be partially or substantially free of vesicular nucleic acid originating from monocytes. In certain embodiments, separation products can be partially or substantially free of vesicular nucleic acid originating from platelets.

Selection of Vesicular Nucleic Acid

In some embodiments, a vesicular nucleic acid species is enriched using a positive enrichment approach. For example, in some embodiments, a fetal-derived vesicular nucleic acid species is enriched by selectively targeting a specific feature (e.g., biomarker) of the fetal derived vesicle, as described above. In some embodiments a fetal-derived vesicle is an apoptotic body. In some embodiments, a fetal-derived vesicular nucleic acid species is enriched using a centrifugation method. Centrifugation methods generally include methods whereby a separation of sample components is achieved by applying centrifugal force. Various centrifugation methods are known in the art and include, without limitation, ultracentrifugation, differential centrifugation, equilibrium density-gradient centrifugation and zonal centrifugation.

In some instances, centrifugation can separate components of a sample (e.g., microparticles, apoptotic bodies) and thus enrich for a subpopulation of nucleic acid associated with such components. Thus, without being limited by theory, if a larger proportion of fetal nucleic acid is associated with a certain sample component (e.g., apoptotic bodies) than maternal nucleic acid, then enrichment of the sample component using centrifugation can enrich for fetal nucleic acid. In some instances, without being limited by theory, if a larger proportion of maternal nucleic acid is associated with a certain sample component (e.g., apoptotic bodies) than fetal nucleic acid, then depletion of the sample component using centrifugation can enrich for fetal nucleic acid. In some embodiments, centrifugation comprises use of ultracentrifugation (e.g., high speed centrifugation). A centrifugation process typically generates a supernatant and a pellet, or zones within a gradient (e.g., density gradient), in certain instances. In some embodiments, fetal nucleic acid is enriched in the supernatant. In some embodiments, fetal nucleic acid is enriched in the pellet. In some embodiments, fetal nucleic acid is enriched in one or more zones within a gradient. In some embodiments, the supernatant is subjected to one or more further centrifugations. In some embodiments, the pellet is subjected to one or more further centrifugations.

To achieve a desired separation of sample components, one or more of speed, duration and amount of centrifugation can be adjusted. In some embodiments, a centrifugation speed of about 1000 g or greater is used. For example, a centrifugation speed of about 1200 g, 1300 g, 1400 g, 1500 g, 1600 g, 1800 g, 2000 g, 2200 g, 2400 g, 2500 g, 2600 g, 2800 g, or 3000 g or greater can be used. In some embodiments, a centrifugation speed of about 1600 g is used. In some embodiments, a centrifugation speed of about 2500 g is used. In some embodiments, a centrifugation speed of about 20,000 g or greater is used. For example, a centrifugation speed of about 21,000 g, 22,000 g, 23,000 g, 24,000 g, 25,000 g, 26,000 g, 27,000 g, 28,000 g, 29,000 g, or 30,000 g or greater can be used. In some embodiments, a centrifugation speed of about 25,000 g is used. In some embodiments, a centrifugation speed of about 80,000 g or greater is used. For example, a centrifugation speed of about 80,000 g, 90,000 g, 95,000 g, 96,000 g, 97,000 g, 98,000 g, 99,000 g, 100,000 g, 101,000 g, 102,000 g, 103,000 g, 104,000 g, 105,000 g, 110,000 g or greater can be used. In some embodiments, a speed of about 100,000 g is used.

In some embodiments, a centrifugation duration of about 1 minute or greater is used. For example, a centrifugation duration of about 5 minutes, 10 minutes, 15 minutes, 20 minutes, 30 minutes, 40 minutes, 50 minutes, 60 minutes, 90 minutes, or 120 minutes or greater can be used. In some embodiments, a centrifugation duration of about 10 minutes is used. In some embodiments, a centrifugation duration of about 15 minutes is used. In some embodiments, a centrifugation duration of about 60 minutes is used.

Depletion of a Histone-Associated Nucleic Acid Species

Provided herein are methods for enriching a subpopulation of cell-free nucleic acid in a sample by separating a different subpopulation of cell-free nucleic acid associated with a certain histone or histone variant away from the sample. Histones are nuclear proteins that make up the nucleosome structure of the chromosomal fiber in eukaryotes. Nucleosomes generally comprise approximately 146 base pairs of DNA wrapped around a histone octamer which includes pairs of each of the four core histones (H2A, H2B, H3, and H4). The chromatin fiber can be further compacted through the interaction of a linker histone, H1, with the DNA between the nucleosomes to form higher order chromatin structures. Methylation of position-specific lysine residues in histone N termini can help regulate epigenetic transitions in chromatin. Certain lysine residues can exist in a mono-, di-, or trimethylated state. Arginine residues, can also be mono- or dimethylated.

As used herein, "histone variant" refers to various post-translational histone modifications (e.g., methylation, acetylation, phosphorylation and the like) and histone isoforms, epitopes or subtypes. For example, the H3 class of histones includes of four different sub-types: the main types, H3.1 and H3.2; the replacement type, H3.3; and the testis specific variant, H3t. H3.1 and H3.2 are closely related, only differing at Ser96. H3.1 differs from H3.3 in at least 5 amino acid positions. In another example, the linker histone H1 includes several subtypes including H1a, H1b, H1c, H1d, H1e, H1m, and H1(0), each of which comprises various amino acid sequence differences.

Differences in histones and/or histone variants can be exploited for the separation of certain subpopulations of cell-free nucleic acid away from a sample, thereby enriching for another subpopulation of cell-free nucleic acid. For example, a cell-free circulating sample nucleic acid from a biological sample can comprise a first histone-associated nucleic acid species and a second histone-associated nucleic acid species. Some or substantially all of the first histone-associated nucleic acid species can be separated from the sample nucleic acid, thereby generating a separation product enriched for the second histone-associated nucleic acid species.

Differences in histones and/or histone variants also can be exploited for the enrichment of fetal nucleic acid in sample nucleic acid that includes fetal nucleic acid and maternal nucleic acid. In some instances, cell-free circulating sample nucleic acid from a biological sample from a pregnant female comprises a first histone-associated nucleic acid species and a second histone-associated nucleic acid species. Some or substantially all of the first histone-associated nucleic acid species can be separated from the sample nucleic acid, thereby generating a separation product enriched for the second histone-associated nucleic acid species, where fetal nucleic acid in the separation product is enriched relative to fetal nucleic acid in the sample nucleic acid.

In one example, histone H3.1 can be highly enriched in fetal liver, compared to histone H3.1 levels in adult tissues including liver, kidney and heart. In adult tissue, the H3.3 variant can be more abundant than the H3.1 variant (see e.g., United States Patent Application Publication nos. 2007/0243549 and 2010/0240054). Thus, a first histone-associated nucleic acid species can be a nucleic acid associated with histone H3.3 and a second histone-associated nucleic acid species can be a nucleic acid associated with histone H3.1. Because histone H3.1 can be enriched in fetal tissue, separating some or substantially all of the first histone-associated nucleic acid species (i.e. histone H3.3 associated nucleic acid) from the sample nucleic acid can deplete a proportion of maternal nucleic acid and generate a separation product enriched for fetal nucleic acid relative to fetal nucleic acid in the sample nucleic acid. In some instances, the conformational structure of fetal DNA in nucleosomes is such that histone H3.1 is more exposed in fetal DNA than in maternal DNA. Such a difference can also be exploited to target histone H3.1.

In another example, histone H1a can be enriched in fetal retina, compared to histone H1a levels in adult retina, which can have relatively higher levels of histone H1b and H1(0) (see Perkins and Young (1987) Jpn J Ophthalmol. 31(4): 590-7). Thus, a first histone-associated nucleic acid species can be a nucleic acid associated with histone H1b and/or H1(0) and a second histone-associated nucleic acid species can be a nucleic acid associated with histone H1a. Because histone H1a can be enriched in certain fetal tissue, separating some or substantially all of the first histone-associated nucleic acid species (i.e. histone H1b and/or H1(0) associated nucleic acid) from the sample nucleic acid can deplete a proportion of maternal nucleic acid and generate a separation product enriched for fetal nucleic acid relative to fetal nucleic acid in the sample nucleic acid.

In another example, certain subpopulations of cell-free nucleic acid can be associated with histones comprising one or more posttranslational modifications such as methylation, acetylation, phosphorylation, and the like. For instance, fetal nucleic acid may be associated with a methylated histone, such as, for example a methylated histone H1 or H3 (e.g., H3.1), and maternal nucleic acid may be associated with an unmethylated histone, such as, for example an unmethylated histone H1 or H3 (e.g., H3.1). Thus, a first histone-associated nucleic acid species can be a nucleic acid associated with an unmodified histone and a second histone-associated nucleic acid species can be a nucleic acid associated with a posttranslationally modified histone. Because fetal tissue can be enriched for histones comprising certain posttranslational modifications, separating some or substantially all of the first histone-associated nucleic acid species (i.e. nucleic acid associated with an unmodified histone) from the sample nucleic acid can deplete a proportion of maternal nucleic acid and generate a separation product enriched for fetal nucleic acid relative to fetal nucleic acid in the sample nucleic acid.

Separation methods that employ a binding agent, for example, can be used to deplete a particular histone-associated nucleic acid in a sample. In such methods, histone proteins (and the histone-associated nucleic acid) bound by the agent are separated away from the sample. A binding agent is an agent that specifically binds to a particular histone or histone variant. An agent "specifically binds" to a histone or histone variant if the binding agent binds preferentially to the histone or histone variant and, e.g., has less than about 30%, 20%, 10%, 5% or 1% cross-reactivity with another molecule. Methods for binding an agent to a histone or histone variant are described, for example, in US patent application publication nos. 2007/0243549 and 2010/0240054. Binding agents can be any binding agent known in the art or described herein, such as antibodies as described above. In some embodiments, the binding agent (e.g., antibody) is coupled to a solid support as described above. Such separation methods may include a lysis step to release nucleic acid contained in vesicles, in some embodiments. Methods for lysing vesicles are known in the art and generally include the use of a commercially available lysis buffer.

In some embodiments, the binding agent is specific for a particular histone or histone variant. Such histones or histone variants may include, for example, any histone protein, subtype, epitope, or isoform described herein or known in the art, each of which may include any of the posttranslational modifications described herein or known in the art or which may be unmodified. In some embodiments, the binding agent is specific for a histone originating from a maternal cell. In some embodiments, the binding agent is specific for a modified histone. In some embodiments, the binding agent is specific for a modified histone comprising a certain amount and/or combination of posttranslational modifications, such as, for example methylation, phosphorylation and/or acetylation. In some embodiments, the binding agent is specific for a methylated histone. In some embodiments, the binding agent is specific for an acetylated histone. In some embodiments, the binding agent is specific for a phosphorylated histone. In some embodiments, the binding agent is specific for an unmodified histone. In some embodiments, the binding agent is specific for an unmethylated histone. In some embodiments, the binding agent is specific for a non-acetylated histone. In some embodiments, the binding agent is specific for a non-phosphorylated histone. In some embodiments, the binding agent is specific for histone H3.3. In some embodiments, the binding agent is specific for histone H1b and/or H1(0).

In some embodiments, a sample can be enriched for a subpopulation of cell-free nucleic acid by the depletion of nucleic acid associated with a particular histone or histone variant. For example, a cell-free circulating sample nucleic acid from a biological sample can comprise a first histone-associated nucleic acid species and a second histone-associated nucleic acid species. Some or substantially all of the first histone-associated nucleic acid species can be separated from the sample nucleic acid, thereby generating a separation product enriched for the second histone-associated nucleic acid species. In some embodiments, the separation product comprises about 50% or greater of a second histone-associated nucleic acid species. For example, the separation product can comprise about 55%, 60%, 65%, 70%, 75%, 80%, 85%, 90%, 95% or 100% of a second histone-associated nucleic acid species. In some embodiments, fetal nucleic acid in the separation product is enriched relative to fetal nucleic acid in the sample nucleic acid. In some embodiments, fetal nucleic acid in the separation product can be enriched about 1.5-fold to about 20-fold relative to fetal nucleic acid in the sample nucleic acid. For example, fetal nucleic acid can be enriched about 2, 3, 4, 5, 6, 7, 8, 9, 10, or 15-fold.

Separation of Histone Associated Nucleic Acid Species

In some embodiments, a method comprises separating some or substantially all of a first histone-associated nucleic acid species from a second histone-associated nucleic acid species, thereby generating a separation product enriched for the second histone-associated nucleic acid species. In some embodiments, fetal nucleic acid in the separation product is enriched relative to fetal nucleic acid in the sample nucleic acid. In certain instances, circulating cell free fetal DNA can be associated with microparticles and nucleosomes (e.g., histone bound) that are derived from fetal tissue. In certain instances, circulating cell free maternal DNA can be associated with microparticles and nucleosomes (e.g., histone bound) that are derived from maternal tissue. Thus, in some embodiments, utilization of fetal source-specific binding agents (e.g., antibodies) to target fetal-derived microparticles and/or nucleosomes can enrich fetal DNA. In some embodiments, utilization of maternal source-specific binding agents (e.g., antibodies) to target maternal-derived microparticles and/or nucleosomes can enrich fetal DNA.

Nucleosome DNA typically is associated with an octamer of eight core histones: H2A (2), H2B (2), H3 (2), and H4 (2); and a linker histone H1. In maternal blood and cleared plasma, fetal ccf DNA may have a lower occupancy of H1 (i.e., a smaller percentage of the nucleosome DNA of fetal origin may have H1 bound, relative to the percentage of maternal ccf DNA having H1 bound). Without being limited by theory, the typical size distribution of fetal ccf DNA versus maternal ccf DNA is in accordance with this concept, since nucleosome DNA without H1 bound may be more susceptible to endonuclease digestion, thus resulting in shorter fragments.

In some embodiments, an agent that binds to histone H1 (e.g., without particular specificity to H1 subtypes or sources) is used as a tool for a negative selection approach to enrich for fetal DNA. Treatment of plasma with such an agent (e.g., antibody), for example, in an immunoprecipitation (e.g., Chromatin ImmunoPrecipitation (CHIP)) protocol can deplete maternal ccf DNA from the sample, thus enhancing ccf DNA fetal fraction in the residual sample.

In some embodiments, antibodies to fetal-specific histones (e.g., H1.1, H1.3, H1.5), are used to enrich fetal ccf DNA in certain positive selection approaches. In some embodiments, antibodies to maternal-specific histones (e.g., H1, H1.0), are used to enrich fetal ccf DNA in certain depletion-based entichment (i.e., negative selection) approaches. In some embodiments, antibodies to H1M histone (expressed in *Xenopus embryos*) and/or to H1FOO (which are expressed in oocytes) are used to enrich fetal ccf DNA in certain positive selection approaches. These approaches can include any suitable separation method described herein or known in the art such as conventional immunoprecipitation and Chromatin ImmunoPrecipitation (CHIP) approaches, for example.

There are approximately eleven H1 variants, some of which may be specific (or show preferential binding) to fetal-derived ccf DNA. Additionally, various maternal versus fetal differences in H3 histone subtype can be exploited to enrich for fetal fraction. For example, antibodies recognizing conformational exposure differences for histone H3.1 (e.g., differences between fetal and maternal H3.1) can be used for fetal DNA enrichment from plasma treated with such antibodies, in certain embodiments. For example, sequence variance (e.g., extra 10 amino acids at the c-terminus of fetal H3.1), and particular methylation of H3.1 in fetal versus maternal can be exploited for fetal DNA enrichment, in certain embodiments.

Methods for identifying certain antibodies (e.g., selective for fetal-derived histones and/or nucleosomes versus maternal-derived histones and/or nucleosomes) from commercial or elicited populations of antibodies, antibody fragments or aptamers are described in Example 1.

Enrichment of a Nucleic Acid Sub-Population

Methods provided herein can generate separation products that are enriched for a subpopulation of nucleic acid (e.g., enriched for a sub-population of cell-free nucleic acid). In certain embodiments, separation products can be enriched for vesicle-free nucleic acid by depletion vesicular nucleic acid. In some embodiments, a separation product comprises about 50% or greater vesicle-free nucleic acid. For example, a separation product can comprise about 55%, 60%, 65%, 70%, 75%, 80%, 85%, 90%, 95% or 100% vesicle-free nucleic acid. In some embodiments, some or substantially all vesicular nucleic acid is separated from sample nucleic acid, thereby generating a separation product enriched for vesicle-free nucleic acid.

In certain embodiments, a separation product can be enriched for histone-free nucleic acid by depletion of histone-associated nucleic acid. In some embodiments, a separation product comprises about 50% or greater histone-free nucleic acid. For example, a separation product can comprise about 55%, 60%, 65%, 70%, 75%, 80%, 85%, 90%, 95% or 100% histone-free nucleic acid. In some embodiments, some or substantially all histone-associated nucleic acid is separated from sample nucleic acid, thereby generating a separation product enriched for histone-free nucleic acid.

In some embodiments, a separation product is enriched for nucleic acid associated with a particular histone species or group of histone species. Nucleic acid associated with a particular histone species or group of histone species can be separated from histones, and consequently, a separation product sometimes is enriched for nucleic acid that was associated with a particular histone species or group of histone species. In certain embodiments, a separation product can be enriched for histone-associated nucleic acid by contacting sample nucleic acid with a binding agent that specifically binds to a particular histone species or group of histone species and separating nucleic acid associated with the agent (e.g., nucleic acid bound to the agent, or nucleic acid in a complex bound to the agent) from nucleic acid not bound to the agent. In some embodiments, a separation product comprises about 50% or greater histone-associated nucleic acid, or about 50% or greater nucleic acid that was in association with a particular histone species or group of histone species. For example, a separation product can comprise about 55%, 60%, 65%, 70%, 75%, 80%, 85%, 90%, 95% or 100% histone-associated nucleic acid or nucleic acid that was in association with a particular histone species or group of histone species. In some embodiments, some or substantially all of nucleic acid not associated with a particular histone species or group of histone species is separated from nucleic acid associated with, or was associated with, the particular histone species or group of histone species, thereby generating a separation product enriched for the histone-associated nucleic acid, or nucleic acid that was associated with the histone or group of histones.

In some embodiments, fetal nucleic acid in a separation product is enriched relative to fetal nucleic acid in sample nucleic acid. In certain embodiments, the relative proportion of (i) fetal nucleic acid to (ii) non-fetal nucleic acid is greater in the separation product than in the sample nucleic acid. For determining such a proportion, non-fetal nucleic acid sometimes is maternal nucleic acid, total histone-associated nucleic acid, total vesicle-associated nucleic acid or total nucleic acid (e.g., histone-associated nucleic acid and non-histone-associated nucleic acid; vesicle-associated nucleic acid and non-vesicle-associated nucleic acid). Fetal nucleic acid in a separation product sometimes is enriched 1.5-fold to 1,000-fold relative to fetal nucleic acid in sample nucleic acid (e.g., 20, 30, 40, 50, 60, 70, 80, 90, 100, 200, 300, 400, 500, 600, 700, 800 or 900-fold enriched). In some embodiments, fetal nucleic acid in the separation product can be enriched about 1.5-fold to about 20-fold relative to fetal nucleic acid in sample nucleic acid. For example, fetal nucleic acid can be enriched about 2, 3, 4, 5, 6, 7, 8, 9, 10, or 15-fold. In some embodiments, tumor-derived nucleic acid in a separation product is enriched relative to tumor-derived nucleic acid in sample nucleic acid. In some embodiments, nucleic acid derived from solid organ transplants in a separation product is enriched relative to nucleic acid derived from solid organ transplants in the sample nucleic acid.

In some embodiments, a nucleic acid sample can be further enriched for a particular subpopulation of cell-free nucleic acid by a method known in the art or described herein. For example, a nucleic acid sample can be further enriched for a particular subpopulation of cell-free nucleic acid by contacting nucleic acid that is substantially vesicle free with an agent that specifically binds to a histone associated with the vesicle-free nucleic acid. In certain embodiments, the histone is associated with a subpopulation of cell-free nucleic acid that is different from the enriched subpopulation of cell-free nucleic acid. For example, the histone can be associated with maternal cell-free nucleic acid. Methods for enriching a subpopulation of cell-free nucleic acid using histone binding agents are described in further detail herein.

A separation product containing fetal nucleic acid often contains fetal nucleic acid fragments. Fetal nucleic acid fragments in a separation product often range in size from about 50 base pairs to about 200 base pairs. The entire fetal genome or significant fraction of the fetal genome (e.g., 70% or more of the fetal genome) sometimes is represented in a separation product. Fetal nucleic acid fragments having the same length (e.g., 149 base pair fragment length or 150 base pair fragment length) in a separation product often represent a large number of sequences. There often are many fetal nucleic acid fragments having the same length but different sequences in a separation product. In some embodiments, about 1/15th of the fetal genome is represented by fetal nucleic acid fragments having the same length (e.g., 1/12th to 1/18th (e.g., 1/13th, 1/14th, 1/16th, 1/17th, 1/18th)). Fetal nucleic acid fragments having a particular length in a separation product often are from multiple and distinct regions of the genome. Some or all fetal nucleic acid fragments in a separation product often have sizes separated by one base pair (1-bp), where each fragment is 1-bp larger than the next shorter fragment.

Further Enrichment of Cell-Free Nucleic Acid

In some embodiments, nucleic acid (e.g., extracellular nucleic acid) is enriched or relatively enriched for a subpopulation or species of nucleic acid using a method described herein and one or more additional enrichment methods. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, fetal nucleic acid. In some embodiments, certain methods for determining fetal fraction described below also can be used to enrich for fetal nucleic acid. In certain embodiments, maternal nucleic acid is selectively removed (partially, substantially, almost completely or completely) from the sample. In some embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In some embodiments, nucleic acid is enriched for a specific nucleic acid fragment length or range of fragment lengths using one or more length-based separation methods described below. In some embodiments, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with a method described herein-include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In some embodiments, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with a method described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e., non-target) nucleic acid. In some embodiments, the method can be repeated for at least one additional cycle. In some embodiments, the same target-specific primer pair is used to prime each of the first and second cycles of extension, and in some embodiments, different target-specific primer pairs are used for the first and second cycles.

Some methods for enriching for a nucleic acid subpopulation (e.g., fetal nucleic acid) that can be used with a method described herein include massively parallel signature sequencing (MPSS) approaches. MPSS typically is a solid phase method that uses adapter (i.e., tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In some embodiments, certain MPSS-based enrichment methods can include amplification (e.g., PCR)-based approaches. In some embodiments, loci-specific amplification methods can be used (e.g., using loci-specific amplification primers). In some embodiments, a multiplex SNP allele PCR approach can be used. In some embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In some embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In some embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In some embodiments, a microfluidics approach can be used. In some embodiments, an array-based microfluidics approach can be used. For example, such an approach can involve the use of a microfluidics array (e.g., Fluidigm) for amplification at low plex and incorporation of index and capture probes, followed by sequencing. In some embodiments, an emulsion microfluidics approach can be used, such as, for example, digital droplet PCR.

In some embodiments, universal amplification methods can be used (e.g., using universal or non-loci-specific amplification primers). In some embodiments, universal amplification methods can be used in combination with pull-down approaches. In some embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In some embodiments, pull-down approaches can be used in combination with ligation-based methods. In some embodiments, a method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In some embodiments, pull-down approaches can be used in combination with extension and ligation-based methods. In some embodiments, a method can include molecular inversion probe (MIP) extension and ligation. For example, such an approach can involve the use of molecular inversion probes in combination with sequence adapters followed by universal amplification and sequencing. In some embodiments, complementary DNA can be synthesized and sequenced without amplification.

In some embodiments, extension and ligation approaches can be performed without a pull-down component. In some embodiments, a method can include loci-specific forward and reverse primer hybridization, extension and ligation. Such methods can further include universal amplification or complementary DNA synthesis without amplification, followed by sequencing. Such methods can reduce or exclude background sequences during analysis, in some embodiments.

In some embodiments, pull-down approaches can be used with an optional amplification component or with no amplification component. In some embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In some embodiments, a method can include a biotinylated pull-down assay with extension and ligation of adaptor sequence in combination with circular single stranded ligation. For example, such an approach can involve the use of selector probes to capture regions of interest (i.e., target sequences), extension of the probes, adaptor ligation, single stranded circular ligation, optional amplification, and sequencing. In some embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments typically are isolated away from the remaining fragments in the nucleic acid sample. In some embodiments, the separated target fragments and the separated reference fragments also are isolated away from each other (e.g., isolated in separate assay compartments). In some embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome).

In some embodiments, nucleic acid is enriched for a particular nucleic acid fragment length, range of lengths, or lengths under or over a particular threshold or cutoff using one or more length-based separation methods. For example, isolated cell-free nucleic having fragment lengths of about 300 base pairs or less, about 200 base pairs or less or about 150 base pairs or less can be enriched for fetal nucleic acid, in certain instances. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In some embodiments, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. The term "sequence tagging" refers to incorporating a recognizable and distinct sequence into a nucleic acid or population of nucleic acids. The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In some embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequence's, and the enriched short fragments can be used for further analysis.

Determining Fetal Nucleic Acid Content

The amount of fetal nucleic acid (e.g., concentration, relative amount, absolute amount, copy number, and the like) in nucleic acid is determined in some embodiments. In some embodiments, the amount of fetal nucleic acid in a sample is referred to as "fetal fraction". In some embodiments, "fetal fraction" refers to the fraction of fetal nucleic acid in circulating cell-free nucleic acid in a sample (e.g., a blood sample, a serum sample, a plasma sample) obtained from a pregnant female. In some embodiments, a method in which a genetic variation is determined also can comprise determining fetal fraction. Determining fetal fraction can be performed in a suitable manner, non-limiting examples of which include methods described below.

In some embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. The amount of fetal nucleic acid from a maternal sample sometimes can be determined relative to the total amount of nucleic acid present, thereby providing the percentage of fetal nucleic acid in the sample. The copy number of fetal nucleic acid sometimes can be determined in a maternal sample. The amount of fetal nucleic acid sometimes can be determined in a sequence-specific (or locus-specific) manner and sometimes with sufficient sensitivity to allow for accurate chromosomal dosage analysis (for example, to detect the presence or absence of a fetal aneuploidy or other genetic variation).

A fetal quantifier assay (FQA) can be performed in conjunction with any method described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-

28); methylation specific antibodies; bisulfate conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In some embodiments, the restriction efficiency can be determined and the efficiency rate is used to further determine the amount of fetal DNA.

A fetal quantifier assay (FQA) sometimes can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. The absolute copy number of fetal nucleic acid in a maternal sample sometimes can be determined, for example, using mass spectrometry and/or a system that uses a competitive PCR approach for absolute copy number measurements. See for example, Ding and Cantor (2003) Proc. Natl. Acad. Sci. USA 100:3059-3064, and U.S. Patent Application Publication No. 2004/0081993, both of which are hereby incorporated by reference.

Fetal fraction sometimes can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. Fetal alleles can be identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination step can be performed before, during, at any one point in a method described herein, or after certain (e.g., aneuploidy detection) methods described herein. For example, to achieve an aneuploidy determination method with a given sensitivity or specificity, a fetal nucleic acid quantification method may be implemented prior to, during or after aneuploidy determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for the presence or absence of aneuploidy or genetic variation, for example. In certain embodiments, determinations of, for example, the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy. In some embodiments, identifying the presence or absence of a chromosome aneuploidy does not require the sequence differentiation of fetal versus maternal DNA. This is because the summed contribution of both maternal and fetal sequences in a particular chromosome, chromosome portion or segment thereof is analyzed, in some embodiments. In some embodiments, identifying the presence or absence of a chromosome aneuploidy does not rely on a priori sequence information that would distinguish fetal DNA from maternal DNA.

Obtaining Sequence Reads

Sequence reads can be obtained from enriched samples. Sequencing, mapping and related analytical methods are known in the art (e.g., United States Patent Application Publication US2009/0029377, incorporated by reference). Certain aspects of such processes are described hereafter.

As used herein, "reads" are short nucleotide sequences produced by any sequencing process described herein or known in the art. Reads can be generated from one end of nucleic acid fragments ("single-end reads"), and sometimes are generated from both ends of nucleic acids ("double-end reads"). In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a fraction of a nucleic acid pool that is sequenced in a run is further sub-selected prior to sequencing. In certain embodiments, hybridization-based techniques (e.g., using oligonucleotide arrays) can be used to first sub-select for nucleic acid sequences from certain chromosomes (e.g., a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected pool of nucleic acids is sequenced randomly. In some embodiments, the nucleic acid is amplified prior to sequencing. In some embodiments, a portion or subset of the nucleic acid is amplified prior to sequencing.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" representing an individual clonal DNA template or a single DNA molecule. High-throughput sequencing technologies include, for example, sequencing-by-synthesis with reversible dye terminators, sequencing by oligonucleotide probe ligation, pyrosequencing and real time sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in the methods provided herein. Additional sequencing technologies that include the use of developing nucleic acid imaging technologies (e.g. transmission electron microscopy (TEM) and atomic force microscopy (AFM)), are also contemplated herein. Examples of various sequencing technologies are described below.

A nucleic acid sequencing technology that may be used in the methods described herein is sequencing-by-synthesis and reversible terminator-based sequencing (e.g. Illumina's Genome Analyzer and Genome Analyzer II). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors. Template DNA often is fragmented into lengths of several hundred base pairs and end-repaired to generate 5'-phosphorylated blunt ends and a single adenine (A) base is then added to the 3' end of the blunt phosphorylated DNA fragments. This addition prepares the DNA fragments for ligation to oligonucleotide adapters, which have an overhang of a single thymine (T) base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. In contrast to emulsion PCR, DNA templates are amplified in the flow cell by "bridge" amplification, which relies on captured DNA strands "arching" over and hybridizing to an adjacent anchor oligonucleotide. Multiple amplification cycles convert the single-molecule DNA template to a clonally amplified arching "cluster," with each cluster containing approximately 1000 clonal molecules. Approximately $50 \times 10^6$ separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adapter sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With $50 \times 10^6$ clusters per flow cell, the overall sequence output can be greater than 1 billion base pairs (Gb) per analytical run.

Another nucleic acid sequencing technology that may be used with the methods described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA)

is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in the methods provided herein is Applied Biosystems' SOLiD™ technology. In SOLiD™ sequencing-by-ligation, a library of nucleic acid fragments is prepared from the sample and is used to prepare clonal bead populations. With this method, one species of nucleic acid fragment will be present on the surface of each bead (e.g. magnetic bead). Sample nucleic acid (e.g. genomic DNA) is sheared into fragments, and adaptors are subsequently attached to the 5' and 3' ends of the fragments to generate a fragment library. The adapters are typically universal adapter sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adapter sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1.

Another nucleic acid sequencing technology that may be used in the methods described herein is the Helicos True Single Molecule Sequencing (tSMS). In the tSMS technique, a polyA sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in the methods provided herein is the single molecule, real-time (SMRT™) sequencing technology of Pacific Biosciences. With this method, each of the four DNA bases Is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Another nucleic acid sequencing technology that may be used in the methods described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in the methods described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Publication No. 2009/0026082).

Another nucleic acid sequencing technology that may be used in the methods described herein is electron microscopy. In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M. Proc Natl Acad Sci USA. 1965 March; 53:564-71). In some instances, transmission electron microscopy (TEM) is used (e.g. Halcyon Molecular's TEM method). This method, termed Individual Molecule Placement Rapid Nano Transfer (IMPRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA (see, for example, PCT patent publication WO 2009/046445).

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in the methods described herein. Nanopore sequencing is a single-molecule sequencing technology whereby a single nucleic acid molecule (e.g. DNA) is sequenced directly as it passes through a nanopore. A nanopore is a small hole or channel, of the order of 1 nanometer in diameter. Certain transmembrane cellular proteins can act as nanopores (e.g. alpha-hemolysin). Nanopores sometimes can be synthesized (e.g. using a silicon platform). Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or in some instances, methyl-C. The change in the current through the nanopore as the DNA molecule passes through the nanopore represents a direct reading of the DNA sequence. In some instances a nanopore can be used to identify individual DNA bases as they pass through the nanopore in the correct order (see, for example, Soni G V and Meller A. Clin Chem 53: 1996-2001 (2007); PCT publication no. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. In some instances, the exonuclease enzyme can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling the target nucleic acid through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g. about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp or more.

In some embodiments, nucleic acids may include a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Mapping Reads

Mapping nucleotide sequence reads (i.e., sequence information from a fragment whose physical genomic position is unknown) can be performed in a number of ways, and often comprises alignment of the obtained sequence reads with a matching sequence in a reference genome (e.g., Li et al., "Mapping short DNA sequencing reads and calling variants using mapping quality score," Genome Res., 2008 Aug. 19.) In such alignments, sequence reads generally are aligned to a reference sequence and those that align are designated as being "mapped" or a "sequence tag." In some embodiments, a mapped sequence read is referred to as a "hit". In some embodiments, mapped sequence reads are grouped together according to various parameters and assigned to particular genome sections, which are discussed in further detail below.

Various computational methods can be used to map each sequence read to a genome section. Non-limiting examples of computer algorithms that can be used to align sequences include BLAST, BLITZ, and FASTA, or variations thereof. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate genome sections (described hereafter), for example.

A "sequence tag" is a nucleic acid (e.g. DNA) sequence (i.e. read) assigned specifically to a particular genome section and/or chromosome (i.e. one of chromosomes 1-22, X or Y for a human subject). A sequence tag may be repetitive or non-repetitive within a single portion of the reference genome (e.g., a chromosome). In some embodiments, repetitive sequence tags are eliminated from further analysis (e.g. quantification). In some embodiments, a read may uniquely or non-uniquely map to portions in the reference genome. A read is considered "uniquely mapped" if it aligns with a single sequence in the reference genome. A read is considered "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, a reference sequence or reference genome often is an assembled or partially assembled genomic sequence from an individual or multiple individuals. In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

Genome Sections

In some embodiments, mapped sequence reads (i.e. sequence tags) are grouped together according to various parameters and assigned to particular genome sections. Often, the individual mapped sequence reads can be used to identify an amount of a genome section present in a sample. In some embodiments, the amount of a genome section can be indicative of the amount of a larger sequence (e.g. a chromosome) in the sample. The term "genome section" can also be referred to herein as "sequence window", "section", "bin", "locus", "region", "partition" or "segment". In some embodiments, a genome section is an entire chromosome, portion of a chromosome, multiple chromosome portions, multiple chromosomes, portions from multiple chromosomes, and/or combinations thereof. In some embodiments, a genome section is delineated based on one or more parameters which include, for example, length or a particular feature or features of the sequence. In some embodiments, a genome section is based on a particular length of genomic sequence. In some embodiments, the methods include analysis of multiple mapped sequence reads to a plurality of genome sections. The genome sections can be approximately the same length or the genome sections can be different lengths. In some embodiments, a genome section is about 10 kilobases (kb) to about 100 kb, about 20 kb to about 80 kb, about 30 kb to about 70 kb, about 40 kb to about 60 kb, and sometimes about 50 kb. In some embodiments, the genome section is about 10 kb to about 20 kb. The genomic sections discussed herein are not limited to contiguous runs of sequence. Thus, genome sections can be made up of contiguous or non-contiguous sequences. The genomic sections discussed herein are not limited to a single chromosome and, in some embodiments, may transcend individual chromosomes. In some embodiments, genomic sections may span one, two, or more entire chromosomes. In addition, the genomic sections may span joint or disjoint portions of multiple chromosomes.

In some embodiments, genome sections can be particular chromosome sections in a chromosome of interest, such as, for example, chromosomes where a genetic variation is assessed (e.g. an aneuploidy of chromosomes 13, 18 and/or 21). A genome section can also be a pathogenic genome (e.g. bacterial, fungal or viral) or fragment thereof. Genome sections can be genes, gene fragments, regulatory sequences, introns, exons, and the like.

In some embodiments, a genome (e.g. human genome) is partitioned into genome sections based on the information content of the regions. The resulting genomic regions may contain sequences for multiple chromosomes and/or may contain sequences for portions of multiple chromosomes.

In some embodiments, the partitioning may eliminate similar locations across the genome and only keep unique regions. The eliminated regions may be within a single chromosome or may span multiple chromosomes. The resulting genome is thus trimmed down and optimized for faster alignment, often allowing for focus on uniquely identifiable sequences. In some embodiments, the partitioning may down weight similar regions. The process for down weighting a genome section is discussed in further detail below. In some embodiments, the partitioning of the genome into regions transcending chromosomes may be based on information gain produced in the context of classification. For example, the information content may be quantified using the p-value profile measuring the significance of particular genomic locations for distinguishing between groups of confirmed normal and abnormal subjects (e.g. euploid and trisomy subjects). In some embodiments, the partitioning of the genome into regions transcending chromosomes may be based on any other criterion, such as, for example, speed/convenience while aligning tags, high or low GC content, uniformity of GC content, other measures of sequence content (e.g. fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, level of uncertainty assigned to individual bins, and/or a targeted search for particular features.

Outcomes and Determination of the Presence or Absence of a Genetic Variation

Some genetic variations are associated with medical conditions. Genetic variations often include a gain, a loss, and/or alteration (e.g., reorganization or substitution) of genetic information (e.g., chromosomes, portions of chromosomes, polymorphic regions, translocated regions, altered nucleotide sequence, the like or combinations of the foregoing) that result in a detectable change in the genome or genetic information of a test subject with respect to a reference subject free of the genetic variation. The presence or absence of a genetic variation can be determined by analyzing and/or manipulating sequence reads that have been mapped to genomic sections (e.g., genomic bins) as described herein.

Counting

Sequence reads that have been mapped or partitioned based on a selected feature or variable can be quantified to determine the number of reads that were mapped to each genomic section (e.g., bin, partition, genomic segment and the like), in some embodiments. In certain embodiments, the total number of mapped sequence reads is determined by counting all mapped sequence reads, and in some embodiments the total number of mapped sequence reads is determined by summing counts mapped to each bin or partition. In certain embodiments, a subset of mapped sequence reads is determined by counting a predetermined subset of mapped sequence reads, and in some embodiments a predetermined subset of mapped sequence reads is determined by summing counts mapped to each predetermined bin or partition. In some embodiments, predetermined subsets of mapped sequence reads can include from 1 to n−1 sequence reads, where n represents a number equal to the sum of all sequence reads generated from a test subject or reference subject sample. In certain embodiments, predetermined subsets of mapped sequence reads can be selected utilizing any suitable feature or variable.

Quantifying or counting sequence reads can be done in any suitable manner including but not limited to manual counting methods and automated counting methods. In some embodiments, an automated counting method can be embodied in software that determines or counts the number of sequence reads or sequence tags mapping to each chromosome and/or one or more selected genomic sections. As used herein, software refers to computer readable program instructions that, when executed by a computer, perform computer operations.

The number of sequence reads mapped to each bin and the total number of sequence reads for samples derived from test subject and/or reference subjects can be further analyzed and processed to provide an outcome determinative of the presence or absence of a genetic variation. Mapped sequence reads that have been counted sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, genomic section or bin specific], the like and combinations thereof). In certain embodiments, data or data sets can be organized into a matrix having two or more dimensions based on one or more features of variables. Data organized into matrices can be stratified using any suitable features or variables. A non-limiting example of data organized into a matrix includes data that is stratified by maternal age, maternal ploidy, and fetal contribution. In certain embodiments, data sets characterized by one or more features or variables sometimes are processed after counting.

Data Processing

Mapped sequence reads that have been counted are referred to herein as raw data, since the data represent unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative genomic sections or bins (e.g., bins with uninformative data, redundant mapped reads, genomic sections or bins with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "preprocessing" and "processing" when utilized with respect to data or data sets are collectively referred to herein as "processing". Processing can render data more amenable to further analysis, and can generate an outcome in some embodiments.

The term "noisy data" as used herein refers to (a) data that has a significant variance between data points when analyzed or plotted, (b) data that has a significant standard deviation, (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative bins", and "uninformative genomic sections" as used herein refer to genomic sections, or data derived therefrom, having a numerical value that is significantly different from a predetermined cutoff threshold value or falls outside a predetermined cutoff range of values. A cutoff threshold value or range of values often is calculated by mathematically and/or statistically manipulating sequence read data (e.g., from a reference and/or subject), in some embodiments, and in certain embodiments, sequence read data manipulated to generate a threshold cutoff value or range of values is sequence read data (e.g., from a reference and/or subject). In some embodiments, a threshold cutoff value is obtained by calculating the standard deviation and/or median absolute deviation (e.g., MAD) of a raw or normalized count profile and multiplying the standard deviation for the profile by a constant representing the number of standard deviations chosen as a cutoff threshold (e.g., multiply by 3 for 3 standard deviations), whereby a value for an uncertainty is generated. In certain embodiments, a portion or all of the genomic sections exceeding the calculated uncertainty threshold cutoff value, or outside the range of threshold cutoff values, are removed as part of, prior to, or after the normalization process. In some embodiments, a portion or all of the genomic sections exceeding the calculated uncertainty threshold cutoff value, or outside the range of threshold cutoff values or raw data points, are weighted as part of, or prior to the normalization or classification process. Examples of weighting are described herein. The terms "redundant data", and "redundant mapped reads" as used herein refer to sample derived sequences reads that are identified as having already been assigned to a genomic location (e.g., base position) and/or counted for a genomic section.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set. In some embodiments, one or more processing steps can comprise one or more filtering steps.

The term "filtering" as used herein refers to removing genomic sections or bins from consideration. Bins can be selected for removal based on any suitable criteria, including but not limited to redundant data (e.g., redundant or overlapping mapped reads), non-informative data (e.g., bins with zero median counts), bins with over represented or under represented sequences, noisy data, the like, or combinations of the foregoing. A filtering process often involves removing one or more bins from consideration and subtracting the counts in the one or more bins selected for removal from the counted or summed counts for the bins, chromosome or chromosomes, or genome under consideration. In some embodiments, bins can be removed successively (e.g., one at a time to allow evaluation of the effect of removal of each individual bin), and in certain embodiments all bins marked for removal can be removed at the same time.

In some embodiments, one or more processing steps can comprise one or more normalization steps. The term "normalization" as used herein refers to division of one or more data sets by a predetermined variable. Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference genomic sections to the total number of counts mapped to the chromosome or the entire genome on which the selected genomic section or sections are mapped; normalizing raw count data for one or more selected genomic segments to a median reference count for one or more genomic sections or the chromosome on which a selected genomic segment or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more genomic sections or bins, based on the quality or usefulness of the data in the selected bin or bins). A weighting function can be used to increase the influence of data with a relatively small measurement variance, and/or to decrease the influence of data with a relatively large measurement variance, in some embodiments. For example, bins with under represented or low quality sequence data can be "down weighted" to minimize the influence on a data set, whereas selected bins can be "up weighted" to increase the influence on a data set. A non-limiting example of a weighting function is [1/(standard deviation)$^2$]. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak elevations, determination of peak edge locations, calculation of peak area ratios, analysis of median chromosomal elevation, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median elevations, mean elevations, count distribution within a genomic region, relative representation of nucleic acid species, the like or combinations thereof.

In some embodiments, a processing step can include the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median elevations, mean elevations, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to mathematical and/or statistical manipulation of data that facilitates identification of patterns and/or correlations in large quantities of data. Thus, the term "profile" as used herein often refers to values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a portion or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a genomic section. In certain embodiments, a data point in a profile represents the results of data manipulation for groups of genomic sections. In some embodiments, groups of genomic sections may be adjacent to one another, and in certain embodiments, groups of genomic sections may be from different parts of a chromosome or genome.

Data points in a profile derived from a data set can be representative of any suitable data categorization. Non-limiting examples of categories into which data can be grouped to generate profile data points include: genomic sections based on sized, genomic sections based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile frequently is presented as a plot, and non-limiting examples of profile plots that can be generated include raw count (e.g., raw count profile or raw profile), normalized count (e.g., normalized count profile or normalized profile), bin-weighted, z-score, p-value, area ratio versus fitted ploidy, median elevation versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median elevation versus ratio between fitted and measured fetal fraction, principle components). The terms "raw count profile plot" or "raw profile plot" as used herein refer to a plot of counts in each genomic section in a region normalized to total counts in a region (e.g., genome, chromosome, portion of chromosome).

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected genomic section is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, genomic sections or portions thereof from a set of references known not to carry a genetic variation, (b) removal of uninformative genomic sections from the reference sample raw counts (e.g., filtering); (c) normalizing the reference counts for all remaining bins to the total residual number of counts (e.g., sum of remaining counts after removal of uninformative bins) for the reference sample selected chromosome or selected genomic location, thereby generating a normalized reference subject profile; (d) removing the corresponding genomic sections from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered genomic sections in (b), can be included between (c) and (d).

In some embodiments, the use of one or more reference samples known to be free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected genomic section or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected genomic section or sections is expected to vary significantly from the predetermined value for affected genomic locations.

In some embodiments, analysis and processing of data can include the use of one or more assumptions. Any suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion or genomic deletion; represent the presence or absence of a variation in the physical amount of a sequence associated with medical conditions). A virtual representation sometimes is further transformed into one or more numerical values or graphical representations of the digital representation of the starting material. These procedures can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). Any suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Outcome

Analysis and processing of data can provide one or more outcomes. The term "outcome" as used herein refers to a result of data processing that facilitates determining whether a subject was, or is at risk of having, a genetic variation. An outcome often comprises one or more numerical values generated using a processing method described herein in the context of one or more considerations of probability. A consideration of probability includes but is not limited to: measure of variability, confidence level, sensitivity, specificity, standard deviation, coefficient of variation (CV) and/or confidence level, Z-scores, Chi values, Phi values, ploidy values, fitted fetal fraction, area ratios, median elevation, the like or combinations thereof. A consideration of probability can facilitate determining whether a subject is at risk of having, or has, a genetic variation, and an outcome determinative of a presence or absence of a genetic disorder often includes such a consideration.

An outcome often is a phenotype with an associated level of confidence (e.g., fetus is positive for trisomy 21 with a confidence level of 99%, test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or genomic section from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises a profile. In those embodiments in which an outcome comprises a profile, any suitable profile or combination of profiles can be used for an outcome.

Non-limiting examples of profiles that can be used for an outcome include z-score profiles, p-value profiles, chi value profiles, phi value profiles, the like, and combinations thereof An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in any suitable form, which form comprises without limitation, a probability (e.g., odds ratio, value), likelihood, value in or out of a cluster, value over or under a threshold value, value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. An outcome also can describe any assumptions used in data processing. In certain embodiments, an outcome comprises a value that falls within or outside a predetermined range of values and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative. The term "sensitivity" as used herein refers to the number of true positives divided by the number of true positives plus the number of false negatives, where sensitivity (sens) may be within the range of $0 \leq sens \leq 1$. Ideally, the number of false negatives equal zero or close to zero, so that no subject is wrongly identified as not having at least one genetic variation when they indeed have at least one genetic variation. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of $0 \leq spec \leq 1$. Ideally, the number of false positives equal zero or close to zero, so that no subject is wrongly identified as having at least one genetic variation when they do not have the genetic variation being assessed.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein.

A method that has sensitivity and specificity equaling one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

After one or more outcomes have been generated, an outcome often is used to provide a determination of the presence or absence of a genetic variation and/or associated medical condition. An outcome typically is provided to a health care professional (e.g., laboratory technician or manager; physician or assistant). In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in any suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph; and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by any communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by any other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and' grammatical equivalents thereof, as used herein also can refer to any method for obtaining such information, including, without limitation, obtaining the information from a laboratory file. A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

A healthcare professional or qualified individual, can provide any suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Software can be used to perform one or more steps in the process described herein, including but not limited to; counting, data processing, generating an outcome, and/or providing one or more recommendations based on generated outcomes.

Machines, Software and Interfaces

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by any suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, any suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by any suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., data acquisition module, data processing module, data display module). The term "software" refers to computer readable program instructions that, when executed by a computer, perform computer operations. The term "module" refers to a self-contained functional unit that can be used in a larger software system. For example, a software module is a part of a program that performs a particular process or task.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software.

Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a computer usable medium having a computer readable program code embodied therein, the computer readable program code adapted to be executed to implement a method comprising: (a) obtaining nucleotide sequence reads from a sample comprising circulating, cell-free nucleic acid from a pregnant female, where the sample has been enriched for vesicle-free and/or a certain histone-associated nucleic acid species, (b) mapping the nucleotide sequence reads to reference genome sections, (c) counting the number of nucleotide sequence reads mapped to each reference genome section, (d) comparing the number of counts of the nucleotide sequence reads mapped in (c), or derivative thereof, to a reference, or portion thereof, thereby making a comparison, and (e) providing an outcome determinative of the presence or absence of a fetal aneuploidy based on the comparison.

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for providing an outcome determinative of the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interface's that allow software and data to be transferred from the removable storage unit to a computer system.

Genetic Variations and Medical Conditions

The presence or absence of a genetic variance can be determined using a method or apparatus described herein. In certain embodiments, the presence or absence of one or more genetic variations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In some embodiments, a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In some embodiments, a duplication is a mutation (e.g., a genetic aberration) in which a part of a chromosome or a sequence of DNA is copied and inserted back into the genome. In some embodiments, a genetic duplication (i.e. duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In some embodiments, an insertion comprises the addition of a segment of a chromosome into a genome, chromosome, or segment thereof. In some embodiments, an insertion comprises the addition of an allele, a gene, an intron, an exon, any non-coding region, any coding region, segment thereof or combination thereof into a genome or segment thereof. In some embodiments, an insertion comprises the addition (i.e., insertion) of nucleic acid of unknown origin into a genome, chromosome, or segment thereof. In some embodiments, an insertion comprises the addition (i.e. insertion) of a single base.

As used herein a "copy number variation" generally is a class or type of genetic variation or chromosomal aberration. A copy number variation can be a deletion (e.g. microdeletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In some embodiments, a duplication comprises an insertion. In some embodiments, an insertion is a duplication. In some embodiments, an insertion is not a duplication. For example, often a duplication of a sequence in a genomic section increases the counts for a genomic section in which the duplication is found. Often a duplication of a sequence in a genomic section increases the elevation. In some embodiments, a duplication present in genomic sections making up a first elevation increases the elevation relative to a second elevation where a duplication is absent. In some embodiments, an insertion increases the counts of a genomic section and a sequence representing the insertion is present (i.e., duplicated) at another location within the same genomic section. In some embodiments, an insertion does not significantly increase the counts of a genomic section or elevation and the sequence that is inserted is not a duplication of a sequence within the same genomic section. In some embodiments, an insertion is not detected or represented as a duplication and a duplicate sequence representing the insertion is not present in the same genomic section.

In some embodiments a copy number variation is a fetal copy number variation. Often, a fetal copy number variation is a copy number variation in the genome of a fetus. In some embodiments a copy number variation is a maternal copy number variation. In some embodiments, a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" refers to the number of chromosomes present in a fetus or mother. In some embodiments, "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid. "Microploidy" is similar in meaning to ploidy. "Microploidy" often refers to the ploidy of a segment of a chromosome. The term "microploidy" sometimes refers to the presence or absence of a copy number variation (e.g., a deletion, duplication and/or an insertion) within a chromosome (e.g., a homozygous or heterozygous deletion, duplication, or insertion, the like or absence thereof). "Ploidy" and "microploidy" sometimes are determined after normalization of counts of an elevation in a profile (e.g., after normalizing counts of an elevation to an NRV of 1). Thus, an elevation representing an autosomal chromosome pair (e.g., a euploid) is often normalized to an NRV of 1 and is referred to as a ploidy of 1. Similarly, an elevation within a segment of a chromosome representing the absence of a duplication, deletion or insertion is often normalized to an NRV of 1 and is referred to as a microploidy of 1. Ploidy and microploidy are often bin-specific (e.g., genomic section specific) and sample-specific. Ploidy is often defined as integral multiples of ½, with the values of 1, ½, 0, 3/2, and 2 representing euploidy (e.g., 2 chromosomes), 1 chromosome present (e.g., a chromosome deletion), no chromosome present, 3 chromosomes (e.g., a trisomy) and 4 chromosomes, respectively. Likewise, microploidy is often defined as integral multiples of ½, with the values of 1, ½, 0, 3/2, and 2 representing euploidy (e.g., no copy number variation), a heterozygous deletion, homozygous deletion, heterozygous duplication and homozygous duplication, respectively.

In some embodiments, the microploidy of a fetus matches the microploidy of the mother of the fetus (i.e., the pregnant female subject). In some embodiments, the microploidy of a fetus matches the microploidy of the mother of the fetus and both the mother and fetus carry the same heterozygous copy number variation, homozygous copy number variation or both are euploid. In some embodiments, the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A microploidy is often associated with an expected elevation. For example, sometimes an elevation (e.g., an elevation in a profile, sometimes an elevation that includes substantially no copy number variation) is normalized to an NRV of 1 and the microploidy of a homozygous duplication is 2, a heterozygous duplication is 1.5, a heterozygous deletion is 0.5 and a homozygous deletion is zero.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of a fetal gender or gender related disorder (e.g., sex chromosome aneuploidy) can be determined by a method or apparatus described herein. In some embodiments, a method in which fetal gender is determined can also comprise determining fetal fraction and/or presence or absence of a fetal genetic variation (e.g., fetal chromosome aneuploidy). Determining presence or absence of a fetal genetic variation can be performed in a suitable manner, non-limiting examples of which include karyotype analysis, amniocentesis, circulating cell-free nucleic acid analysis, cell-free fetal DNA analysis, nucleotide sequence analysis, sequence read quantification, targeted approaches, amplification-based approaches, mass spectrometry-based approaches, differential methylation-based approaches, differential digestion-based approaches, polymorphism-based approaches, hybridization-based approaches (e.g., using probes), and the like.

Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include XO, XYY, XXX and XXY. In some instances, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (XO; Turner Syndrome). In some instances, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenital, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjrg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinits pigmentosa, and azoospermia.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations. The terms "aneuploidy" and "aneuploid" as used herein refer to an abnormal number of chromosomes in cells of an organism.

As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example.

The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "euploid", in some embodiments, refers a normal complement of chromosomes.

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods and apparatus described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |

TABLE 1A-continued

| Chromosome | Abnormality | Disease Association |
|---|---|---|
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobson Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL |
| 16 | 16q13.3 deletion monosomy trisomy (somatic) | Rubenstein-Taybi papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |

TABLE 1B-continued

| Syndrome | Chromosome | Start | End | Interval (Mb) | Grade |
|---|---|---|---|---|---|
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population;

functional data confirming single gene or multi-gene dosage effect; confirmed or strong candidate genes; clinical management implications defined; known cancer risk with implication for surveillance; multiple sources of information (OMIM, GeneReviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method or apparatus described herein. Preeclampsia is a condition in which hypertension arises in pregnancy (i.e. pregnancy-induced hypertension) and is associated with significant amounts of protein in the urine. In some instances, preeclampsia also is associated with elevated levels of extracellular nucleic acid and/or alterations in methylation patterns. For example, a positive correlation between extracellular fetal-derived hypermethylated RASSF1A levels and the severity of preeclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

EXAMPLES

The examples set forth below illustrate certain embodiments and do not limit the technology.

Example 1: Capture of nucleosomes to enhance fetal fraction

In this example, a process is described for enriching the amount of fetal derived DNA relative to total derived (maternal+fetal) DNA, also expressed as fetal fraction, in plasma samples. DNA prepared from plasma is often referred to as circulating cell-free DNA (ccf DNA), as described herein. Circulating cell-free DNA can exist in multiple states within whole blood. DNA can be naked, histone bound (i.e., nucleosomes containing DNA and histones), or encapsulated in a lipid bilayer as a microparticle (for example, in an apoptotic structure). Circulating cell free fetal DNA can be associated with microparticles and nucleosomes (e.g., histone bound) that are derived from fetal tissue. Circulating cell free maternal DNA can be associated with microparticles and nucleosomes (histone bound) that are derived from maternal tissue. Thus, utilization of fetal source-specific antibodies to target fetal-derived microparticles and/or nucleosomes can enrich fetal DNA. This example describes a process for specifically enriching for circulating cell free fetal DNA associated nucleosomes (histone bound).

Nucleosome DNA typically is associated with an octamer of eight core histones: H2A (2), H2B (2), H3 (2), and H4 (2); and a linker histone H1. In maternal blood and cleared plasma, fetal ccf DNA may have a lower occupancy of H1 (i.e., a smaller percentage of the nucleosome DNA of fetal origin may have H1 bound, relative to the percentage of maternal ccf DNA having H1 bound). Without being limited by theory, the typical size distribution of fetal ccf DNA versus maternal ccf DNA is in accordance with this concept, since nucleosome DNA without H1 bound may be more susceptible to endonuclease digestion, thus resulting in shorter fragments.

Use of an antibody to histone H1 (e.g., without particular specificity to H1 subtypes or sources) can serve as a suitable negative selection approach to enrich for fetal DNA. Treatment of plasma with such antibody in an immunoprecipitation (e.g., Chromatin ImmunoPrecipitation (CHIP)) protocol can deplete maternal ccf DNA from the sample, thus enhancing ccf DNA fetal fraction in the residual sample.

Antibodies to fetal-specific histones (e.g., H1.1, H1.3, H1.5), can enrich fetal ccf DNA when used in positive selection approaches. Antibodies to maternal-specific histones (e.g., H1.0), can enrich fetal ccf DNA when used in depletion-based enrichment (i.e., negative selection) approaches. These approaches can include, conventional immunoprecipitation and Chromatin ImmunoPrecipitation (CHIP) approaches. Antibodies to H1M histone (expressed in *Xenopus embryos*) and to H1FOO (which are expressed in oocytes) may offer some cross reactivity and selectivity to human fetal-derived chromatin DNA, and thus also may be used as a positive selection strategy.

There are approximately eleven H1 variants, some of which may be specific (or show preferential binding) to fetal-derived ccf DNA. Additionally, various maternal versus fetal differences in H3 histone subtype can be exploited to enrich for fetal fraction. For example, antibodies recognizing conformational exposure differences for histone H3.1 (e.g., differences between fetal and maternal H3.1) can be used for fetal DNA enrichment from plasma treated with such antibodies. For example, sequence variance (e.g., extra 10 amino acids at the c-terminus of fetal H3.1), and particular methylation of H3.1 in fetal versus maternal can be exploited for fetal DNA enrichment.

Methods for identifying certain antibodies (e.g., selective for fetal-derived nucleosomes versus maternal-derived nucleosomes) from commercial or elicited populations of antibodies, antibody fragments or aptamers are described below.

Materials and Methods

Clinical samples derived from blood collected in STRECK cell free DNA blood collection tubes (BCTs) and processed to plasma are used. Samples collected from pregnant and non-pregnant females are collected under appropriate review board approval with patient consent, and are included in the investigations. Paired collections in additional blood collection tubes (ACD, Heparin, PPAK, Streck® Cell free DNA BCT (containing a crosslinking agent and an anticoagulant (EDTA)) and other blood collection tubes known in the art) are included in evaluations, to impact biomarker integrity. Plasma samples (pregnant and non-pregnant) are prepared from blood collected as above, or similar blood collection tubes containing an anticoagulant, by centrifugation to remove cells. Typical centrifugation conditions are: 800 g to 16,000 g for 5-30 min. In certain instances, centrifugation conditions are: 800 g to 2500 g for up to 30 min followed by 2500 g to 12,000 g for up to 30 min. Longer centrifugation speeds also may be used. Prepared plasma can be utilized directly for screening or enrichment, or can be frozen at −80° C. prior to use. For post freeze-thaw samples, an additional centrifugation step of 800 to 16,000 g for up to 30 min, or 800 g to 2500 g for up to 30 min is performed. In certain instances, subsequent centrifugation is not performed on post freeze-thaw samples.

Plasma samples may be subsequently subjected to crosslinking with a fixative such as formaldehyde or glutaraldehyde or another aldehyde or commonly known protein-protein or protein-DNA cross linking agent (e.g., N-hydrosuccinamide), or an agent which releases such a fixative, if not already included in blood collection tubes. Such processing can affect crosslinking to reinforce DNA-histone interaction prior to selective binding with targeted antibodies. Samples collected in a blood collection tube (BCT) containing a fixative such as formaldehyde or glutaraldehyde or another aldehyde or aldehyde releaser or other known protein-protein or protein-DNA cross linking agent, may not require additional fixation prior to binding with antibodies, however such fixation may be used irl certain instances. For example, samples collected in Streck® Cell-free DNA BCT may not require additional fixation prior to reaction with antibodies. If conditions close to physiologic normal with respect to pH (e.g., pH 6 to pH 8) and ionic strength normal are utilized for all processing steps, cross-linking may not be necessary regardless of BCT (e.g., solutions containing 140 mM sodium ion, 100 mM chloride ion, 25 mM carbonate, or having an overall molarity of 35 mM to 350 mM).

Antibodies to H1.1, H1.3, and/or H1.5 are investigated in positive selection approaches for fetal derived ccf DNA. Antibodies to H1.0 and/or H1 are targeted for depletion-based enrichment (negative selection) approaches. Antibodies to H1M histone (expressed in *Xenopus embryos*) and to H1FOO (expressed in oocytes) may cross react with human source material and thus offer selectivity to human fetal derived chromatin DNA. Such antibodies may be useful for a fetal ccf DNA positive selection strategy. There are eleven H1 variants characterized, and some may be specific (or show preferential binding) to ccf DNA of fetal source as outlined above. In addition, the use of an antibody to H1, without particular specificity may serve a suitable negative selection approach. Treatment of cleared plasma with one or more such antibodies in an immunoprecipitation protocol can effect significant depletion of maternal ccf DNA from a sample, thus enhancing ccf DNA fetal fraction.

Additionally, various maternal versus fetal differences in H3 histone subtype are exploited to enrich for fetal fraction. For example, antibodies recognizing one or more histone H3.1 conformational exposure differences in fetal versus maternal (e.g., sequence variance (e.g., extra 10 amino acids at the c-terminus of fetal H3.1), and particular methylation differences) are used for fetal DNA enrichment from plasma treated with such antibodies.

Certain antibodies are identified via assays using plasma samples processed as described above. ELISA, western blotting, Luminex or other similar approaches are used to rapidly test antibody selectivity. In such an assay system, selectivity for fetal or maternal specific ccf DNA initially is assessed based on cross reactivity to plasma samples derived from pregnant and non-pregnant women. Antibodies that demonstrate an ability to preferentially react with plasma derived from pregnant rather non-pregnant samples offer a degree of selectivity for fetal nucleosomes and thus are useful for positive selection approaches. Such antibodies are prioritized for preparative methods (e.g., immunoprecipitation) to enrich for fetal fraction. Antibodies that react across both sample types may be maternal specific and may bind only maternal ccf DNA (nucleosome bound), and thus are suitable to negative selection approaches (i.e., enrichment of fetal ccf DNA by depletion of maternal ccf DNA). Antibodies that react across both pregnant and non-pregnant samples, in certain instances, are further characterized and distinguished with respect to specificity (fetal versus maternal) by testing with DNA samples derived from peripheral blood mononuclear cells (PBMC) isolated from "buffy coat". Further validation of antibody histone selectivity is performed, in certain instances, using immunoprecipitation approaches and analysis of DNA fragments resulting from enrichment approaches. Sequencing and/or fetal specific assays such as FQA (fetal quantifier assay, for both male or/female fetuses) and/or qPCR assay (applicable to male fetuses) are further be used to validate specificity of antibodies, in certain instances.

Several ELISA assay formats are used for screening. Typical assay procedures are outlined here. After initial washes, a micro titer plate or other surface is first coated with a DNA binding protein or a histone binding antibody. The primary histone antibody should bind to any one of the 4 primary core histone types: H2A, H2B, H3, H4, to afford capture of all nucleosome DNA. This antibody should not be selective to specific histone subtypes or posttranslational modifications thereof to avoid tissue or cell cycle specificity. Similarly, the DNA binding protein should be non-specific to afford capture of all nucleosome DNA. Following several washes with buffer at neutral (or near neutral) pH and with similar physical isotonic strength, blocking with an agent such as casein or a bovine serum albumin containing agent is performed. Following several washes with buffer at neutral (or near neutral) pH and with similar physical isotonic strength, a portion of analyte plasma (either maternal pregnant (positive control) or non-pregnant (negative control)) is applied to each well. Capture of nucleosome DNA is achieved by incubation for at least 2 min at ambient temperature or after incubation at temperatures as high as 42° C. Following several washes with buffer at neutral (or near neutral) pH and with similar physiologic ionic strength, each of the antibodies tested for fetal histone or histone specific primary binding is applied to each well. This mixture is subjected to incubation typically for at least 2 min at ambient temperature or after incubation at temperatures as high as 42° C. Such primary antibody is typically labeled with biotin or another agent. Such primary antibody is unlabeled, in certain instances, in which case an isotype (species) specific antibody of different isotype (species) is used as the secondary antibody. In this step, only samples and antibodies with matched specificity will react with the primary antibody. Following several washes with buffer at neutral (or near neutral) pH and with similar physiological ionic strength, excess primary antibody is removed for each well. The secondary antibody, specific to either the label (e.g. streptavidin to biotin) to the isotype (species) of the primary antibody is then applied. The secondary antibody is directly labeled with a colorimetric or fluorescently labeled dye, in certain instances, or more typically is labeled with an enzyme which can convert a non-colorimetric or non-fluorescent agent to one that is visualized via colorimetric or fluorescent means. The secondary antibody is subjected to incubation typically for at least 2 min at ambient temperature or after incubation at temperatures as high as 42° C. Following several washes with buffer at neutral (or near neutral) pH and with similar physical ionic strength, excess secondary antibody is removed for each well. Following this step, a reporting agent is added. For example, an ABTS reagent mixture is added to a peroxidase labeled secondary antibody system. The color is allowed to develop and subsequently measured spectrophotometrically.

Rather than using a solid support for capture of the nucleosomes, a bead or microparticle (e.g., magnetic or non-magnetic) is used in-certain instances. Rather than using a soluble antibody, an antibody conjugated to or adsorbed onto a bead or microparticle is substituted to afford capture, in certain instances. Either a primary or secondary antibody can be conjugated or otherwise associated with the bead. For bead based solid support systems, analysis is conducted using a flow cytometer, in certain instances.

For methods where secondary calorimetric or fluorescent analysis is not required, one antibody specific to the captured material (e.g., nucleosomal DNA) is used, in certain instances. The antibody is labeled with streptavidin and captured with biotin labeled beads, in certain instances. Such a system allows preparative isolation of targeted nucleosome DNA.

In certain instances, a bead or microparticle is used to facilitate isolation of material with DNA having an enriched fetal fraction of nucleosomes (histone bound DNA), either via sedimentation (e.g., gravity sedimentation or centrifugation) or via separation with a magnet to collect magnetic beads. In certain instances, nucleosome ccf DNA is selected via positive selection with an antibody targeted to one or more fetal specific histones (as described above) and is separated from the bulk solution and washed of impurities with several washes with buffer at neutral (or near neutral) pH and with similar physical ionic strength. Nucleosome ccf DNA enriched with respect to fetal fraction is then eluted from the bead by adding an excess of competitor affinity tag to the system (e.g. in the case of biotin/streptavidin based binding, adding an excess of biotin labeled beads to an antibody conjugated to streptavidin (or visa versa)). Release is achieved with excess biotin or excess streptavidin, in certain instances. DNA is taken directly using a DNA extraction protocol (e.g., Qiagen circulating nucleic acid kit), in certain instances.

In certain instances, nucleosome ccf DNA is selected via negative selection with an antibody targeted to one or more maternal specific histones (as described above). In such instances, the maternal nucleosome DNA is separated from the bulk plasma, which contains ccf DNA depleted of maternal nucleosome bound DNA and the residual bulk plasma is enriched with respect to fetal DNA. The plasma sample is then processed via DNA extraction or direct analysis in amplification based (PCR) or sequencing approaches, in certain instances. DNA extraction is achieved using an extraction system such as the Qiagen circulating nucleic acid kit, in certain instances.

Several ELISA based assays for nucleosome detection are commercially available. These include, for example, Cell Death Detection ELISA-PLUS system (Roche) and QIA25 nucleosome ELISA kit (EMD Millipore, Calbiochem). Such assays can be modified to include specific anti-histone antibodies (fetal-specific or maternal-Specific as described herein) to identify and validate fetal versus maternal specificity.

Antibodies useful for maternal nucleosome DNA depletion (negative selection) include but are not limited to: Abcam Anti-Histone H1 antibody [1415-1]—Carboxyterminal end (ab62884), Abcam anti-histone H1.0 antibody (EPR6536) (ab134914), Abcam anti-histone H1 antibody (EPR6537) (ab125027), uniProt Antibody P10412, Histone H1.4 aka H1b, H1s4.

Antibodies useful for fetal nucleosome DNA enrichment (positive selection) include: Abcam Ltd. (Cambridge, UK): Anti-Histone H1.3 antibody H1.3 (ab24174), Anti-Histone H1.1 antibody H1.1 (ab17584), and Anti-Histone H1.5 antibodies H1.5 (ab24175), H1.5 (ab18208), Novus Biologics, Histone H1.3 Antibody (NBP1-41140), Abcam Ltd. (Cambridge, UK): H1.3 (ab24174) Fitzgerald, Histone H3.1 antibody (Phospho-Thr3) (70R-11156), Histone H3.1 antibody (70R-11159).

In some instances, placental villi tissue is isolated, and nuclei and contained chromatin and nucleosomes are prepared. This material is subsequently conjugated or combined with an adjuvant such as KLH to immunize rodents and illicit an immune response and thus generate antibodies. Monocolonal antibodies are isolated through methods that are well described in the literature. Such monoclonal antibodies are screened in ELISA as described above, with pregnant and nonpregnant plasma samples or via phage display.

Example 2: Fetal DNA Enrichment by Ultracentrifugation

In this example, the amount of fetal DNA and maternal DNA in circulating microparticles and in the "soluble" phase (i.e. not in microparticles) was estimated in pooled plasma samples from pregnant females. Plasma from pregnant subjects typically contains "free" DNA, nucleosomal DNA and DNA enclosed in circulating microparticles (e.g., apoptotic bodies) and collectively is termed ccfDNA. Ultracentrifugation can enrich circulating microparticles (cMPs) of different size (e.g., exosomes (about 70-120 nm diameter; carrying mainly RNA) from apoptotic bodies (about 300 nm to greater than about 1000 nm). About 90% of circulating apoptotic bodies contain DNA and about 10% contain RNA, typically with no mixed nucleic acid-containing particles. If the majority of apoptotic bodies at 10 to 12 weeks of pregnancy are of fetal origin, then the purification of apoptotic bodies is a means for enriching fetal DNA. Fractionation of subcellular structures by centrifugation at selected g-forces and sucrose (or PERCOLL) density centrifugation are used, in certain instances. Explanations for certain abbreviations and specialist terms used in this example are presented in Table 2 below.

TABLE 2

Abbreviations and specialist terms

| Abbreviation or specialist term | Explanation |
|---|---|
| ACD-A Tubes | Acid citrate dextrose (type A) blood collection tubes |
| BCT | Blood Collection Tube |
| ccf DNA | Circulating cell-free DNA |
| ccff DNA | Circulating cell-free fetal DNA |
| EDTA | Ethylenediaminetetraacetic acid, anti-coagulant commonly used in blood collection tubes |
| rxn | Reaction |
| SCAT PPACK BCT (A.K.A. SCAT-875B BCT) | Sample Collection/Anticoagulant Tubes with 75 µM PPACK protease inhibitor |
| Streck Tubes | Streck Cell-Free DNA Blood Collection Tubes |

Fetal DNA Enrichment by Ultracentrifugation (N=2)

In certain instances, the amount of fetal DNA and maternal DNA in circulating microparticles and in the "soluble" phase (i.e. not in microparticles) was estimated in pooled plasma samples from pregnant females using a small collection of samples (sometimes referred to as the "pre-test"). To show that fetal DNA is enriched in apoptotic bodies, cMPs in pooled plasma samples (N=2) were separated by ultracentrifugation. DNA was extracted from resulting supernatants and pellets, and quantified by qPCR assays (e.g., for β-globin and DYS1). Fetal fraction of supernatants and pellets were calculated so that fetal DNA enrichment, if present, was recorded. The majority of fetal DNA (74%) and total DNA (70%) of the original plasma (no ultracentrifugation) was in the "soluble" state, and not in the pellet, i.e. in cMPs. The distribution of total DNA and fetal DNA in the 25K×g pellet was 62% to 38%. Smaller exosomes typically do not harbor DNA but rather RNA. After centrifugation of the 25K supernatant at 100K×g the results showed a distribution of 82% of total DNA in the supernatant and 18% in the pellet, supporting the notion that particles (chiefly exosomes) in the 100K pellet may not contain large amounts of the available circulating DNA. The fetal fraction for the no-spin control was 0.06, for the 25K×g supernatant was 0.07 and for the 100K×g supernatant was 0.06. The fetal copy numbers in the pellets were too low to allow for sensible fetal fraction calculations.

Fetal DNA Enrichment by Ultracentrifugation

In certain instances, the amount of fetal DNA and maternal DNA in circulating microparticles and in the "soluble" phase (i.e. not in microparticles) was estimated in pooled plasma samples from pregnant females using a larger collection of samples. To show that fetal DNA is enriched in apoptotic bodies, the fetal fraction of appropriate ultracentrifugation supernatants and pellets was calculated.

Materials and Methods

Certain observations, predictions and/or conclusions were made when designing the assay below. For example, certain centrifugation conditions (e.g., 25,000×g for 1 hour) can sediment apoptotic bodies and larger, subcellular structures that do not get removed by prior centrifugations (e.g., 1600×g for 15 minutes and 2500×g for 10 minutes), in certain instances. The majority of enclosed fetal DNA resides in apoptotic bodies and not in other subcellular structures, in certain instances. The pre-test described above with 2×4 mL samples in replicate (16 mL total) was limited by a low sample number. For fetal DNA quantification the qPCR assay used was limited to the presence of Y-chromosomes (male fetus). Fetal DNA assayed by qPCR was corrected by a factor of 2 to reflect an estimated 50% male contribution in Super Pool 12.

Maternal peripheral blood was collected into three types of blood collection tubes (BCTs): SCAT PPACK BCT (1×), STRECK Cell-Free DNA BCT (2×STRECK Tubes) and ACD-A Tubes (2×). Within 6 hours plasma was produced using the standard STRECK Tube protocol: 1600×g for 15 minutes, removal of plasma, followed by 2500×g for 10 minutes, followed by frozen storage of the plasma samples. In some instances, plasma from STRECK Super Pool 12 (pregnant subjects, mainly at 10 to 12 weeks of gestation) was used immediately after the pool was created (24 mL), i.e., the plasma samples did not experience the standard freezing step.

To maintain the same experimental conditions, the "fresh" (frozen only once) plasma samples were centrifuged at 1600×g for 10 minutes at 4° C. to remove potential debris. The cleared plasma was used for ultracentrifugation studies.

In this example a sequential approach was developed: the supernatant of the first ultracentrifugation (25K×g) was added to a new centrifuge tube and spun at 100K×g. Ultracentrifugation steps were for 1 hour each. Plasma samples (4 mL) were run in duplicate and qPCR samples (5 µL) were run in quadruplicate. A Beckman Coulter Optima MAX-XP Centrifuge with MLS-50 Swinging Bucket Rotor was used along with Thinwall Polyallomer Tubes #356819. All centrifugations were performed at 4° C.

DNA in plasma and centrifugation supernatants was extracted using the 4 mL QIAGEN CNA Kit protocol. Elution volume was about 53 µL. DNA in pellets was extracted using the QIAGEN Investigator Kit. The pellets were resuspended in 200 µL of lysis solution were added. The final elution volume was about 40 µL. DNA was stored at 4° C. until used.

Analysis of DNA extracted from plasma ("supernatant") and pellets recovered after centrifugation included quantitative PCR (qPCR) assays targeting β-globin (total DNA copies) and DYS1 (copies of the Y-chromosome). In certain instances, quantification was performed using the standard curve method using TAQMAN human control genomic DNA (Life Tech #4312660). In certain instances, quantification was performed using a standard curve generated from non-pregnant female (NPF, total) and male villi (male/fetal). Experimental qPCR results were accepted when within the linear range of the β-globin or DYS1 standard curves. An example set-up for qPCR is presented in Table 3 below.

TABLE 3

| qPCR set-up | | | | | | |
|---|---|---|---|---|---|---|
| BgloLewis and DYS1 QPCR | Initial Conc (uM) | Final Conc (nM) | 1 rxn (10 uL) | 240 | Bglobin | DYS1 |
| Express QPCR Mastermix | 2x | 1X | 6 | 1440 | | |
| ROX | | | 0.24 | 57.6 | | |
| F Primer | 50 | 300 | 0.072 | 17.28 | | |
| R primer | 50 | 300 | 0.072 | 17.28 | | |
| Probe | 10 | 100 | 0.12 | 28.8 | | |
| DNA | | | 5 | | | |
| Water | | | 0.496 | 119.04 | | |
| | | Total | 12 | 1680 | | |

Stock: 104 c/uL NPF 1244 LMC 20121109

| | | c1v1 = c2v2 | |
|---|---|---|---|
| Maternal Top: | 2000 c/uL | (10000 c/uL * X uL) = (2000 c/uL) * 50 uL | |
| | | x = | 10 |
| | | H2O = | 40 |

| per 5 uL | per uL | previous standard | water |
|---|---|---|---|
| 10000 | 2000 | n/a | n/a |
| 2000 | 400 | 10 | 40 |
| 400 | 80 | 10 | 40 |
| 80 | 16 | 10 | 40 |
| 16 | 3.2 | 10 | 40 |
| 3.2 | 0.64 | 10 | 40 |
| 0.64 | 0.128 | 10 | 40 |

Stock: Male Villi 2500 c/uL 48838

| | | c1v1 = c2v2 | |
|---|---|---|---|
| Fetal Top: | 500 | (2500 c/uL * X uL) = (500 c/uL) * 50 uL | |
| | | x = | 10 |
| | | H2O = | 40 |

| per 5 uL | per uL | previous standard | water |
|---|---|---|---|
| 2500 | 500 | n/a | n/a |
| 500 | 100 | 10 | 40 |
| 100 | 20 | 10 | 40 |
| 20 | 4 | 10 | 40 |
| 4 | 0.8 | 10 | 40 |
| 0.8 | 0.16 | 10 | 40 |
| 0.16 | 0.032 | 10 | 40 |

Stock: Male Genomic 3030.3 c/uL

| | | c1v1 = c2v2 | |
|---|---|---|---|
| Top: | 2000 | (3030.3 c/uL * X uL) = (2000 c/uL) * 60 uL | |
| | | x = | 39.6000396 |
| | | H2O = | 20.3999604 |

| per 5 uL | per uL | previous standard | water |
|---|---|---|---|
| 10000 | 2000 | n/a | n/a |
| 2000 | 400 | 10 | 40 |
| 400 | 80 | 10 | 40 |
| 80 | 16 | 10 | 40 |
| 16 | 3.2 | 10 | 40 |
| 3.2 | 0.64 | 10 | 40 |
| 0.64 | 0.128 | 10 | 40 |

The qPCR assays for total DNA and fetal DNA in supernatants and pellets (input: 5 μL each) were run in quadruplicate reactions in separate wells. Supernatant qPCR results were expressed in copies/reaction (5 μL out of (53/4) μL, representing 37.6% of 1 mL plasma or 9.4% of 4 mL plasma). Conversion of copies/rxn to copies/mL was done by multiplying by 2.66. Pellet qPCR results were expressed in copies/rxn (5 μL out of 40 μL). In this instance, conversion of pellet copies/rxn to pellet copies/mL of plasma was done by multiplying by 2. FQA4b data for Super Pool 12 samples were expressed in copies/mL of plasma. A summary of assay reagents, instrumentation and software used in this example is provided in Table 4 below.

TABLE 4

| | Assay reagents, instrumentation, and software used | | |
|---|---|---|---|
| | Item | Vendor | Catalog # |
| Reagents | Express qPCR Master Mix | Life Technology | |
| | TaqMan Human Male Genomic Control DNA | Life Technology | 4312660 |
| | 50 bp DNA Ladder (50 µg, 1 µg/µL)) | Life Tech/Invitrogen | 10416-014 |
| | DNase I | VWR | PI90083 |
| | QIAamp DSP Circulating NA Kit | QIAGEN | 61504 |
| Labware | Streck Cell-Free DNA BCT | Streck | 218962 |
| | SCAT PPACK BCT 10 mL | Haematologic Technologies | SCAT-875B |
| | ACD-A Tubes 8.5 mL | VWR | VT4606 |
| Instrumentation | Centrifuge for 96-well plates | Beckman | n/a |
| | Microcentrifuge for 1.5 mL and 2 mL tubes | VWR | n/a |
| | Vortex | VWR | n/a |
| | ViiA 7 Real-Time PCR System with 384-Well Block | Life Technology | 4453536 |
| Software | MassARRAY ™ Nanodispenser, version 1.2.1 (RS1000) | Sequenom | Version 1.2.1 (RS1000) |
| | MassARRAY ™ Analyzer Workstation, includes: | Sequenom | |
| | ChipLinker | Sequenom | Version 20.0.1 |
| | AnalyzerControl | Sequenom | Version 2.3.45 |
| | SpectroCALLER | Sequenom | Version 3.4.1.42R |
| | SpectroACQUIRE, version 4.0.2.52 | Sequenom | Version 4.0.2.52 |
| | TypePLEX ™ MassARRAY ™ Typer 4.0 Software | Sequenom | n/a |
| | ViiA 7 | Life Technology | Version 1.2 |
| Reagents | Item | Vendor | Catalog # |
| | PCR Primer Oligos | IDT | Lot# 5510202 |

Results

Figure 2:
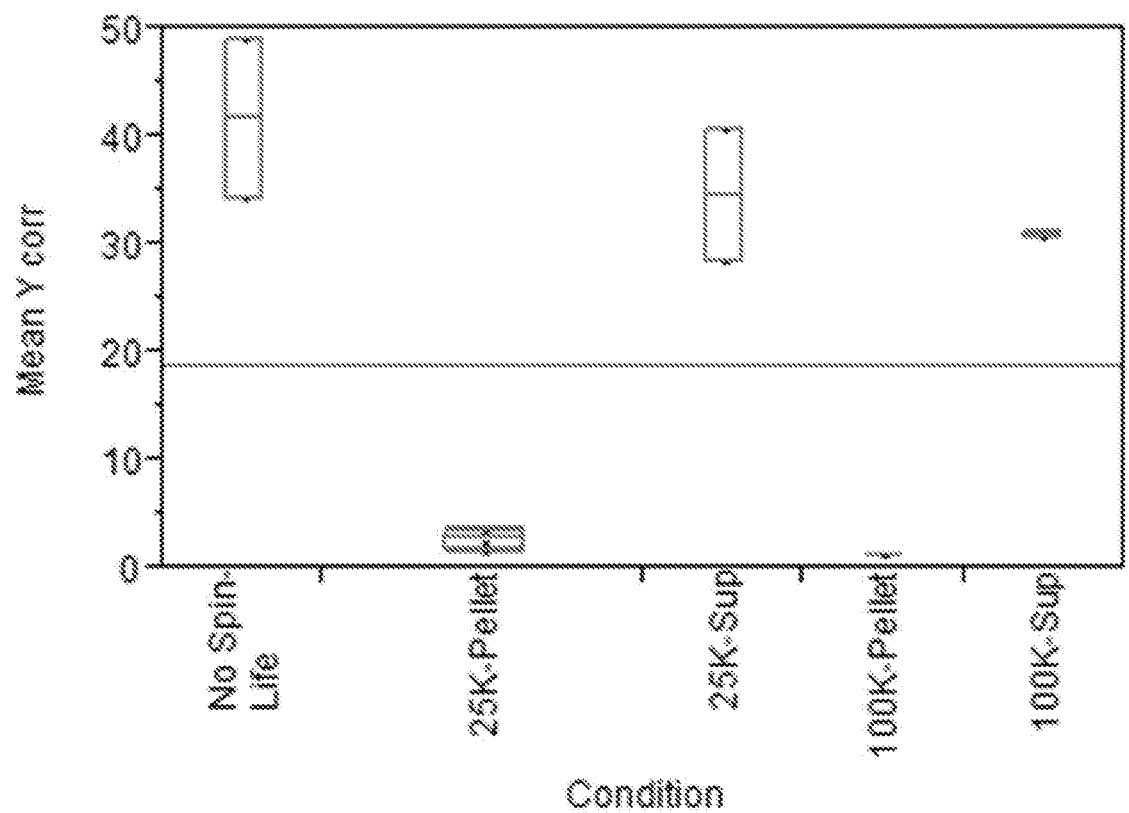
FIG. 2 shows fetal copy numbers obtained for certain centrifugation conditions.

DNA from Super Pool 12 plasma samples (frozen only once) was extracted using the standard QIAGEN CNA procedure and served as the reference for ultracentrifugation conditions. As determined by qPCR, the original plasma average was 42 fetal copies/rxn. In comparison, the 25K supernatant had 34 copies/rxn and the 25K pellets had 3 copies/rxn for a total of 37 fetal copies/rxn, compared to the original 42 fetal copies. The 100K supernatant had 31 copies/rxn and the 100K pellet had 1 copy/rxn for a total of 32 copies/rxn, again compared to the original 42 fetal copies. In contrast, for FQA4b the fetal copy number was 334 copies/mL in the pre-freeze sample (FIG. 2).

Figure 3:
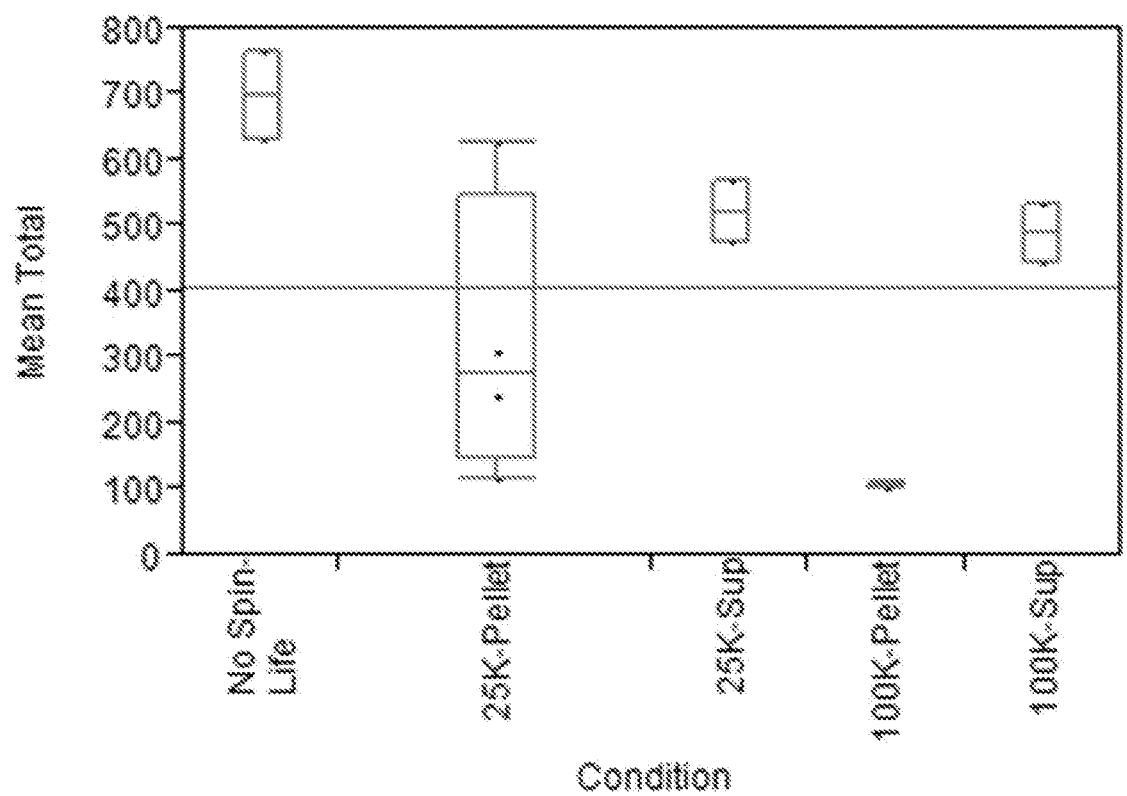
FIG. 3 shows total copy numbers obtained for certain centrifugation conditions.

For assessment of total copies, the original plasma average was 698 total DNA copies/rxn. In comparison, the 25K supernatant had 522 total DNA copies/rxn and the 25K pellets had 322 copies/rxn for a total of 844 fetal copies/rxn, compared to the original 522 fetal copies. The 100K supernatant had 489 total DNA copies/rxn and the 100K pellet had 107 total DNA copies/rxn for a total of 596 total DNA copies/rxn, compared to the original 698 total DNA copies. In contrast, for FQA4b the total DNA copy number was 5376 copies/mL in the pre-freeze sample (FIG. 3).

Figure 4:
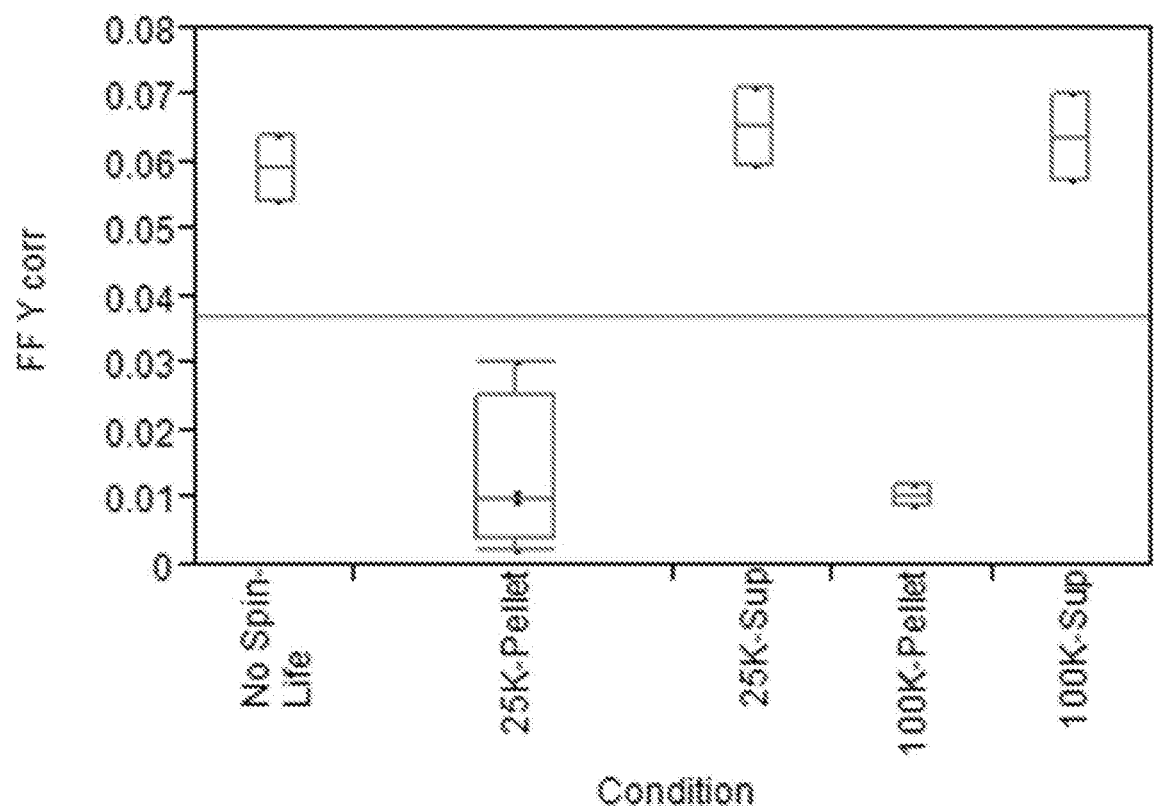
FIG. 4 shows fetal fractions obtained for certain centrifugation conditions.

Fetal Fraction in the original plasma was an average 0.06. In the 25K Supernatant the Fetal Fraction was 0.07 and in the corresponding Pellet it was 0.01 (Note: Only 3 fetal copies were detected and used in the calculation for Fetal Fraction in the pellet). The Fetal Fraction in the 100K Supernatant was 0.06 and 0.01 (Note: Only 1 fetal copy was detected and used in the calculation for Fetal Fraction in the pellet) in the 100K Pellet. In contrast, for FQA4b the Fetal Fraction using FQA4b was 0.07 (FIG. 4).

Mean total copies or mean fetal copies from supernatants (S) and pellets (P) were calculated for each condition. For the no-treatment control (Super Pool 12) only the supernatant was used (FIG. 5, columns 2 and 3 of the table). The grand total for each condition was calculated (FIG. 5, column 4 of the table). If there were no losses and the assays had high accuracy, these three numbers should not be different. The distribution of total and fetal DNA in supernatant and pellet for the two centrifugation conditions also was calculated (FIG. 5, columns 5 and 6 of the table). After the 25K×g centrifugation, 62% of total DNA was found in the supernatant and 38% in the pellet; the distribution changed after the 100K×g centrifugation to 82% and 18%, respectively.

The recovery of "soluble" total and fetal DNA was estimated by comparing the copy numbers per reaction for the no-spin, 25K and 100K centrifugation conditions. After the 25K×g centrifugation, 75% of total and 83% of fetal DNA were recovered in the supernatant (FIG. 6). A 6% loss of total DNA and a 10% loss of fetal DNA in the supernatant were observed after the 100K×g centrifugation step.

Overall, 70% of total DNA and 74% of fetal DNA were recovered from supernatants. Additionally, when comparing total and fetal copy number quantification by the two assays, qPCR assay and FQA4b, 27% of total DNA and 14% of fetal DNA in the plasma were recovered. Post-freeze values for FQA4b were used here, because of the additional 1600×g spin in both protocols (FIG. 6; SP 12=Super Pool 12).

Example 3: Examples of embodiments

A1. A method for enriching fetal nucleic acid in sample nucleic acid that includes fetal nucleic acid and maternal nucleic acid, comprising:
  (a) obtaining cell-free circulating sample nucleic acid from a biological sample from a pregnant female, which sample nucleic acid comprises vesicle-free nucleic acid and vesicular nucleic acid; and
  (b) separating some or substantially all of the vesicular nucleic acid from the sample nucleic acid, thereby generating a separation product enriched for the vesicle-free nucleic acid, wherein fetal nucleic acid in the separation product is enriched relative to fetal nucleic acid in the sample nucleic acid.

A2. The method of embodiment A1, comprising (c) analyzing nucleic acid in the separation product.

B1. A method which comprises analyzing nucleic acid in a separation product prepared by a process comprising:
- (a) obtaining cell-free circulating sample nucleic acid from a biological sample from a pregnant female, which sample nucleic acid comprises vesicle-free nucleic acid, vesicular nucleic acid, maternal nucleic acid and fetal nucleic acid; and
- (b) separating some or substantially all of the vesicular nucleic acid from the sample nucleic acid, thereby generating a separation, product enriched for the vesicle-free nucleic acid, wherein the fetal nucleic acid in the separation product is enriched relative to the fetal nucleic acid in the sample nucleic acid.

C1. A method for enriching vesicle-free nucleic acid in sample nucleic acid, comprising:
- (a) obtaining cell-free circulating sample nucleic acid from a biological sample, which sample nucleic acid comprises vesicle-free nucleic acid and vesicular nucleic acid; and
- (b) separating some or substantially all of the vesicular nucleic acid from the sample nucleic acid, thereby generating a separation product, wherein vesicle-free nucleic acid in the separation product is enriched relative to vesicle-free nucleic acid in the sample nucleic acid.

C2. The method of embodiment C1, comprising (c) analyzing nucleic acid in the separation product.

D1. A method which comprises analyzing nucleic acid in a separation product prepared by a process comprising:
- (a) obtaining cell-free circulating sample nucleic acid from a biological sample, which sample nucleic acid comprises vesicle-free nucleic acid and vesicular nucleic acid; and
- (b) separating some or substantially all of the vesicular nucleic acid from the sample nucleic acid, thereby generating a separation product, wherein vesicle-free nucleic acid in the separation product is enriched relative to vesicle-free nucleic acid in the sample nucleic acid.

D2. A method for enriching fetal nucleic acid in sample nucleic acid that includes fetal nucleic acid and maternal nucleic acid, comprising:
- (a) obtaining cell-free circulating sample nucleic acid from a biological sample from a pregnant female, which sample nucleic acid comprises maternal-derived vesicular nucleic acid and fetal-derived vesicular nucleic acid; and
- (b) separating some or substantially all of the maternal-derived vesicular nucleic acid from the fetal-derived vesicular nucleic acid, thereby generating a separation product enriched for the fetal-derived vesicular nucleic acid, wherein fetal nucleic acid in the separation product is enriched relative to fetal nucleic acid in the sample nucleic acid.

D3. A method for enriching fetal nucleic acid in sample nucleic acid that includes fetal nucleic acid and maternal nucleic acid, comprising:
- (a) obtaining cell-free circulating sample nucleic acid from a biological sample from a pregnant female, which sample nucleic acid comprises vesicle-free nucleic acid and vesicular nucleic acid; and
- (b) separating some or substantially all of the vesicular nucleic acid from the sample nucleic acid, thereby generating a separation product enriched for the vesicular nucleic acid, wherein fetal nucleic acid in the separation product is enriched relative to fetal nucleic acid in the sample nucleic acid.

D4. The method of embodiment D2 or D3, comprising (c) analyzing nucleic acid in the separation product.

E1. The method of any one of embodiments A1 to D4, wherein separating some or substantially all of the vesicular nucleic acid from the sample nucleic acid comprises filtering the sample nucleic acid.

E2. The method of any one of embodiments A1 to D4, wherein separating some or substantially all of the vesicular nucleic acid from the sample nucleic acid comprises centrifuging the sample nucleic acid.

E2.1 The method of embodiment E2, wherein centrifuging the sample nucleic acid comprises use of ultracentrifugation.

E3. The method of any one of embodiments A1 to D4, wherein separating some or substantially all of the vesicular nucleic acid from the sample nucleic acid comprises contacting the sample nucleic acid with an agent that specifically binds to vesicles comprising the vesicular nucleic acid.

E3.1 The method of embodiment D2, wherein separating some or substantially all of the maternal-derived vesicular nucleic acid from the fetal-derived vesicular nucleic acid comprises contacting the sample nucleic acid with an agent that specifically binds to maternal-derived vesicular nucleic acid.

E3.2 The method of embodiment D2; wherein separating some or substantially all of the maternal-derived vesicular nucleic acid from the fetal-derived vesicular nucleic acid comprises contacting the sample nucleic acid with an agent that specifically binds to fetal-derived vesicular nucleic acid.

E4. The method of embodiment E3 or E3.1, wherein the agent specifically binds to vesicles from hemopoietic tissue.

E5. The method of embodiment E4, wherein the agent specifically binds to vesicles from red blood cells.

E6. The method of embodiment E5, wherein the agent specifically binds to CD235a.

E7. The method of embodiment E4, wherein the agent specifically binds to vesicles from leukocytes.

E8. The method of embodiment E7, wherein the agent specifically binds to CD45.

E9. The method of embodiment E4, wherein the agent specifically binds to vesicles from lymphocytes.

E10. The method of embodiment E9, wherein the agent specifically binds to a vesicular component chosen from CD4, CD8 and CD20.

E11. The method of embodiment E4, wherein the agent specifically binds to vesicles from granulocytes.

E12. The method of embodiment E11, wherein the agent specifically binds to CD66b.

E13. The method of embodiment E4, wherein the agent specifically binds to vesicles from monocytes.

E14. The method of embodiment E13, wherein the agent specifically binds to CD14.

E15. The method of embodiment E4, wherein the agent specifically binds to vesicles from platelets.

E16. The method of embodiment E15, wherein the agent specifically binds to a vesicular component chosen from CD31, CD41, CD41a, CD42a, CD42b, CD61 and CD62P.

E17. The method of embodiment E3 or E3.1, wherein the agent specifically binds to vesicles from endothelial cells.

E18. The method of embodiment E17, wherein the agent specifically binds to a vesicular component chosen from CD31, CD34, CD54, CD62E, CD51, CD105, CD106, CD144 and CD146.

E18.1. The method of any one of embodiment E3 to E18, wherein generating the separation product comprises separating components bound by the agent away from the sample nucleic acid.

E19. The method of any one of embodiments A1 to E18.1, wherein separating some or substantially all of the vesicular nucleic acid from the sample nucleic acid further comprises contacting the sample nucleic acid with an agent that specifically binds to a histone associated with vesicle-free nucleic acid.

E19.1 The method of embodiment E19, wherein the agent specifically binds to histone H3.3.

E20. The method of embodiment E19, wherein the agent specifically binds to histone H1.

E20.1 The method of embodiment E20, wherein the histone H1 is unmethylated.

E20.2. The method of embodiment E19 or E20.1, wherein generating the separation product comprises separating components bound by the agent away from the sample nucleic acid.

E20.3. The method of any one of embodiments E3 to E20.2, wherein the agent is an antibody.

E21. The method of any one of embodiments A1 to E20.3, wherein the vesicular nucleic acid is within a vesicle having a diameter of less than about 1 micrometer.

E22. The method of embodiment E21, wherein the diameter is about 10 nanometers to about 600 nanometers.

E23. The method of embodiment E22, wherein the diameter is about 40 nanometers to about 100 nanometers.

E24. The method of any one of embodiments A1 to E23, wherein the sample nucleic acid is from blood plasma.

E25. The method of any one of embodiments A1 to E23, wherein the sample nucleic acid is from blood serum.

E26. The method of any one of embodiments A1 to E25, wherein obtaining the sample nucleic acid comprises subjecting the biological sample to an in vitro process that isolates the sample nucleic acid from other sample components.

E27. The method of any one of embodiments A1 to E25, wherein the separation product comprises about 50% or greater vesicle-free nucleic acid.

E28. The method of any one of embodiments A2, B1, C2, D1, D4 and E1 to E27, wherein analyzing the nucleic acid in the separation product comprises subjecting the nucleic acid to an in vitro sequencing process.

E29. The method of embodiment E28, wherein the sequencing process provides sequence reads.

E30. The method of embodiment E29, comprising mapping the sequence reads to a reference sequence.

E31. The method of embodiment E30, comprising counting the sequence reads mapped to the reference sequence.

E32. The method of embodiment E31, comprising utilizing the counted sequence reads to generate an outcome determinative of the presence or absence of a genetic variation.

E33. The method of embodiment E32, wherein the genetic variation is a copy number variation.

E34. The method of embodiment E32 or E33, wherein the genetic variation is a chromosome aneuploidy.

E35. The method of embodiment E34, wherein the chromosome aneuploidy is a chromosome 21 aneuploidy.

F1. A method for enriching fetal nucleic acid in sample nucleic acid that includes fetal nucleic acid and maternal nucleic acid, comprising:
  (a) obtaining cell-free circulating sample nucleic acid from a biological sample from a pregnant female, which sample nucleic acid comprises a first histone-associated nucleic acid species and a second histone-associated nucleic acid species; and
  (b) separating some or substantially all of the first histone-associated nucleic acid species from the sample nucleic acid, thereby generating a separation product enriched for the second histone-associated nucleic acid species, wherein fetal nucleic acid in the separation product is enriched relative to fetal nucleic acid in the sample nucleic acid.

F2. The method of embodiment F1, comprising (c) analyzing nucleic acid in the separation product.

G1. A method which comprises analyzing nucleic acid in a separation product prepared by a process comprising:
  (a) obtaining cell-free circulating sample nucleic acid from a biological sample from a pregnant female, which sample nucleic acid comprises a first histone-associated nucleic acid species, a second histone-associated nucleic acid species, maternal nucleic acid and fetal nucleic acid; and
  (b) separating some or substantially all of the first histone-associated nucleic acid species from the sample nucleic acid, thereby generating a separation product enriched for the second histone-associated nucleic acid species, wherein the fetal nucleic acid in the separation product is enriched relative to the fetal nucleic acid in the sample nucleic acid.

G2. The method of any one of embodiments F1 to G1, comprising lysing vesicles present in the sample nucleic acid.

H1. A method for enriching a histone-associated nucleic acid species in sample nucleic acid, comprising:
  (a) obtaining cell-free circulating sample nucleic acid from a biological sample, which sample nucleic acid comprises a first histone-associated nucleic acid species and a second histone-associated nucleic acid species; and
  (b) separating some or substantially all of the first histone-associated nucleic acid species from the sample nucleic acid, thereby generating a separation product enriched for the second histone-associated nucleic acid species.

H2. The method of embodiment H1, comprising (c) analyzing nucleic acid in the separation product.

I1. A method which comprises analyzing nucleic acid in a separation product prepared by a process comprising:
  (a) obtaining cell-free circulating sample nucleic acid from a biological sample, which sample nucleic acid comprises a first histone-associated nucleic acid species and a second histone-associated nucleic acid species; and
  (b) separating some or substantially all of the first histone-associated nucleic acid species from the sample nucleic acid, thereby generating a separation product enriched for the second histone-associated nucleic acid species.

I2. The method of any one of embodiments H1 to I1, comprising lysing vesicles present in the sample nucleic acid.

J1. The method of any one of embodiments F1 to I2, wherein separating some or substantially all of the first histone-associated nucleic acid species from the sample nucleic acid comprises contacting the sample nucleic acid with an agent that specifically binds to a histone associated with the first histone-associated nucleic acid species.

J2. The method of embodiment J1, wherein the agent specifically binds to histone H3.3.

J3. The method of embodiment J1, wherein the agent specifically binds to histone H1.

J3.1 The method of embodiment J3, wherein the histone H1 is unmethylated.

J4. The method of any one of embodiments J1 or J3.1, wherein generating the separation product comprises separating components bound by the agent away from the sample nucleic acid.

J4.1. The method of any one of embodiments J1 to J4, wherein the agent is an antibody.

J5. The method of any one of embodiments F1 to J4.1, wherein the sample nucleic acid is from blood plasma.

J6. The method of any one of embodiments F1 to J4.1, wherein the sample nucleic acid is from blood serum.

J7. The method of any one of embodiments F1 to J6, wherein obtaining the sample nucleic acid comprises subjecting the biological sample to an in vitro process that isolates the sample nucleic acid from other sample components.

J8. The method of any one of embodiments F1 to J7, wherein the separation product comprises about 50% or greater second histone-associated nucleic acid species.

J9. The method of any one of embodiments F2, G1, H2, I1 and J1 to J8, wherein analyzing the nucleic acid in the separation product comprises subjecting the nucleic acid to an in vitro sequencing process.

J10. The method of embodiment J9, wherein the sequencing process provides sequence reads.

J11. The method of embodiment J10, comprising mapping the sequence reads to a reference sequence.

J12. The method of embodiment J11, comprising counting the sequence reads mapped to the reference sequence.

J13. The method of embodiment J12, wherein the counted sequence reads are utilized to generate an outcome determinative of the presence or absence of a genetic variation.

J14. The method of embodiment J13, wherein the genetic variation is a copy number variation.

J15. The method of embodiment J13 or J14, wherein the genetic variation is a chromosome aneuploidy.

J16. The method of embodiment J15, wherein the chromosome aneuploidy is a chromosome 21 aneuploidy.

K1. A method for enriching fetal nucleic acid in sample nucleic acid that includes fetal nucleic acid and maternal nucleic acid, comprising:
(a) obtaining cell-free circulating sample nucleic acid from a biological sample from a pregnant female, which sample nucleic acid comprises a first histone-associated nucleic acid species and a second histone-associated nucleic acid species; and
(b) separating some or substantially all of the first histone-associated nucleic acid species from the second histone-associated nucleic acid species, thereby generating a separation product enriched for the second histone-associated nucleic acid species, wherein fetal nucleic acid in the separation product is enriched relative to fetal nucleic acid in the sample nucleic acid.

K2. The method of embodiment K1, comprising (c) analyzing nucleic acid in the separation product.

K3. The method of embodiment K1 or K2, wherein separating some or substantially all of the first histone-associated nucleic acid species from the second histone-associated nucleic acid species comprises contacting the sample nucleic acid with an agent that specifically binds to a histone associated with the first histone-associated nucleic acid species.

K4. The method of embodiment K1 or K2, wherein separating some or substantially all of the first histone-associated nucleic acid species from the second histone-associated nucleic acid species comprises contacting the sample nucleic acid with an agent that specifically binds to a histone associated with the second histone-associated nucleic acid species.

K5. The method of embodiment K3, wherein the agent specifically binds to histone H1.

K6. The method of embodiment K3, wherein the agent specifically binds to histone H1.0.

K7. The method of embodiment K4, wherein the agent specifically binds to histone H1.1.

K8. The method of embodiment K4, wherein the agent specifically binds to histone H1.3.

K9. The method of embodiment K4, wherein the agent specifically binds to histone H1.5.

K10. The method of embodiment K3, wherein the agent is an antibody.

K11. The method of embodiment K4, wherein the agent is an antibody.

K12. The method of any one of embodiments K1 to K11, wherein the sample nucleic acid is from blood plasma.

K13. The method of any one of embodiments K1 to K12, wherein obtaining the sample nucleic acid comprises subjecting the biological sample to an in vitro process that isolates the sample nucleic acid from other sample components.

K14. The method of embodiment K13, wherein the in vitro process comprises centrifugation.

K15. The method of any one of embodiments K1 to K14, wherein the separation product comprises about 50% or greater second histone-associated nucleic acid species.

K16. The method of any one of embodiments K2 to K15, wherein analyzing nucleic acid in the separation product comprises use of a sequencing process.

K17. The method of any one of embodiments K2 to K16, comprising (d) determining the presence or absence of a genetic variation according to the analysis in (c).

K18. The method of embodiment K17, wherein the genetic variation is a chromosome aneuploidy.

K19. The method of embodiment K18, wherein the chromosome aneuploidy is a chromosome 21 aneuploidy.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s)

What is claimed is:

1. A method for enriching cancer nucleic acid from a biological sample comprising cancer cells from a subject, wherein the sample nucleic acid comprises a first histone-associated nucleic acid species and a second histone-associated nucleic acid species, the method comprising, wherein the second histone-associated nucleic acid species is cancer nucleic acid:
   (a) contacting a cell-free circulating sample nucleic acid from a biological sample from a subject with an agent that specifically binds to a histone associated with normal nucleic acid species, wherein the histone is a H1 histone;
   which sample nucleic acid comprises a normal nucleic acid species and a tumor-derived nucleic acid species, wherein the histone H1 is H1.0 or H1b, and
   separating the histone associated normal nucleic acid species from the sample nucleic acid, thereby producing a separation product that is enriched for cancer nucleic acid in the sample nucleic acid; or
   b) contacting the cell-free circulating sample nucleic acid with an agent that specifically binds to a histone associated with the cancer nucleic acid species, wherein the histone is H3, wherein the histone H3 is H3.1, H3.2 or H3t, thereby enriching the cancer nucleic acid.

2. The method of claim 1, wherein the biological sample comprises cancer and non-cancer cells.

3. The method of claim 1, comprising (c) performing an assay to analyze nucleic acid in the separation product.

4. The method of claim 1, wherein the method step a) further comprises i) isolating cell free nucleic acids that are not bound to the agent that specifically binds to the H1 histone, and ii) contacting the isolated cell free nucleic acids from i) with an agent that specifically binds to H3.

5. The method of claim 1, wherein the H3 histone is methylated, or the H1 histone is unmethylated.

6. The method of claim 1, wherein the agent is an antibody.

7. The method of claim 1, wherein the a) contacting the sample nucleic acid with the agent involves immunoprecipitation.

8. The method of claim 1, wherein the biological sample comprises a blood sample, a serum sample, or a plasma sample.

9. The method of claim 1, wherein obtaining the sample nucleic acid comprises subjecting the biological sample to an in vitro process that isolates the sample nucleic acid from other sample components.

10. The method of claim 1, wherein the separation product comprises about 50% or greater second histone-associated nucleic acid species.

11. The method of claim 3, wherein the assay for analyzing nucleic acid in the separation product comprises use of a sequencing process.

12. The method of claim 3, wherein the assay detects the presence or absence of a genetic variation according to the assay performed in (c).

13. The method of claim 2, wherein the cancer cells are from a cancer selected from the group consisting of a breast cancer, a colorectal cancer, a gastrointestinal cancer, a hepatocellular cancer, a lung cancer, melanoma, non-Hodgkin lymphoma, leukemia, multiple myeloma, a bladder cancer, hepatoma, a cervical cancer, an esophageal cancer, a pancreatic cancer, or a prostate cancer.

14. A method for enriching tumor-derived nucleic acid species from a biological sample comprising cancer cells from a subject,
   (a) contacting a cell-free circulating sample nucleic acid from a biological sample from a subject with a first agent that specifically binds to a histone associated with the first histone-associated nucleic acid species, wherein the histone is an H1 histone, wherein the histone H1 is H1.0 or H1b;
   (b) separating the first histone-associated nucleic acid species that is bound to the agent away from the sample nucleic acid, thereby producing a separation product, wherein the separation product is enriched with second histone-associated nucleic acid species; and
   (c) contacting the separation product with a second agent that specifically binds to a histone associated with the second histone-associated nucleic acid species, wherein the histone is an H3 histone, wherein the histone H3 is H3.1, H3.2, or H3t.

* * * * *

UNITED STATES PATENT AND TRADEMARK OFFICE
CERTIFICATE OF CORRECTION

PATENT NO. : 11,312,997 B2
APPLICATION NO. : 16/884528
DATED : April 26, 2022
INVENTOR(S) : Charles R. Cantor It is certified that error appears in the above-identified patent and that said Letters Patent is hereby corrected as shown below:

In the Claims

In Column 90, Claim 14, Line 35, after "subject," insert --the method comprising:--.

Signed and Sealed this
Fifth Day of December, 2023

Katherine Kelly Vidal
*Director of the United States Patent and Trademark Office*